(12) United States Patent
Simón Vallés et al.

(10) Patent No.: US 10,081,840 B2
(45) Date of Patent: Sep. 25, 2018

(54) GENE EXPRESSION PROFILE AS AN ENDOMETRIAL RECEPTIVITY MARKER

(75) Inventors: Carlos Simón Vallés, Valencia (ES); José Antonio Horcajadas Almansa, Valencia (ES); Patricia Díaz Gimeno, Valencia (ES); Antonio Pellicer Martínez, Valencia (ES)

(73) Assignee: Igenomix S.L., Paterna (Valencia) (ES)

( * ) Notice: Subject to any disclaimer, the term of this patent is extended or adjusted under 35 U.S.C. 154(b) by 0 days.

(21) Appl. No.: 13/057,135

(22) PCT Filed: Jul. 22, 2009

(86) PCT No.: PCT/ES2009/000386
§ 371 (c)(1),
(2), (4) Date: Mar. 11, 2011

(87) PCT Pub. No.: WO2010/010213
PCT Pub. Date: Jan. 28, 2010

(65) Prior Publication Data
US 2012/0040849 A1     Feb. 16, 2012

(30) Foreign Application Priority Data
Jul. 22, 2008  (WO) ............... PCT/ES08/000513

(51) Int. Cl.
*C12Q 1/68*       (2018.01)
*C12Q 1/6883*     (2018.01)

(52) U.S. Cl.
CPC ...... *C12Q 1/6883* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | |
|---|---|---|
| 6,733,962 B2 | 5/2004 | Kliman et al. |
| 2003/0077589 A1 | 4/2003 | Hess-Stumpp et al. |
| 2003/0125282 A1 | 7/2003 | Weiss et al. |
| 2003/0186300 A1 | 10/2003 | Akoum |
| 2003/0228636 A1 | 12/2003 | Lessey |
| 2004/0005612 A1 | 1/2004 | Guidice et al. |
| 2005/0026891 A1 | 2/2005 | Hillisch et al. |
| 2005/0032111 A1 | 2/2005 | MacCalman et al. |
| 2005/0106134 A1 | 5/2005 | Nie et al. |
| 2013/0144114 A1 | 6/2013 | Vallés et al. |
| 2017/0097358 A1 | 4/2017 | Simón et al. |
| 2017/0128492 A1 | 5/2017 | Simón et al. |

FOREIGN PATENT DOCUMENTS

| | | |
|---|---|---|
| EP | 1 016 410 A1 | 7/2000 |
| JP | 2005-539016 A | 12/2005 |
| JP | 2007-504807 A | 3/2007 |
| JP | 2007-278750 A | 10/2007 |
| JP | 2008-501035 A | 1/2008 |
| WO | WO 90/13299 A1 | 11/1990 |
| WO | WO 01/89548 A2 | 11/2001 |
| WO | WO 03/062832 A1 | 7/2003 |
| WO | WO 2004/014935 A1 | 2/2004 |
| WO | WO 2004/058999 A2 | 7/2004 |
| WO | WO 2005/018796 A1 | 3/2005 |
| WO | WO 2005/026324 A2 | 3/2005 |
| WO | WO 2005/061725 A1 | 7/2005 |
| WO | WO 2005/117979 A2 | 12/2005 |
| WO | WO 2009/143633 A1 | 12/2009 |
| WO | WO 2013/057316 A2 | 4/2013 |
| WO | WO 2013/081554 A1 | 6/2013 |
| WO | WO 2014/001244 A1 | 1/2014 |

OTHER PUBLICATIONS

Mirkin et al., In search of candidate genes critically expressed in the human endometrium during the window of implantation; Human Reproduction vol. 20, No. 8, pp. 2104-2117, 2005.*
Shedden et al., Accurate Molecular Classification of Human Cancers Based on Gene Expression Using a Simple Classifier with a Pathological Tree-Based Framework; Amer. J. Pathology, vol. 165, No. 5, pp. 1985-1995, 2003.*
Anne Riesewijk, et al., "Gene Expression Profiling of Human Endometrial Receptivity on Days LH+2 Versus Lh+7 by Microarray Technology", Molecular Human Reproduction, 2003, pp. 253-264, vol. 9, No. 5.
Daniel D. Carson, et al., "Changes in Gene Expression During the Early to Mid-Luteal (Receptive Phase) Transition in Human Endometrium Detected by High-Density Microarray Screening", Molecular Human Reproduction, 2002, pp. 871-879, vol. 8, No. 9.
Jane M. Borthwick, et al., "Determination of the Transcript Profile of Human Endometrium", Molecular Human Reproduction, 2003, pp. 19-33, vol. 9, No. 1.
S. Talbi, et al., "Molecular Phenotyping of Human Endometrium Distinguishes Menstrual Cycle Phases and Underlying Biological Processes in Normo-Ovulatory Women", Endocrinology, 2006, pp. 1097-1121, vol. 147, No. 3.
Richard O. Burney, et al., "Gene Expression Analysis of Endometrium Reveals Progesternone Resistance and Candidate Susceptibility Genes in Women with Endometriosis", Endocrinology, 2007, pp. 3814-3826, vol. 148, No. 8.
J.A.Horcajadas, et al., "Effect of an Intrauterine Device on the Gene Expression Profile of the Endometrium", The Journal of Clinical Endocrinology & Metabolism, 2006, pp. 3199-3207, vol. 91, No. 8.
Jose, Antonio Horcajadas, et al., "Effect of Controlled Ovarian Hyperstimulation in IVF on Endometrial Gene Expression Profiles", Molecular human Reproduction, 2005, pp. 195-205, vol. 11, No. 3.

(Continued)

*Primary Examiner* — Addison D Ault
(74) *Attorney, Agent, or Firm* — Wolf, Greenfield & Sacks, P.C.

(57) ABSTRACT

The present invention relates to determining the receptivity of human endometrium from a gene expression profile. More specifically, the invention consists of developing a specific expression microarray of endometrial receptivity (Endometrial Receptivity Array or ERA) which allows evaluating the receptive state of a human endometrium, as well as assessing said state for diagnostic and therapeutic purposes.

12 Claims, 33 Drawing Sheets
Specification includes a Sequence Listing.

(56) References Cited

OTHER PUBLICATIONS

[No Author Listed], Agilent 012391 Whole Genome Oligo Microarray G4112A (Feature Number Version). Agilent Technologies. GEO. Nov. 17, 2004. [2 pages]. http://www.ncbi.nlm.nih.gov/geo/query/acc.cgi?acc=GPL1708. [last accessed Jan. 30, 2009].
Balasch et al., The usefulness of endometrial biopsy for luteal phase evaluation in infertility. Hum Reprod. Aug. 1992;7(7):973-7.
Batista et al., Midluteal phase endometrial biopsy does not accurately predict luteal function. Fertil Steril. Feb. 1993;59(2):294-300.
Catalano et al., The effect of RU486 on the gene expression profile in an endometrial explant model. Mol Hum Reprod. Aug. 2003;9(8):465-73.
Coutifaris et al., Histological dating of timed endometrial biopsy tissue is not related to fertility status. Fertil Steril. Nov. 2004;82(5):1264-72.
Creus et al., alphavbeta3 integrin expression and pinopod formation in normal and out-of-phase endometria of fertile and infertile women. Hum Reprod. Sep. 2002;17(9):2279-86.
Díaz-Gimeno et al., A genomic diagnostic tool for human endometrial receptivity based on the transcriptomic signature. Fertil Steril. Jan. 2011;95(1):50-60. Epub Jul. 8, 2010.
Gemzell-Danielsson et al., The effect of antiprogestin (RU 486) and prostaglandin biosynthesis inhibitor (naproxen) on uterine fluid prostaglandin F2 alpha concentrations. Hum Reprod. Sep. 1994;9(9):1626-30.
Horcajadas et al., Wide genomic analysis of human endometrial receptivity: new times, new opportunities. Hum Reprod Update. Jan.-Feb. 2007;13(1):77-86. Epub Sep. 7, 2006.
Kliman et al., Optimization of endometrial preparation results in a normal endometrial function test (EFT) and good reproductive outcome in donor ovum recipients. J Assist Reprod Genet. Jul.-Aug. 2006;23(7-8):299-303. Epub Sep. 17, 2006.
Lessey et al., Integrins as markers of uterine receptivity in women with primary unexplained infertility. Fertil Steril. Mar. 1995;63(3):535-42.
Li et al., How precise is histologic dating of endometrium using the standard dating criteria? Fertil Steril. May 1989;51(5):759-63.
Murray et al., A critical analysis of the accuracy, reproducibility, and clinical utility of histologic endometrial dating in fertile women. Fertil Steril. May 2004;81(5):1333-43.
Noyes et al., Dating the endometrial biopsy. Fertil Steril. 1950;1(1):3-17.
Ordi et al., Within-subject between-cycle variability of histological dating, alpha v beta 3 integrin expression, and pinopod formation in the human endometrium. J Clin Endocrinol Metab. May 2003;88(5):2119-25.
Papanikolaou et al., Early and late ovarian hyperstimulation syndrome: early pregnancy outcome and profile. Hum Reprod. Mar. 2005;20(3):636-41. Epub Dec. 2, 2004.
Ponnampalam et al., Molecular classification of human endometrial cycle stages by transcriptional profiling. Mol Hum Reprod. Dec. 2004;10(12):879-93. Epub Oct. 22, 2004.
Sharkey et al., Novel antiangiogenic agents for use in contraception. Contraception. Apr. 2005;71(4):263-71.
Shoupe et al., Correlation of endometrial maturation with four methods of estimating day of ovulation. Obstet Gynecol. Jan. 1989;73(1):88-92.
Simon et al., Similar endometrial development in oocyte donors treated with either high- or standard-dose GnRH antagonist compared to treatment with a GnRH agonist or in natural cycles. Hum Reprod. Dec. 2005;20(12):3318-27. Epub Aug. 5, 2005.
Tapia et al., Differences in the endometrial transcript profile during the receptive period between women who were refractory to implantation and those who achieved pregnancy. Hum Reprod. Feb. 2008;23(2):340-51. Epub Dec. 12, 2007.
Wilcox et al., Time of implantation of the conceptus and loss of pregnancy. N Engl J Med. Jun. 10, 1999;340(23):1796-9.
U.S. Appl. No. 13/574,291, filed Feb. 13, 2013, Vallés et al.
U.S. Appl. No. 15/127,901, filed Sep. 21, 2016, Simón et al.
U.S. Appl. No. 15/318,825, filed Dec. 14, 2016, Simón et al.
EP 10382011.4, Jul. 9, 2010, Partial European Search Report.
EP 10382011.4, Sep. 29, 2010, Extended European Search Report.
PCT/EP2011/050867, Apr. 19, 2011, International Search Report and Written Opinion.
PCT/EP2011/050867, Aug. 2, 2012, International Preliminary Report on Patentability.
PCT/ES2008/00513, Mar. 23, 2009, International Search Report and Written Opinion.
PCT/ES2008/00513, Mar. 8, 2011, International Preliminary Report on Patentability.
PCT/IB2015/001404, Nov. 19, 2015, International Search Report and Written Opinion.
PCT/IB2015/001404, Sep. 29, 2016, International Preliminary Report on Patentability.
PCT/IB2015/001715, Nov. 23, 2015, International Search Report and Written Opinion.
PCT/IB2015/001715, Dec. 29, 2016, International Preliminary Report on Patentability.
International Search Report and Written Opinion for Application No. PCT/EP2011/050867 dated Apr. 19, 2011.
International Preliminary Report on Patentability for Application No. PCT/EP2011/050867 dated Aug. 2, 2012.
Partial European Search Report for Application No. EP 10382011.4 dated Jul. 9, 2010.
Extended European Search Report for Application No. EP 10382011.4 dated Sep. 29, 2010.
International Search Report and Written Opinion dated Nov. 19, 2015 for Application No. PCT/IB2015/001404.
International Preliminary Report on Patentability dated Sep. 29, 2016 for Application No. PCT/IB2015/001404.
International Search Report and Written Opinion for PCT/IB2015/001715 dated Nov. 23, 2015.
International Preliminary Report on Patentability for PCT/IB2015/001715 dated Dec. 29, 2016.
International Search Report and Written Opinion for Application No. PCT/ES2008/00513 dated Mar. 23, 2009.
International Preliminary Report on Patentability for Application No. PCT/ES2008/00513 dated Mar. 8, 2011.
[No Author Listed], European IVF-Monitoring Consortium (EIM) for the European Society of Human Reproduction and Embryology (ESHRE) et al., Assisted reproductive technology in Europe, 2012: results generated from European registers by ESHRE. Hum Reprod. Aug. 2016;31(8):1638-52. doi: 10.1093/humrep/dew151. Epub Jun. 19, 2016.
[No Author Listed], Report of the National High Blood Pressure Education Program Working Group on High Blood Pressure in Pregnancy. Am J Obstet Gynecol. Jul. 2000;183(1):S1-522. Abstract Only.
Achache et al., Endometrial receptivity markers, the journey to successful embryo implantation. Hum Reprod Update. Nov.-Dec. 2006;12(6):731-46. Epub Sep. 18, 2006.
Agbulut et al., Comparison of human skeletal myoblasts and bone marrow-derived CD133+ progenitors for the repair of infarcted myocardium. J Am Coll Cardiol. Jul. 21, 2004;44(2):458-63.
Aghajanova et al., The bone marrow-derived human mesenchymal stem cell: potential progenitor of the endometrial stromal fibroblast. Biol Reprod. Jun. 2010;82(6):1076-87. doi: 10.1095/biolreprod.109.082867. Epub Feb. 10, 2010. Erratum in: Biol Reprod. May 2015;92(5):126.
Alawadhi et al., Bone Marrow-Derived Stem Cell (BMDSC) transplantation improves fertility in a murine model of Asherman's syndrome. PLoS One. May 12, 2014;9(5):e96662. doi: 10.1371/journal.pone.0096662. eCollection 2014.
Al-Shahrour et al., BABELOMICS: a systems biology perspective in the functional annotation of genome-scale experiments. Nucleic Acids Res. Jul. 1, 2006;34(Web Server issue):W472-6.
Al-Shahrour et al., FatiGO +: a functional profiling tool for genomic data. Integration of functional annotation, regulatory motifs and interaction data with microarray experiments. Nucleic Acids Res. Jul. 2007;35(Web Server issue):W91-6.

(56) References Cited

OTHER PUBLICATIONS

Al-Shahrour et al., FatiGO: a web tool for finding significant associations of Gene Ontology terms with groups of genes. Bioinformatics. Mar. 1, 2004;20(4):578-80.

Al-Shahrour et al., From genes to functional classes in the study of biological systems. BMC Bioinformatics. Apr. 3, 2007;8:114.

Am Esch et al., Infusion of CD133+ bone marrow-derived stem cells after selective portal vein embolization enhances functional hepatic reserves after extended right hepatectomy: a retrospective single-center study. Ann Surg. Jan. 2012;255(1):79-85. doi: 10.1097/SLA.0b013e31823d7d08.

Arnesen et al., Increased fibrinolytic activity after surgery induced by low dose heparin. Thromb Res. 1987; 45: 553-559. Abstract Only.

Asherman, Amenorrhoea traumatica (atretica). J Obstet Gynaecol Br Emp. Feb. 1948;55(1):23-30.

Barbash et al., Systemic delivery of bone marrow-derived mesenchymal stem cells to the infarcted myocardium: feasibility, cell migration, and body distribution. Circulation. Aug. 19, 2003;108(7):863-8. Epub Aug. 4, 2003.

Bastani et al., Determination of 8-epi PGF(2alpha) concentrations as a biomarker of oxidative stress using triple-stage liquid chromatography/tandem mass spectrometry. Rapid Commun Mass Spectrom. Sep. 2009;23(18):2885-90.

Beier et al., Plasminogen activator inhibitor-1 deficient mice are protected from angiotensin II-induced fibrosis. Arch Biochem Biophys. Jun. 1, 2011;510(1):19-26. doi: 10.1016/j.abb.2011.04.001. Author manuscript.

Belotti et al., Full GMP-compliant validation of bone marrow-derived human CD133(+) cells as advanced therapy medicinal product for refractory ischemic cardiomyopathy. Biomed Res Int. 2015;2015:473159. doi: 10.1155/2015/473159. Epub Oct. 1, 2015.

Benjamini et al., Controlling the false discovery rate: a practical and powerful approach to multiple testing. J Royal Statist Soc B 1995; 57: 289-300.

Bharadwaj et al., Annexin A2 heterotetramer: structure and function. Int J Mol Sci Mar. 19, 2013;14(3):6259-305. doi: 10.3390/ijms14036259.

Bongiovanni et al., The CD133+ cell as advanced medicinal product for myocardial and limb ischemia. Stem Cells Dev. Oct. 15, 2014;23(20):2403-21. doi: 10.1089/scd.2014.0111. Epub Aug. 20, 2014.

Boomsma et al., Cytokine profiling in endometrial secretions: a non-invasive window on endometrial receptivity. Reprod Biomed Online. Jan. 2009;18(1):85-94.

Boyd et al., Associations of personal and family preeclampsia history with the risk of early-, intermediate- and late-onset preeclampsia. Am J Epidemiol. Dec. 1, 2013;178(11):1611-9. doi: 10.1093/aje/kwt189.

Bradley et al., Transcatheter uterine artery embolisation to treat large uterine fibroids. Br J Obstet Gynaecol. Feb. 1998;105(2):235-40.

Brar et al., Progesterone-dependent decidualization of the human endometrium is mediated by cAMP. Endocrine. Jun. 1997;6(3):301-7. Abstract Only.

Bratincsák et al., CD45-positive blood cells give rise to uterine epithelial cells in mice. Stem Cells. Nov. 2007;25(11):2820-6. Epub Jul. 26, 2007.

Brosens et al., The role of the spiral arteries in the pathogenesis of preeclampsia. Obstet Gynecol Annu. 1972;1:177-91.

Brown et al., Endometrial glycodelin-A expression in the luteal phase of stimulated ovarian cycles. Fertil Steril. Jul. 2000;74(1):130-3.

Brumsted et al., Prostaglandin F2 alpha synthesis and metabolism by luteal phase endometrium in vitro. Fertil Steril. Nov. 1989;52(5):769-73.

Burton et al., Human early placental development: potential roles of the endometrial glands. Placenta. Apr. 2007;28 Suppl A:S64-9. Epub Mar. 8, 2007.

Cañas et al., Annexin A2 autoantibodies in thrombosis and autoimmune diseases. Thromb Res. Feb. 2015;135(2):226-30. doi: 10.1016/j.thromres.2014.11.034. Epub Dec. 13, 2014.

Capella-Allouc et al., Hysteroscopic treatment of severe Asherman's syndrome and subsequent fertility. Hum Reprod. May 1999;14(5):1230-3.

Casado-Vela et al., Comprehensive Proteomic Analysis of Human Endometrial Fluid Aspirate. Journal of Proteome Research. 2009;8:4622-4632.

Cervelló et al., Bone marrow-derived cells from male donors do not contribute to the endometrial side population of the recipient. PLoS One. 2012;7(1):e30260. doi: 10.1371/journal.pone.0030260. Epub Jan. 19, 2012.

Cervelló et al., Cell Therapy and Tissue Engineering from and toward the Uterus. Semin Reprod Med. Sep. 2015;33(5):366-72. doi: 10.1055/s-0035-1559581. Epub Aug. 18, 2015.

Cervelló et al., Human CD133$^+$ bone marrow-derived stem cells promote endometrial proliferation in a murine model of Asherman syndrome. Fertil Steril. Dec. 2015;104(6):1552-60.e1-3. doi: 10.1016/j.fertnstert.2015.08.032.

Cervelló et al., Human endometrial side population cells exhibit genotypic, phenotypic and functional features of somatic stem cells. PLoS One. Jun. 24, 2010;5(6):e10964. doi: 10.1371/journal.pone.0010964.

Cervelló et al., Reconstruction of endometrium from human endometrial side population cell lines. PLoS One. 2011;6(6):e21221. doi: 10.1371/journal.pone.0021221. Epub Jun. 21, 2011.

Cesarman et al., An endothelial cell receptor for plasminogen/tissue plasminogen activator (t-PA). II. Annexin II-mediated enhancement of t-PA-dependent plasminogen activation. J Biol Chem. Aug. 19, 1994;269(33):21198-203.

Cesarman-Maus et al., Autoantibodies against the fibrinolytic receptor, annexin 2, in antiphospholipid syndrome. Blood. Jun. 1, 2006;107(11):4375-82.

Cesarman-Maus et al., Molecular mechanisms of fibrinolysis. Br J Haematol. May 2005;129(3):307-21.

Cha et al., Molecular Interplay in Successful Implantation. Ten Critical Topics in Reproductive Medicine. Science/AAAS. 2013:44-48. doi: 10.1126/science.342.6164.1393-o.

Chartrand et al., Effect of dietary fat sources on systemic and intrauterine synthesis of prostaglandins during early pregnancy in gilts. J Anim Sci. Mar. 2003;81(3):726-34.

Cho et al., Lifetime expression of stem cell markers in the uterine endometrium. Fertil Steril. Feb. 2004;81(2):403-7.

Chu et al., Urokinase-type plasminogen activator, receptor, and inhibitor correlating with gelatinase-B (MMP-9) contribute to inflammation in gouty arthritis of the knee. J Rheumatol. Feb. 2006;33(2):311-7. Abstract Only.

Conserva et al., Recurrence and severity of abnormal pregnancy outcome in patients treated by low-molecular-weight heparin: a prospective pilot study. J Matern Fetal Neonatal Med. Aug. 2012;25(8):1467-73. doi: 10.3109/14767058.2011.643326.

Crabbe et al., Tissue plasminogen activator: a new thrombolytic agent. Clin Pharm. May 1987;6(5):373-86. Review. Erratum in: Clin Pharm Dec. 1987;6(12):925. Abstract Only.

Dimitrov et al., Characterization of clonogenic stromal cells isolated from human endometrium. Reproduction. Apr. 2008;135(4):551-8. doi: 10.1530/REP-07-0428.

Dmowski et al., Asherman's syndrome and risk of placenta accreta. Obstet Gynecol. Aug. 1969;34(2):288-99.

Dome et al., Circulating bone marrow-derived endothelial progenitor cells: characterization, mobilization, and therapeutic considerations in malignant disease. Cytometry A. Mar. 2008;73(3):186-93.

Domínguez et al., Proteomic analysis of the human receptive versus non-receptive endometrium using differential in-gel electrophoresis and MALDI-MS unveils stathmin 1 and annexin A2 as differentially regulated. Hum Reprod. Oct. 2009;24(10):2607-17. doi: 10.1093/humrep/dep230.

Downie et al., Levels of prostaglandins in human endometrium during the normal menstrual cycle. J Physiol. Jan. 1974;236(2):465-72.

(56) References Cited

OTHER PUBLICATIONS

Du et al., Contribution of bone marrow-derived stem cells to endometrium and endometriosis. Stem Cells. Aug. 2007;25(8):2082-6. Epub Apr. 26, 2007.
Du et al., Ischemia/reperfusion injury promotes and granulocyte-colony stimulating factor inhibits migration of bone marrow-derived stem cells to endometrium. Stem Cells Dev. Dec. 10, 2012;21(18):3324-31. doi: 10.1089/scd.2011.0193. Epub Aug. 16, 2012.
Dunn et al., Decidualization of the human endometrial stromal cell: an enigmatic transformation. Reprod Biomed Online. Sep. 2003;7(2):151-61. Abstract Only.
Fadini et al., Critical reevaluation of endothelial progenitor cell phenotypes for therapeutic and diagnostic use. Circ Res. Feb. 17, 2012;110(4):624-37. doi: 10.1161/CIRCRESAHA.111.243386.
Farhi et al., Induced regeneration of endometrium following curettage for abortion: a comparative study. Hum Reprod. Jul. 1993;8(7):1143-4.
Flores-Ramírez et al., Intracoronary infusion of CD133+ endothelial progenitor cells improves heart function and quality of life in patients with chronic post-infarct heart insufficiency. Cardiovasc Revasc Med. Apr.-Jun. 2010;11(2):72-8. doi: 10.1016/j.carrev.2009.04.001.
Founds et al., Altered global gene expression in first trimester placentas of women destined to develop preeclampsia. Placenta. Jan. 2009;30(1):15-24. doi: 10.1016/j.placenta.2008.09.015. Epub No. 21, 2008. Author manuscript.
Freund et al., Comparative analysis of proliferative potential and clonogenicity of MACS-immunomagnetic isolated CD34+ and CD133+ blood stem cells derived from a single donor. Cell Prolif. Aug. 2006;39(4):325-32.
Friel et al., Epigenetic regulation of CD133 and tumorigenicity of CD133 positive and negative endometrial cancer cells. Reprod Biol Endocrinol. Dec. 1, 2010;8:147. doi: 10.1186/1477-7827-8-147.
Fürst et al., Portal vein embolization and autologous CD133+ bone marrow stem cells for liver regeneration: initial experience. Radiology. Apr. 2007;243(1):171-9. Epub Feb. 20, 2007.
Gargett et al., Adult stem cells in the endometrium. Mol Hum Reprod. Nov. 2010;16(11):818-34. doi: 10.1093/molehr/gaq061. Epub Jul. 13, 2010.
Gargett et al., Generating receptive endometrium in Asherman's syndrome. J Hum Reprod Sci. Jan. 2011;4(1):49-52.
Gargett et al., Isolation and culture of epithelial progenitors and mesenchymal stem cells from human endometrium. Biol Reprod. Jun. 2009;80(6):1136-45. doi:10.1095/biolreprod.108.075226. Epub Feb. 18, 2009.
Garrido-Gómez et al., Annexin A2 is critical for embryo adhesiveness to the human endometrium by RhoA activation through F-actin regulation. FASEB J. Sep. 2012;26(9):3715-27. doi: 10.1096/fj.12-204008. Abstract Only.
Garrido-Gomez et al., Modeling human endometrial decidualization from the interaction between proteome and secretome. J Clin Endocrinol Metab. Mar. 2011;96(3):706-16. doi: 10.1210/jc.2010-1825.
Gellersen et al., Invasiveness of human endometrial stromal cells is promoted by decidualization and by trophoblast-derived signals. Hum Reprod. Apr. 2010;25(4):862-73. doi:10.1093/humrep/dep468.
Giudice et al., Paracrine actions of insulin-like growth factors and IGF binding protein-1 in non-pregnant human endometrium and at the decidual-trophoblast interface. J Reprod Immunol. Aug. 1998;39(1-2):133-48. Abstract Only.
Giudice, Potential biochemical markers of uterine receptivity. Hum Reprod. Dec. 1999;14 Suppl 2:3-16.
Gohil et al., The genetics of venous thromboembolism. A meta-analysis involving approximately 120,000 cases and 180,000 controls. Thromb Haemost. Aug. 2009;102(2):360-70. doi: 10.1160/TH09-01-0013. Abstract Only.
Goodwin et al., Uterine artery embolization for treatment of leiomyomata: long-term outcomes from the FIBROID Registry. Obstet Gynecol. Jan. 2008;111(1):22-33. doi: 10.1097/01.AOG.0000296526.71749.c9n.
Gordon et al., Large-scale isolation of CD133+ progenitor cells from G-CSF mobilized peripheral blood stem cells. Bone Marrow Transplant. Jan. 2003;31(1):17-22.
Goussetis et al., Intracoronary infusion of CD133+ and CD133-CD34+ selected autologous bone marrow progenitor cells in patients with chronic ischemic cardiomyopathy: cell isolation, adherence to the infarcted area, and body distribution. Stem Cells. Oct. 2006;24(10):2279-83. Epub Jun. 22, 2006.
Gray et al., Evidence that absence of endometrial gland secretions in uterine gland knockout ewes compromises conceptus survival and elongation. Reproduction. Aug. 2002;124(2):289-300.
Handgretinger et al., Biology and plasticity of CD133+ hematopoietic stem cells. Ann NY Acad Sci. May 2003;996:141-51.
Handgretinger et al., CD133-Positive Hematopoietic Stem Cells: From Biology to Medicine. Adv Exp Med Biol. 2013;777:99-111. doi: 10.1007/978-1-4614-5894-4_7.
Haus et al., CD133-enriched Xeno-Free human embryonic-derived neural stem cells expand rapidly in culture and do not form teratomas in immunodeficient mice. Stem Cell Res. Sep. 2014;13(2):214-26. doi: 10.1016/j.scr.2014.06.008.
Herrero et al., A hierarchical unsupervised growing neural network for clustering gene expression patterns. Bioinformatics. Feb. 2001;17(2):126-36.
Hida et al., Novel cardiac precursor-like cells from human menstrual blood-derived mesenchymal cells. Stem Cells. Jul. 2008;26(7):1695-704. doi: 10.1634/stemcells.2007-0826. Epub Apr. 17, 2008.
Hoozemans et al., Human embryo implantation: current knowledge and clinical implications in assisted reproductive technology. Reprod Biomed Online. Dec. 2004;9(6):692-715.
Ikoma et al., Bone marrow-derived cells from male donors can compose endometrial glands in female transplant recipients. Am J Obstet Gynecol. Dec. 2009;201(6):608.e1-8. doi:10.1016/j.ajog.2009.07.026. Epub Oct. 3, 2009.
Irollo et al., CD133: to be or not to be, is this the real question? Am J Transl Res. Sep. 25, 2013;5(6):563-81.
Irwin et al., Sex steroids and growth factors differentially regulate the growth and differentiation of cultured human endometrial stromal cells. Endocrinology. Nov. 1991;129(5):2385-92. Abstract Only.
Ishihara et al., Metabolism of arachidonic acid and synthesis of prostanoids in human endometrium and decidua. Prostaglandins Leukot Med. Sep. 1986;24(1):93-102.
Jabbour et al., Potential roles of decidual prolactin in early pregnancy. Reproduction. Feb. 2001;121(2):197-205.
Jaime-Pérez et al., Assessment of immune reconstitution status in recipients of a successful hematopoietic stem cell transplant from peripheral blood after reduced intensity conditioning. Blood Cells Mol Dis. May 2016;58:52-6. doi: 10.1016/j.bcmd.2016.03.001. Epub Mar. 3, 2016.
Jensen et al., Prostaglandins in the menstrual cycle of women. A review. Dan Med Bull. Jun. 1987;34(3):178-82.
Jimenez-Quevedo et al., Selected CD133+ progenitor cells to promote angiogenesis in patients with refractory angina: final results of the Progenitor randomized trial. Circ Res. Nov. 7, 2014;115(11):950-60. doi: 10.1161/CIRCRESAHA.115.303463. Epub Sep. 17, 2014.
Jing et al., Rat bone marrow mesenchymal stem cells improve regeneration of thin endometrium in rat. Fertil Steril. Feb. 2014;101(2):587-94. doi: 10.1016/j.fertnstert.2013.10.053. Epub Dec. 17, 2013.
Kamei et al., Ex-vivo expanded human blood-derived CD133+ cells promote repair of injured spinal cord. J Neurol Sci. May 15, 2013;328(1-2):41-50. doi: 10.1016/j jns.2013.02.013.
Kato et al., Characterization of side-population cells in human normal endometrium. Hum Reprod. May 2007;22(5):1214-23. Epub Feb. 5, 2007.
Kelly et al., The relationship between menstrual blood loss and prostaglandin production in the human: evidence for increased availability of arachidonic acid in women suffering from menorrhagia. Prostaglandins Leukot Med. Oct. 1984;16(1):69-78.

(56) References Cited

OTHER PUBLICATIONS

Kijima et al., Regeneration of peripheral nerve after transplantation of CD133+ cells derived from human peripheral blood. J Neurosurg. Apr. 2009;110(4):758-67. doi: 10.3171/2008.3.17571.

Kordes et al., CD133+ hepatic stellate cells are progenitor cells. Biochem Biophys Res Commun. Jan. 12, 2007;352(2):410-7. Epub Nov. 15, 2006.

Kruse-Blinkenberg et al., The influence of low dose heparin in elective surgery on blood coagulation, fibrinolysis, platelet function, antithrombin III and antiplasmin. Acta Chir Scand. 1980;146(6):375-82. Abstract Only.

Lessey, Endometrial receptivity and the window of implantation. Baillieres Best Pract Res Clin Obstet Gynaecol. Oct. 2000;14(5):775-88.

Lessey, Two pathways of progesterone action in the human endometrium: implications for implantation and contraception. Steroids. Nov. 2003;68(10-13):809-15.

Li, CD133: a stem cell biomarker and beyond. Exp Hematol Oncol. Jul. 1, 2013;2(1):17. doi: 10.1186/2162-3619-2-17.

Liew et al., Endothelial progenitor cells: diagnostic and therapeutic considerations. BioEssays. Mar. 2006;28(3):261-70.

Lim et al., Molecules in blastocyst implantation: uterine and embryonic perspectives. Vitam Horm. 2002;64:43-76.

Lim et al., Prostaglandin E2 receptor subtype EP2 gene expression in the mouse uterus coincides with differentiation of the luminal epithelium for implantation. Endocrinology. Nov. 1997;138(11):4599-606.

Ling et al., Annexin II regulates fibrin homeostasis and neoangiogenesis in vivo. J Clin Invest. Jan. 2004;113(1):38-48.

Ma et al., Intramyocardial delivery of human CD133+ cells in a SCID mouse cryoinjury model: Bone marrow vs. cord blood-derived cells. Cardiovasc Res. Jul. 1, 2006;71(1):158-69. Epub Apr. 3, 2006.

Maathuis et al., Concentrations of prostaglandins F2alpha and E2 in the endometrium throughout the human menstrual cycle, after the administration of clomiphene or an oestrogen-progestogen pill and in early pregnancy. J Endocrinol. Jun. 1978;77(3):361-71.

Maathuis, Cyclic changes in the concentration of prostaglandin F2alpha in human uterine flushings. Br J Obstet Gynaecol. Mar. 1978;85(3):207-10.

Manginas et al., Pilot study to evaluate the safety and feasibility of intracoronary CD133+ and CD133-CD34+cell therapy in patients with nonviable anterior myocardial infarction. Catheter Cardiovasc Interv. May 1, 2007;69(6):773-81.

Manns et al., Prostaglandin Concentrations in Uterine Fluid of Cows with Pyometra. Can J Comp Med. 1985;49:436-438.

Mansour et al., Compare-AMI trial: comparison of intracoronary injection of CD133+ bone marrow stem cells to placebo in patients after acute myocardial infarction and left ventricular dysfunction: study rationale and design. J Cardiovasc Transl Res. Apr. 2010;3(2):153-9. doi: 10.1007/s12265-009-9145-2. Epub Nov. 12, 2009.

March, Management of Asherman's syndrome. Reprod Biomed Online. Jul. 2011;23(1):63-76. doi: 10.1016/j.rbmo.2010.11.018. Epub Dec. 4, 2010.

Masuda et al., Estrogen-mediated endothelial progenitor cell biology and kinetics for physiological postnatal vasculogenesis. Circ Res. Sep. 14, 2007;101(6):598-606. Epub Jul. 26, 2007.

Masuda et al., Stem cell-like properties of the endometrial side population: implication in endometrial regeneration. PLoS One. Apr. 28, 2010;5(4):e10387. doi: 10.1371/journal.pone.0010387.

Meng et al., Endometrial regenerative cells: a novel stem cell population. J Transl Med. Nov. 15, 2007;5:57.

Menkhorst et al., Decidual-secreted factors alter invasive trophoblast membrane and secreted proteins implying a role for decidual cell regulation of placentation. PLoS One. 2012;7(2):e31418. doi: 10.1371/journal.pone.0031418. Epub Feb. 16, 2012.

Meyer, Luteal versus placental progesterone: the situation in the cow, pig and bitch. Exp Clin Endocrinol. 1994;102(3):190-2. Biosis abstract accession No. PREV199497469780.

Mints et al., Endometrial endothelial cells are derived from donor stem cells in a bone marrow transplant recipient. Hum Reprod. Jan. 2008;23(1):139-43. Epub Nov. 2, 2007.

Morelli et al., Experimental evidence for bone marrow as a source of nonhematopoietic endometrial stromal and epithelial compartment cells in a murine model. Biol Reprod. Jul. 11, 2013;89(1):7. doi: 10.1095/biolreprod.113.107987. Print Jul. 2013.

Musina et al., Endometrial mesenchymal stem cells isolated from the menstrual blood. Bull Exp Biol Med. Apr. 2008;145(4):539-43.

Mutlu et al., The endometrium as a source of mesenchymal stem cells for regenerative medicine. Biol Reprod. Jun. 2015;92(6):138. doi: 10.1095/biolreprod.114.126771. Epub Apr. 22, 2015.

Nagori et al., Endometrial regeneration using autologous adult stem cells followed by conception by in vitro fertilization in a patient of severe Asherman's syndrome. J Hum Reprod Sci. Jan. 2011;4(1):43-8. doi: 10.4103/0974-1208.82360.

Naicker et al., Quantitative analysis of trophoblast invasion in preeclampsia. Acta Obstet Gynecol Scand. Aug. 2003;82(8):722-9. Abstract Only.

Nasseri et al., Autologous CD133+ bone marrow cells and bypass grafting for regeneration of ischaemic myocardium: the Cardio133 trial. Eur Heart J. May 14, 2014;35(19):1263-74. doi: 10.1093/eurheartj/ehu007. Epub Feb. 3, 2014.

Nikas et al., Endometrial pinopodes: some more understanding on human implantation? Reprod Biomed Online. 2002;4 Suppl 3:18-23.

Pijnenborg et al., Fetal-maternal conflict, trophoblast invasion, preeclampsia, and the red queen. Hypertens Pregnancy. 2008;27(2):183-96. doi: 10.1080/10641950701826711. Abstract Only.

Pistofidis et al., Comparison of Operative and Fertility Outcome Between Groups of Women with Intrauterine Adhesions after Adhesiolysis. J Am Assoc Gynecol Laparosc. Aug. 1996;3(4, Supplement):S40.

Pittenger et al., Multilineage potential of adult human mesenchymal stem cells. Science. Apr. 2, 1999;284(5411):143-7.

Pogliani et al., Low-dose heparin in thoracic surgery: effect on blood coagulation and fibrinolysis system. Thromb Res. Jul. 15, 1982;27(2):211-9. Abstract Only.

Pompilio et al., Direct minimally invasive intramyocardial injection of bone marrow-derived AC133+ stem cells in patients with refractory ischemia: preliminary results. Thorac Cardiovasc Surg. Mar. 2008;56(2):71-6. doi: 10.1055/s-2007-989351.

Rabaglino et al., A bioinformatics approach reveals evidence for impaired endometrial maturation before and during early pregnancy in women who developed preeclampsia. Hypertension. Feb. 2015;65(2):421-9. doi: 10.1161/Hypertensionaha.114.04481. Epub Nov. 24, 2014. Erratum in: Hypertension. Jun. 2015;65(6):e46-7. Author manuscript.

Rafii et al., Therapeutic stem and progenitor cell transplantation for organ vascularization and regeneration. Nat Med. Jun. 2003;9(6):702-12.

Ramathal et al., Endometrial decidualization: of mice and men. Semin Reprod Med. Jan. 2010;28(1):17-26. doi: 10.1055/s-0029-1242989. Author manuscript.

Ravina et al., Arterial embolisation to treat uterine myomata. The Lancet. Sep. 9, 1995;346(8976):671-2.

Rees et al., Endometrial and myometrial prostaglandin release during the menstrual cycle in relation to menstrual blood loss. J Clin Endocrinol Metab. May 1984;58(5):813-8.

Reijnen et al., The antiadhesive agent sodium hyaluronate increases the proliferation rate of human peritoneal mesothelial cells. Fertil Steril. Jul. 2000;74(1):146-51.

Richardson et al., CD133, a novel marker for human prostatic epithelial stem cells. J Cell Sci. Jul. 15, 2004;117(Pt 16):3539-45. Epub Jun. 29, 2004.

Robb et al., Leukemia inhibitory factor and interleukin-11: cytokines with key roles in implantation. J Reprod Immunol. Oct.-Nov. 2002;57(1-2):129-41.

Roberts et al., Preeclampsia: recent insights. Hypertension. Dec. 2005;46(6):1243-9.

Roberts et al., The placenta in pre-eclampsia and intrauterine growth restriction. J Clin Pathol. Dec. 2008;61(12):1254-60. doi: 10.1136/jcp.2008.055236. Abstract Only.

(56) References Cited

OTHER PUBLICATIONS

Saed et al., Hypoxia-induced irreversible up-regulation of type I collagen and transforming growth factor-beta1 in human peritoneal fibroblasts. Fertil Steril Jul. 2002;78(1):144-7.
Sagrinati et al., Isolation and characterization of multipotent progenitor cells from the Bowman's capsule of adult human kidneys. J Am Soc Nephrol. Sep. 2006;17(9):2443-56. Epub Aug. 2, 2006.
Salle et al., Antibodies directed against annexin A2 and obstetric morbidity. J Reprod Immunol. Nov. 2016;118:50-53. doi: 10.1016/j.jri.2016.08.010.
Santamaria et al., Autologous cell therapy with CD133+ bone marrow-derived stem cells for refractory Asherman's syndrome and endometrial atrophy: a pilot cohort study. Hum Reprod. May 2016;31(5):1087-96. doi: 10.1093/humrep/dew042. Epub Mar. 22, 2016.
Schmohl et al., CD133, Selectively Targeting the Root of Cancer. Toxins (Basel). May 28, 2016;8(6). pii: E165. doi: 10.3390/toxins8060165.
Schots et al., Evidence that intracoronary-injected CD133+ peripheral blood progenitor cells home to the myocardium in chronic postinfarction heart failure. Exp Hematol. Dec. 2007;35(12):1884-90. Epub Oct. 17, 2007.
Schwab et al., Co-expression of two perivascular cell markers isolates mesenchymal stem-like cells from human endometrium. Hum Reprod. Nov. 2007;22(11):2903-11. Epub Sep. 14, 2007.
Schwab et al., Putative stem cell activity of human endometrial epithelial and stromal cells during the menstrual cycle. Fertil Steril. Oct. 2005;84 Suppl 2:1124-30.
Senturk et al., Thin endometrium in assisted reproductive technology. Curr Opin Obstet Gynecol. Jun. 2008;20(3):221-8. doi: 10.1097/GCO.0b013e328302143c.
Seppänen-Laakso et al., How to study lipidomes. J Mol Endocrinol. Mar. 2009;42(3):185-90. Epub Dec. 5, 2008.
Sergio et al., Prophylaxis of recurrent preeclampsia: low-molecular-weight heparin plus low-dose aspirin versus low-dose aspirin alone. Hypertens Pregnancy. 2006;25(2):115-27.
Shao et al., Crystallographic analysis of calcium-dependent heparin binding to annexin A2. J Biol Chem. Oct. 20, 2006;281(42):31689-95. Author manuscript.
Sher et al., Effect of vaginal sildenafil on the outcome of in vitro fertilization (IVF) after multiple IVF failures attributed to poor endometrial development. Fertil Steril. Nov. 2002;78(5):1073-6.
Shi et al., Acceleration of skeletal muscle regeneration in a rat skeletal muscle injury model by local injection of human peripheral blood-derived CD133-positive cells. Stem Cells. Apr. 2009;27(4):949-60. doi: 10.1002/stem.4.
Shmelkov et al., AC133/CD133/Prominin-1. Int J Biochem Cell Biol. Apr. 2005;37(4):715-9.
Simón et al., Coculture of human embryos with autologous human endometrial epithelial cells in patients with implantation failure. J Clin Endocrinol Metab. Aug. 1999;84(8):2638-46.
Singh et al., Autologous stem cell transplantation in refractory Asherman's syndrome: A novel cell based therapy. J Hum Reprod Sci. Apr. 2014;7(2):93-8. doi: 10.4103/0974-1208.138864.
Singh et al., Levels of Prostaglandin F-2-Alpha and Prostaglandin E-2 in human endometrium during the menstrual cycle. Am. J. Obstet. Gynecol. Apr. 21, 1975;121(7):1003-1007.
Sobel, Fibrinolysis and activators of plasminogen. Heart Lung. Nov. 1987;16(6 Pt 2):775-9. Abstract Only.
Steegers et al., Pre-eclampsia. Lancet. Aug. 21, 2010;376(9741):631-44. doi: 10.1016/S0140-6736(10)60279-6. Abstract Only.
Strowitzki et al., The human endometrium as a fertility-determining factor. Hum Reprod Update. Sep.-Oct. 2006;12(5):617-30. Epub Jul. 10, 2006.
Sucak et al., Increased global fibrinolytic capacity as a clue for activated fibrinolysis in pre-eclampsia. Blood Coagul Fibrinolysis. Jul. 2006;17(5):347-52. Abstract Only.

Surrenti et al., High performance liquid chromotographic method for prostaglandin E2 determination in human gastric juice without derivatization. J Liquid Chromatography and Rel Technol. Oct. 1984;7(12):2409-19.
Tabanelli et al., In vitro decidualization of human endometrial stromal cells. J Steroid Biochem Mol Biol. May 1992;42(3-4):337-44. Abstract Only.
Tackels-Horne et al., Identification of differentially expressed genes in hepatocellular carcinoma and metastatic liver tumors by oligonucleotide expression profiling. Cancer. Jul. 15, 2001;92(2):395-405.
Taylor, Endometrial cells derived from donor stem cells in bone marrow transplant recipients. JAMA. Jul. 7, 2004;292(1):81-5.
Thomas et al., Endometrial integrin expression in women undergoing in vitro fertilization and the association with subsequent treatment outcome. Fertil Steril. Sep. 2003;80(3):502-7.
Tsang et al., Prostaglandin secretion by human endometrium in vitro. American Journal of Obstetrics and Gynecology. 1982;142(6):626-633. Abstract only.
Tsapanos et al., The role of Seprafilm bioresorbable membrane in the prevention and therapy of endometrial synechiae. J Biomed Mater Res. 2002;63(1):10-4.
Uchida et al., Direct isolation of human central nervous system stem cells. Proc Natl Acad Sci U S A. Dec. 19, 2000;97(26):14720-5.
Urbich et al., Endothelial progenitor cells: characterization and role in vascular biology. Circ Res. Aug. 20, 2004;95(4):343-53.
Van Der Gaast et al., Endometrial secretion aspiration prior to embryo transfer does not reduce implantation rates. Reprod Biomed Online. Jul.-Aug. 2003;7(1):105-9.
Van Der Gaast et al., The feasibility of a less invasive method to assess endometrial maturation—comparison of simultaneously obtained uterine secretion and tissue biopsy. BJOG. Jan. 2009;116(2):304-12.
Vaquerizas et al., GEPAS, an experiment-oriented pipeline for the analysis of microarray gene expression data. Nucleic Acids Res. Jul. 1, 2005;33(Web Server issue):W616-20.
Ventolini et al., Hysteroscopy in the evaluation of patients with recurrent pregnancy loss: a cohort study in a primary care population. Surg Endosc. Dec. 2004;18(12):1782-4. Epub Oct. 26, 2004.
Vinnars et al., The severity of clinical manifestations in preeclampsia correlates with the amount of placental infarction. Acta Obstet Gynecol Scand. Jan. 2011;90(1):19-25. doi:10.1111/j.1600-0412.2010.01012.x. Abstract Only.
Voyksner et al., Determination of prostaglandins, and other metabolites of arachidonic acid by thermospray HPLC/MS using post column derivatization. Biomed Environ Mass Spectrom. May 1987;14(5):213-20.
Wang et al., Roadmap to embryo implantation: clues from mouse models. Nat Rev Genet. Mar. 2006;7(3):185-99.
Wasielak et al., Effect of the conceptus on uterine prostaglandin-F2alpha and prostaglandin-E2 release and synthesis during the periimplantation period in the pig. Reprod Fertil Dev. 2009;21(5):709-17.
Woclawek-Potocka et al., Phytoestrogen metabolites are much more active than phytoestrogens themselves in increasing prostaglandin F(2alpha) synthesis via prostaglanin F(2alpha) synthase-like 2 stimulation in bovine endometrium. Prostaglandins Other Lipid Mediat. Dec. 2005;78(1-4):202-17. Epub Oct. 27, 2005.
Wolff et al., Demonstration of multipotent stem cells in the adult human endometrium by in vitro chondrogenesis. Reprod Sci. Sep. 2007;14(6):524-33.
Xin et al., Alterations of profibrinolytic receptor annexin A2 in pre-eclampsia: a possible role in placental thrombin formation. Thromb Res. May 2012;129(5):563-7. doi: 10.1016/j.thromres.2011.07.039. Epub Aug. 24, 2011.
Zhang et al., Transcatheter Arterial Infusion of Autologous CD133+ Cells for Diabetic Peripheral Artery Disease. Stem Cells Int. 2016;2016:6925357. doi: 10.1155/2016/6925357. Epub Feb. 14, 2016.
Zhao et al., Uterine infusion with bone marrow mesenchymal stem cells improves endometrium thickness in a rat model of thin endometrium. Reprod Sci. Feb. 2015;22(2):181-8. doi: 10.1177/1933719114537715. Epub Jun. 19, 2014.

(56) References Cited

OTHER PUBLICATIONS

Zhou et al., Cigarette smoke inhibits recruitment of bone-marrow-derived stem cells to the uterus. Reprod Toxicol. Feb. 2011;31(2):123-7. doi: 10.1016/j.reprotox.2010.10.007. Epub Oct. 15, 2010. Author manuscript.

Zhou et al., Preeclampsia is associated with abnormal expression of adhesion molecules by invasive cytotrophoblasts. J Clin Invest. Mar. 1993;91(3):950-60.

Zhou et al., Preeclampsia is associated with failure of human cytotrophoblasts to mimic a vascular adhesion phenotype. One cause of defective endovascular invasion in this syndrome? J Clin Invest. May 1, 1997;99(9):2152-64.

Zhou et al., Reversal of gene dysregulation in cultured cytotrophoblasts reveals possible causes of preeclampsia. J Clin Invest. Jul. 2013;123(7):2862-72. doi: 10.1172/JCI66966. Erratum in: J Clin Invest. Oct. 1, 2013;123(10):4541.

* cited by examiner

FIG. 1A

| SEQ ID NO: | PROBE | GENE | SEQ ID NO: | PROBE | GENE | SEQ ID NO: | PROBE | GENE |
|---|---|---|---|---|---|---|---|---|
| 13 | A_23_P207507 | ABCC3 | 203 | A_01_P016340 | EFNA1 | 393 | A_23_P210428 | MYL9 |
| 14 | A_01_P004704 | ABLIM3 | 204 | A_23_P254512 | EFNA1 | 394 | A_23_P210425 | MYL9 |
| 15 | A_24_P123408 | ABLIM3 | 205 | A_23_P113005 | EFNA1 | 395 | A_01_P014392 | MYL9 |
| 16 | A_23_P266205 | ABLIM3 | 206 | A_23_P382065 | EMCN | 396 | A_24_P244800 | NDRG2 |
| 17 | A_23_P266204 | ABLIM3 | 207 | A_23_P333605 | ENPEP | 397 | A_23_P37205 | NDRG2 |
| 18 | A_24_P189516 | ACADSB | 208 | A_23_P144596 | ENPEP | 398 | A_23_P119042 | NKG7 |
| 19 | A_23_P158570 | ACADSB | 209 | A_23_P259220 | EPHB3 | 399 | A_01_P015240 | NNMT |
| 20 | A_32_P31945 | ACADSB | 210 | A_23_P95060 | EPHB3 | 400 | A_23_P127584 | NNMT |
| 21 | A_23_P150053 | ACTA2 | 211 | A_23_P167051 | EVC | 401 | A_23_P140256 | NP |
| 22 | A_01_P006531 | ACTA2 | 212 | A_24_P60441 | EVC | 402 | A_01_P012780 | NR4A2 |
| 23 | A_23_P342275 | ADAMTS1 | 213 | A_24_P370042 | FAM59A | 403 | A_23_P131207 | NR4A2 |
| 24 | A_23_P211039 | ADAMTS1 | 214 | A_23_P66948 | FAM59A | 404 | A_23_P131208 | NR4A2 |
| 25 | A_01_P013378 | ADAMTS1 | 215 | A_23_P136125 | FGB | 405 | A_23_P213695 | NRG2 |
| 26 | A_01_P016559 | ADAMTS8 | 216 | A_23_P114011 | FGB | 406 | A_01_P018499 | NRG2 |
| 27 | A_23_P86956 | ADAMTS8 | 217 | A_01_P018037 | FLJ10719 | 407 | A_01_P009356 | NRG2 |
| 28 | A_23_P138706 | ADRA2A | 218 | A_24_P266048 | FLJ20152 | 408 | A_23_P349857 | NRG2 |
| 29 | A_01_P002991 | ADRA2A | 219 | A_23_P167599 | FLJ20152 | 409 | A_23_P213699 | NRG2 |
| 30 | A_23_P31407 | AGR2 | 220 | A_01_P009941 | FOSL2 | 410 | A_24_P134653 | OFD1 |
| 31 | A_01_P005774 | ALPL | 221 | A_23_P218565 | FOSL2 | 411 | A_23_P254226 | OFD1 |
| 32 | A_23_P97043 | ALPL | 222 | A_23_P348121 | FOSL2 | 412 | A_01_P014581 | OFD1 |
| 33 | A_24_P353619 | ALPL | 223 | A_23_P218553 | FOSL2 | 413 | A_01_P010547 | OLFM1 |

FIG. 1B

| SEQ ID NO: | PROBE | GENE | SEQ ID NO: | PROBE | GENE | SEQ ID NO: | PROBE | GENE |
|---|---|---|---|---|---|---|---|---|
| 34 | A_23_P97046 | ALPL | 224 | A_23_P345581 | FOSL2 | 414 | A_23_P219161 | OLFM1 |
| 35 | A_23_P14083 | AMIGO2 | 225 | A_24_P196562 | FXYD2 | 415 | A_23_P304311 | OLFM1 |
| 36 | A_23_P428738 | ANG | 226 | A_23_P161769 | FXYD2 | 416 | A_24_P406601 | OLFM1 |
| 37 | A_01_P018201 | ANK3 | 227 | A_23_P74609 | G0S2 | 417 | A_24_P181254 | OLFM4 |
| 38 | A_23_P202269 | ANK3 | 228 | A_01_P004760 | G0S2 | 418 | A_23_P2789 | OLFM4 |
| 39 | A_23_P301530 | ANK3 | 229 | A_23_P162640 | L1 | 419 | A_23_P169061 | OPRK1 |
| 40 | A_24_P162173 | ANK3 | 230 | A_24_P4816 | L1 | 420 | A_32_P3576 | OPRK1 |
| 41 | A_01_P007944 | ANK3 | 231 | A_23_P65817 | L1 | 421 | A_32_P3572 | OPRK1 |
| 42 | A_32_P33304 | ANK3 | 232 | A_23_P23221 | GADD45A | 422 | A_01_P003195 | OPRK1 |
| 43 | A_32_P33309 | ANK3 | 233 | A_01_P005123 | GALNT12 | 423 | A_23_P257129 | PAEP |
| 44 | A_23_P16976 | ANXA4 | 234 | A_23_P257731 | GALNT12 | 424 | A_23_P397334 | PAQR4 |
| 45 | A_01_P009551 | AOX1 | 235 | A_23_P415652 | GALNT12 | 425 | A_23_P397341 | PAQR4 |
| 46 | A_23_P154037 | AOX1 | 236 | A_24_P942370 | GALNT4 | 426 | A_23_P66213 | PAQR4 |
| 47 | A_23_P112481 | AQP3 | 237 | A_01_P010093 | GALNT4 | 427 | A_23_P66211 | PAQR4 |
| 48 | A_23_P112482 | AQP3 | 238 | A_23_P413576 | GALNT4 | 428 | A_32_P62997 | PBK |
| 49 | A_23_P128728 | ARG2 | 239 | A_23_P116922 | GALNT4 | 429 | A_23_P82699 | PBK |
| 50 | A_23_P151075 | ARHGDIB | 240 | A_01_P005076 | GAS1 | 430 | A_23_P156852 | PECI |
| 51 | A_01_P018222 | ARHGDIB | 241 | A_23_P83134 | GAS1 | 431 | A_23_P254584 | PENK |
| 52 | A_23_P97871 | ARID5B | 242 | A_23_P159190 | GAS1 | 432 | A_23_P417918 | PENK |
| 53 | A_01_P007755 | ARID5B | 243 | A_23_P159191 | GAS1 | 433 | A_01_P015221 | PENK |
| 54 | A_32_P18440 | ARID5B | 244 | A_01_P012911 | GBP2 | 434 | A_23_P29816 | PLA1A |

FIG. 1C

| SEQ ID NO: | PROBE | GENE | SEQ ID NO: | PROBE | GENE | SEQ ID NO: | PROBE | GENE |
|---|---|---|---|---|---|---|---|---|
| 55 | A_24_P170667 | ARID5B | 245 | A_23_P85693 | GBP2 | 435 | A_24_P294408 | PLA1A |
| 56 | A_24_P944437 | ARID5B | 246 | A_23_P16523 | GDF15 | 436 | A_23_P127367 | POLD4 |
| 57 | A_01_P007754 | ARID5B | 247 | A_01_P016695 | GDF15 | 437 | A_01_P004358 | POLD4 |
| 58 | A_23_P52017 | ASPM | 248 | A_24_P390096 | GLIPR1 | 438 | A_23_P360215 | POLD4 |
| 59 | A_32_P231556 | ASPM | 249 | A_23_P364024 | GLIPR1 | 439 | A_24_P347411 | POSTN |
| 60 | A_24_P911179 | ASPM | 250 | A_23_P209954 | GNLY | 440 | A_23_P205111 | POSTN |
| 61 | A_01_P018684 | ASPM | 251 | A_24_P932547 | GPR64 | 441 | A_23_P18443 | PPARGC1A |
| 62 | A_01_P018905 | ASS1 | 252 | A_01_P016209 | GPR64 | 442 | A_24_P303052 | PPARGC1A |
| 63 | A_23_P31922 | ASS1 | 253 | A_23_P253692 | GPR64 | 443 | A_23_P18447 | PPARGC1A |
| 64 | A_23_P31921 | ASS1 | 254 | A_23_P253695 | GPR64 | 444 | A_01_P016440 | PPARGC1A |
| 65 | A_32_P13102 | ASS1 | 255 | A_32_P109029 | GPRC5C | 445 | A_23_P206059 | PRC1 |
| 66 | A_01_P014301 | ATP1B1 | 256 | A_32_P544510 | GPRC5C | 446 | A_23_P1374 | PRKCQ |
| 67 | A_23_P146943 | ATP1B1 | 257 | A_23_P38167 | GPRC5C | 447 | A_23_P258463 | PROM1 |
| 68 | A_23_P62932 | ATP1B1 | 258 | A_23_P346673 | GPRC5C | 448 | A_01_P010711 | PROM1 |
| 69 | A_01_P010458 | ATP1B1 | 259 | A_23_P346670 | GPRC5C | 449 | A_23_P258462 | PROM1 |
| 70 | A_23_P61960 | ATP6V0E2L | 260 | A_01_P006986 | GPRC5C | 450 | A_24_P119141 | PROS1 |
| 71 | A_23_P61956 | ATP6V0E2L | 261 | A_23_P133474 | GPX3 | 451 | A_23_P73114 | PROS1 |
| 72 | A_24_P396994 | ATP6V1A | 262 | A_23_P133475 | GPX3 | 452 | A_32_P500684 | PROS1 |
| 73 | A_23_P211965 | ATP6V1A | 263 | A_23_P329821 | GREM2 | 453 | A_23_P84510 | PROS1 |
| 74 | A_01_P010392 | ATP6V1A | 264 | A_23_P329822 | GREM2 | 454 | A_24_P383480 | PROS1 |
| 75 | A_23_P67771 | BARD1 | 265 | A_24_P40626 | GREM2 | 455 | A_23_P140805 | PSMB10 |

FIG. 1D

| SEQ ID NO: | PROBE | GENE | SEQ ID NO: | PROBE | GENE | SEQ ID NO: | PROBE | GENE |
|---|---|---|---|---|---|---|---|---|
| 76 | A_01_P005782 | BARD1 | 266 | A_23_P97181 | GREM2 | 456 | A_23_P140807 | PSMB10 |
| 77 | A_23_P57856 | BCL6 | 267 | A_01_P017852 | GREM2 | 457 | A_23_P151710 | PTGER2 |
| 78 | A_01_P001583 | BCL6 | 268 | A_23_P133445 | GZMA | 458 | A_01_P012436 | PTGER2 |
| 79 | A_01_P001085 | BIRC3 | 269 | A_01_P014820 | HABP2 | 459 | A_23_P47924 | PTPRR |
| 80 | A_23_P98350 | BIRC3 | 270 | A_23_P1173 | HABP2 | 460 | A_32_P770346 | PTPRR |
| 81 | A_01_P000082 | BUB1B | 271 | A_23_P61643 | HAL | 461 | A_32_P461885 | PTPRR |
| 82 | A_23_P163481 | BUB1B | 272 | A_23_P61637 | HAL | 462 | A_32_P480310 | PTPRR |
| 83 | A_24_P329795 | C10orf10 | 273 | A_01_P003831 | HAL | 463 | A_01_P017426 | RAD54B |
| 84 | A_23_P35597 | C10orf10 | 274 | A_32_P502420 | HAL | 464 | A_23_P82738 | RAD54B |
| 85 | A_23_P35595 | C10orf10 | 275 | A_23_P7154 | HAND2 | 465 | A_23_P94141 | RAD54B |
| 86 | A_01_P003476 | C10orf3 | 276 | A_23_P373521 | HAND2 | 466 | A_23_P58819 | RANBP17 |
| 87 | A_01_P012231 | C11orf8 | 277 | A_23_P157659 | HEY1 | 467 | A_01_P013828 | RANBP17 |
| 88 | A_23_P77041 | C14orf161 | 278 | A_01_P001077 | HEY1 | 468 | A_23_P18078 | RARRES1 |
| 89 | A_23_P77043 | C14orf161 | 279 | A_32_P83845 | HEY1 | 469 | A_23_P1962 | RARRES3 |
| 90 | A_01_P000840 | C3 | 280 | A_01_P012352 | HEY2 | 470 | A_23_P166087 | RASSF2 |
| 91 | A_23_P101407 | C3 | 281 | A_23_P168351 | HEY2 | 471 | A_23_P205531 | ARNSE4 |
| 92 | A_23_P101400 | C3 | 282 | A_24_P363408 | HEY2 | 472 | A_01_P017372 | ARNSE4 |
| 93 | A_01_P000020 | C4,4[a] | 283 | A_23_P168354 | HEY2 | 473 | A_01_P017520 | RPRM |
| 94 | A_01_P005981 | C4BPA | 284 | A_32_P477383 | HLA-DOB | 474 | A_23_P5370 | RPRM |
| 95 | A_23_P97541 | C4BPA | 285 | A_24_P911783 | HLA-DOB | 475 | A_23_P5365 | RPRM |
| 96 | A_23_P21092 | CALB2 | 286 | A_23_P30736 | HLA-DOB | 476 | A_01_P012092 | RRAS |

FIG. 1E

| SEQ ID NO: | PROBE | GENE | SEQ ID NO: | PROBE | GENE | SEQ ID NO: | PROBE | GENE |
|---|---|---|---|---|---|---|---|---|
| 97 | A_23_P217570 | CAPN6 | 287 | A_32_P343332 | HLA-DOB | 477 | A_23_P39076 | RRAS |
| 98 | A_01_P018103 | CAPN6 | 288 | A_01_P015398 | HLA-DOB | 478 | A_23_P39074 | RRAS |
| 99 | A_23_P40453 | CBR3 | 289 | A_23_P374053 | HMHA1 | 479 | A_23_P383227 | S100A1 |
| 100 | A_24_P934477 | CBR3 | 290 | A_24_P71904 | HPGD | 480 | A_23_P94800 | S100A4 |
| 101 | A_23_P40445 | CBR3 | 291 | A_23_P213050 | HPGD | 481 | A_32_P900698 | S100A4 |
| 102 | A_32_P72822 | CCNB2 | 292 | A_01_P012816 | HPGD | 482 | A_23_P58266 | S100P |
| 103 | A_23_P65757 | CCNB2 | 293 | A_23_P256107 | HPSE | 483 | A_23_P161940 | SCGB2A2 |
| 104 | A_01_P000086 | CCNB2 | 294 | A_23_P116414 | HRASLS3 | 484 | A_01_P016031 | SCGB2A2 |
| 105 | A_23_P118862 | CD7 | 295 | A_23_P14986 | HSD11B2 | 485 | A_01_P002141 | SCYE1 |
| 106 | A_01_P019708 | CD7 | 296 | A_23_P59375 | ID4 | 486 | A_23_P121686 | SCYE1 |
| 107 | A_23_P431815 | CD7 | 297 | A_32_P45009 | IDH1 | 487 | A_23_P205355 | SERPINA6 |
| 108 | A_01_P001621 | CDA | 298 | A_23_P5376 | IDH1 | 488 | A_24_P321766 | SERPINA6 |
| 109 | A_23_P34597 | CDA | 299 | A_01_P006229 | IDH1 | 489 | A_23_P139114 | SERPING1 |
| 110 | A_23_P138507 | CDC2 | 300 | A_01_P015343 | IER3 | 490 | A_23_P139123 | SERPING1 |
| 111 | A_01_P011602 | CDC2 | 301 | A_23_P42257 | IER3 | 491 | A_23_P215328 | SFRP4 |
| 112 | A_23_P149195 | CDC20 | 302 | A_01_P000583 | IER3 | 492 | A_24_P8165 | SLC15A1 |
| 113 | A_01_P005979 | CDC20 | 303 | A_32_P419552 | IER3 | 493 | A_23_P128609 | SLC15A1 |
| 114 | A_23_P149200 | CDC20 | 304 | A_23_P203458 | IGF2 | 494 | A_23_P92107 | SLC15A2 |
| 115 | A_23_P253524 | CENPE | 305 | A_23_P421379 | IGF2 | 495 | A_01_P004018 | SLC15A2 |
| 116 | A_01_P006340 | CENPE | 306 | A_23_P150609 | IGF2 | 496 | A_23_P152791 | SLC16A6 |
| 117 | A_23_P206733 | CES1 | 307 | A_23_P42869 | IGFBP1 | 497 | A_01_P007822 | SLC16A6 |

FIG. 1F

| SEQ ID NO: | PROBE | GENE | SEQ ID NO: | PROBE | GENE | SEQ ID NO: | PROBE | GENE |
|---|---|---|---|---|---|---|---|---|
| 118 | A_32_P540234 | CFD/DF | 308 | A_23_P42868 | IGFBP1 | 498 | A_24_P731648 | SLC16A6 |
| 119 | A_23_P25674 | CKB | 309 | A_01_P002590 | IGFBP1 | 499 | A_01_P003853 | SLC1A1 |
| 120 | A_24_P61537 | CKB | 310 | A_23_P29953 | IL15 | 500 | A_23_P216468 | SLC1A1 |
| 121 | A_01_P017811 | CKB | 311 | A_24_P203000 | IL2RB | 501 | A_24_P232252 | SLC1A1 |
| 122 | A_01_P007324 | CLDN10 | 312 | A_01_P020028 | IL2RB | 502 | A_23_P363399 | SLC38A1 |
| 123 | A_23_P48350 | CLDN10 | 313 | A_23_P255430 | IL2RB | 503 | A_01_P001379 | SLC38A1 |
| 124 | A_23_P19944 | CLDN4 | 314 | A_01_P011439 | IMPA2 | 504 | A_23_P117242 | SLC7A1 |
| 125 | A_24_P115183 | CLDN4 | 315 | A_23_P50081 | IMPA2 | 505 | A_24_P253251 | SLC7A1 |
| 126 | A_01_P000670 | CLDN4 | 316 | A_23_P112026 | INDO | 506 | A_23_P91230 | SLPI |
| 127 | A_23_P215918 | CLU | 317 | A_01_P006886 | KCNG1 | 507 | A_01_P005468 | SLPI |
| 128 | A_23_P215913 | CLU | 318 | A_23_P210581 | KCNG1 | 508 | A_24_P190472 | SLPI |
| 129 | A_23_P313623 | COBL | 319 | A_24_P237117 | KCNG1 | 509 | A_23_P8513 | SNX10 |
| 130 | A_32_P86173 | COBL | 320 | A_23_P210580 | KCNG1 | 510 | A_24_P98109 | SNX10 |
| 131 | A_01_P003861 | COL16A1 | 321 | A_01_P002764 | KCNG1 | 511 | A_24_P935819 | SOD2 |
| 132 | A_23_P160318 | COL16A1 | 322 | A_23_P329261 | KCNJ2 | 512 | A_23_P134176 | SOD2 |
| 133 | A_24_P264943 | COMP | 323 | A_23_P55219 | KCNJ2 | 513 | A_32_P89691 | SORD |
| 134 | A_23_P90436 | COMP | 324 | A_23_P86874 | KCNK7 | 514 | A_32_P85311 | SORD |
| 135 | A_23_P106761 | CORO1A | 325 | A_01_P003027 | KCNK7 | 515 | A_32_P127153 | SORD |
| 136 | A_23_P83620 | COTL1 | 326 | A_01_P016715 | KHDRBS3 | 516 | A_23_P77103 | SORD |
| 137 | A_24_P416131 | COTL1 | 327 | A_23_P257335 | KHDRBS3 | 517 | A_01_P000174 | SORD |
| 138 | A_32_P158385 | COTL1 | 328 | A_01_P004436 | KIAA0802 | 518 | A_23_P82775 | SOX17 |

FIG. 1G

| SEQ ID NO: | PROBE | GENE | SEQ ID NO: | PROBE | GENE | SEQ ID NO: | PROBE | GENE |
|---|---|---|---|---|---|---|---|---|
| 139 | A_23_P3866 | COTL1 | 329 | A_32_P38763 | KIAA0802 | 519 | A_01_P001801 | SOX17 |
| 140 | A_23_P83624 | COTL1 | 330 | A_23_P360605 | KIAA0802 | 520 | A_24_P46946 | SOX17 |
| 141 | A_01_P014841 | CP | 331 | A_01_P007808 | KIAA0888 | 521 | A_23_P111194 | SPDEF |
| 142 | A_23_P414793 | CP | 332 | A_01_P007810 | KIAA0888 | 522 | A_23_P7313 | SPP1 |
| 143 | A_23_P423074 | KIAA0888 | 333 | A_24_P227091 | KIF11 | 523 | A_01_P017618 | SPP1 |
| 144 | A_32_P84242 | KIAA0888 | 334 | A_23_P52278 | KIF11 | 524 | A_32_P527817 | STAR |
| 145 | A_32_P84241 | KIAA0888 | 335 | A_23_P266956 | KIF20A | 525 | A_23_P8981 | STAR |
| 146 | A_23_P405064 | CRABP2 | 336 | A_23_P148475 | KIF4A | 526 | A_24_P351906 | STEAP4 |
| 147 | A_01_P005286 | CRABP2 | 337 | A_23_P151046 | KLRC1 | 527 | A_23_P255231 | STEAP4 |
| 148 | A_23_P115064 | CRABP2 | 338 | A_23_P139654 | KLRC1 | 528 | A_32_P109727 | SYNE2 |
| 149 | A_01_P003175 | CREB3L1 | 339 | A_24_P387926 | KMO | 529 | A_23_P205553 | SYNE2 |
| 150 | A_23_P150407 | CREB3L1 | 340 | A_23_P200838 | KMO | 530 | A_23_P128887 | SYNE2 |
| 151 | A_23_P419760 | CRISP3 | 341 | A_24_P77082 | KMO | 531 | A_23_P140277 | SYNE2 |
| 152 | A_01_P010473 | CSRP2 | 342 | A_23_P50108 | KNTC2 | 532 | A_24_P68311 | SYNE2 |
| 153 | A_23_P44724 | CSRP2 | 343 | A_01_P010921 | KNTC2 | 533 | A_24_P307759 | SYNE2 |
| 154 | A_24_P33477 | CTNNA2 | 344 | A_24_P14156 | KNTC2 | 534 | A_23_P212844 | TACC3 |
| 155 | A_32_P14986 | CTNNA2 | 345 | A_23_P313591 | KRT7 | 535 | A_01_P002824 | TAGLN |
| 156 | A_23_P84736 | CTNNA2 | 346 | A_23_P381945 | KRT7 | 536 | A_23_P87011 | TAGLN |
| 157 | A_24_P396167 | CTSW | 347 | A_23_P86012 | LAMB3 | 537 | A_23_P87013 | TAGLN |
| 158 | A_23_P13031 | CTSW | 348 | A_01_P018078 | LEPREL1 | 538 | A_23_P123662 | TBC1D2 |
| 159 | A_23_P13027 | CTSW | 349 | A_23_P69179 | LEPREL1 | 539 | A_23_P123666 | TBC1D2 |

FIG. 1H

| SEQ ID NO: | PROBE | GENE | SEQ ID NO: | PROBE | GENE | SEQ ID NO: | PROBE | GENE |
|---|---|---|---|---|---|---|---|---|
| 160 | A_23_P121692 | CXCL13 | 350 | A_24_P122137 | LIF | 540 | A_23_P64372 | TCN1 |
| 161 | A_01_P003023 | CXCL13 | 351 | A_24_P233488 | LIF | 541 | A_01_P009817 | TH |
| 162 | A_23_P121695 | CXCL13 | 352 | A_23_P155017 | LIF | 542 | A_24_P924602 | TH |
| 163 | A_01_P019786 | CXCL14 | 353 | A_01_P019499 | LMCD1 | 543 | A_23_P258633 | TH |
| 164 | A_23_P213745 | CXCL14 | 354 | A_23_P6771 | LMCD1 | 544 | A_23_P95891 | TH |
| 165 | A_24_P345451 | CYBRD1 | 355 | A_01_P000575 | LMOD1 | 545 | A_01_P013083 | THBD |
| 166 | A_01_P005800 | CYBRD1 | 356 | A_23_P201940 | LMOD1 | 546 | A_23_P91390 | THBD |
| 167 | A_23_P209564 | CYBRD1 | 357 | A_23_P63980 | LRFN4 | 547 | A_32_P192334 | THBD |
| 168 | A_23_P103486 | CYP2J2 | 358 | A_01_P007807 | LRFN4 | 548 | A_23_P253652 | THBS2 |
| 169 | A_24_P916916 | CYP3A5 | 359 | A_24_P403561 | LRP4 | 549 | A_23_P62021 | THBS2 |
| 170 | A_23_P8807 | CYP3A5 | 360 | A_23_P159349 | LRP4 | 550 | A_24_P605612 | THBS2 |
| 171 | A_23_P8801 | CYP3A5 | 361 | A_23_P215024 | LRRC1 | 551 | A_23_P399078 | TIMP3 |
| 172 | A_32_P153423 | DDX52 | 362 | A_01_P020198 | LRRC1 | 552 | A_01_P005541 | TIMP3 |
| 173 | A_23_P118660 | DDX52 | 363 | A_01_P016431 | LRRC1 | 553 | A_01_P014722 | TMEM16A |
| 174 | A_24_P1929 | DDX52 | 364 | A_23_P253958 | LRRC17 | 554 | A_24_P87036 | TMEM16A |
| 175 | A_01_P010027 | DEFB1 | 365 | A_23_P83857 | MAOA | 555 | A_24_P110831 | TMEM16A |
| 176 | A_23_P71480 | DEFB1 | 366 | A_23_P96410 | MAOA | 556 | A_23_P98304 | TMEM16A |
| 177 | A_23_P60166 | DEPDC6 | 367 | A_01_P016743 | MAP2K6 | 557 | A_01_P015348 | TMEPAI |
| 178 | A_01_P001685 | CFD/DF | 368 | A_23_P207445 | MAP2K6 | 558 | A_24_P413126 | TMEPAI |
| 179 | A_01_P000551 | DFNB31 | 369 | A_23_P1021 | MFAP2 | 559 | A_23_P57089 | TMEPAI |
| 180 | A_24_P376129 | DFNB31 | 370 | A_23_P1029 | MFAP2 | 560 | A_23_P137173 | TMSL8 |

FIG. 1I

| SEQ ID NO: | PROBE | GENE | SEQ ID NO: | PROBE | GENE | SEQ ID NO: | PROBE | GENE |
|---|---|---|---|---|---|---|---|---|
| 181 | A_23_P83351 | DFNB31 | 371 | A_23_P87700 | MFAP5 | 561 | A_23_P137179 | TMSL8 |
| 182 | A_23_P33759 | DHRS3 | 372 | A_01_P003020 | MFAP5 | 562 | A_23_P118834 | TOP2A |
| 183 | A_23_P24129 | DKK1 | 373 | A_01_P013777 | MGC11242 | 563 | A_23_P106061 | TRA@ |
| 184 | A_23_P88331 | DLG7 | 374 | A_23_P2052 | MMP26 | 564 | A_23_P258504 | TRA@ |
| 185 | A_24_P97104 | DPP4 | 375 | A_23_P135104 | MRPS2 | 565 | A_32_P806170 | TRA@ |
| 186 | A_23_P39885 | DPP4 | 376 | A_23_P110430 | MSX1 | 566 | A_23_P44857 | TRA@ |
| 187 | A_01_P008447 | DPP4 | 377 | A_01_P001372 | MSX1 | 567 | A_23_P258798 | TRA@ |
| 188 | A_23_P54291 | DUOX1 | 378 | A_24_P345837 | MSX1 | 568 | A_23_P132760 | TRH |
| 189 | A_24_P316586 | DUOX1 | 379 | A_23_P60933 | MT1G | 569 | A_01_P011590 | TRH |
| 190 | A_23_P160559 | ECM1 | 380 | A_23_P206707 | MT1G | 570 | A_23_P36531 | TSPAN8 |
| 191 | A_01_P019449 | ECM1 | 381 | A_23_P206701 | MT1G | 571 | A_23_P36528 | TTC21B |
| 192 | A_23_P149180 | ECM1 | 382 | A_23_P414343 | MT1H | 572 | A_23_P5422 | TTC21B |
| 193 | A_01_P007491 | EDN3 | 383 | A_23_P106844 | MT2A | 573 | A_24_P111511 | VCAM1 |
| 194 | A_01_P017090 | EDN3 | 384 | A_24_P361896 | MT2A | 574 | A_23_P34345 | XCL1 |
| 195 | A_01_P013980 | EDN3 | 385 | A_32_P306874 | MUC16 | 575 | A_23_P200752 | XCL1 |
| 196 | A_23_P17438 | EDN3 | 386 | A_32_P889536 | MUC16 | 576 | A_24_P45476 | XCL1 |
| 197 | A_01_P010992 | EDNRB | 387 | A_32_P307960 | MUC16 | 577 | A_01_P019136 | XCL1 |
| 198 | A_23_P2831 | EDNRB | 388 | A_32_P393950 | MUC16 | 578 | A_23_P321431 | XCL2 |
| 199 | A_24_P330263 | EDNRB | 389 | A_32_P309031 | MUC16 | 579 | A_01_P017396 | XCL2 |
| 200 | A_01_P015376 | EDNRB | 390 | A_32_P424560 | MUC16 | 580 | A_23_P51534 | XCL2 |
| 201 | A_23_P501007 | EFEMP1 | 391 | A_32_P378729 | MUC16 | 581 | A_23_P51532 | XCL2 |

FIG. 1J

| SEQ ID NO: | PROBE | GENE | SEQ ID NO: | PROBE | GENE | SEQ ID NO: | PROBE | GENE |
|---|---|---|---|---|---|---|---|---|
| 202 | A_01_P017336 | EFEMP1 | 392 | A_23_P5211 | MUC16 | | | |

FIG. 2A

| GENE | FDR | FC | Description |
|---|---|---|---|
| TRH | 0.0000 | -21.69 | Homo sapiens thyrotropin-releasing hormone (TRH), ARNm [NM_007117] |
| HLA-008 | 0.0000 | -11.06 | Homo sapiens major histocompatibility complex, class II, DO beta (HLA-DOB), ARNm [NM_002120] |
| ATP6V0E2 | 0.0000 | -9.82 | Homo sapiens ATPase, H+ transporting V0 subunit e2 (ATP6V0E2), ARNm [NM_145230] |
| CSRP2 | 0.0000 | -9.62 | Homo sapiens cysteine and· glycine-rich protein 2 (CSRP2), ARNm [NM_001321] |
| OLFM4 | 0.0026 | -9.35 | Homo sapiens olfactomedin 4 (OLFM4), ARNm [NM_006418] |
| SLC15A2 | 0.0000 | -8.44 | Homo sapiens solute carrier family 15 (H+/peptide transporter), member 2 (SLC15A2), ARNm [NM_021082] |
| CALB2 | 0.0000 | -8.40 | Homo sapiens calbindin 2, 29kDa (calretinin) (CALB2), transcript variant CALB2, ARNm [NM_001740] |
| SFRP4 | 0.0009 | -8.33 | Homo sapiens SEQreted frizzled-related protein 4 (SFRP4), ARNm [NM_003014] |
| CTNNA2 | 0.0007 | -8.02 | Homo sapiens catenin (cadherin-associated protein), alpha 2 (CTNNA2), ARNm [NM_004389] |
| NR4A2 | 0.0006 | -7.05 | Homo sapiens nuclear receptor subfamily 4, group A, member 2 (NR4A2), transcript variant 1, ARNm [NM_006186] |
| DUOX1 | 0.0267 | -6.61 | Homo sapiens dual oxidase 1 (DUOX1), transcript variant 1, ARNm [NM_017434] |
| KIF20A | 0.0048 | -6.33 | Homo sapiens kinesin family member 20A (KIF20A), ARNm [NM_005733] |
| PENK | 0.0192 | -6.16 | Homo sapiens proenkephalin (PENK), ARNm [NM_006211] |
| POSTN | 0.0010 | -6.04 | Homo sapiens periostin, osteoblast specific factor (POSTN), ARNm [NM_006475] |
| LRP4 | 0.0000 | -5.87 | Homo sapiens low density lipoprotein receptor- related protein 4 (LRP4), ARNm [NM_002334] |
| SLC16A6 | 0.0376 | -5.61 | Homo sapiens solute carrier family 16 (monocarboxylic acid transporters), member 6 (SLC16A6), ARNm. [NM_004694] |
| GPR64 | 0.0005 | -5.52 | Homo sapiens G protein-coupled receptor 64 (GPR64), ARNm [NM_005756] |

FIG. 2B

| GENE | FDR | FC | Description |
|---|---|---|---|
| RANBP17 | 0.0002 | -5.50 | Homo sapiens RAN binding protein 17 (RANBP17), ARNm [NM_022897] |
| EDN3 | 0.0000 | -5.30 | Homo sapiens endothelin 3 (EDN3), transcript variant 3, ARNm. [NM_207033] |
| C10orf3 | 0.0185 | -5.24 | Homo sapiens chromosome 10 open reading frame 3 (C10orf3), ARNm [NM_018131] |
| CENPE | 0.0102 | -5.20 | Homo sapiens centromere protein E, 312kDa (CENPE), ARNm [NM_001813] |
| KIAA0888 | 0.0001 | -5.17 | PREDICTED: Homo sapiens KIAA0888 protein (KIAA0888), ARNm [XM_032571] |
| COL16A1 | 0.0002 | -4.89 | Homo sapiens collagen, type XVI, alpha 1 (COL 16A1), ARNm [NM_001856] |
| GALNT12 | 0.0000 | -4.85 | Homo sapiens UDP-N-acetyl-alpha-D-galactosamine:polypeptide N-acetylgalactosaminyltransferase 12 (GalNAc-T12) (GALNT12), ARNm [NM_024642] |
| ANK3 | 0.0000 | -4.79 | Homo sapiens ankyrin 3, node of Ranvier (ankyrin G) (ANK3), transcript variant 1, ARNm [NM_020987] |
| CAPN6 | 0.0003 | -4.76 | Homo sapiens calpain 6 (CAPN6), ARNm [NM_014289] |
| HPGD | 0.0002 | -4.72 | Homo sapiens hydroxyprostaglandin dehydrogenase 15-(NAD) (HPGD), ARNm [NM_000860] |
| SLC7A1 | 0.0000 | -4.72 | Homo sapiens solute carrier family 7 (cationic amino acid transporter, y+ system), member 1 (SLC7A1), ARNm [NM_003045] |
| MMP26 | 0.0143 | -4.66 | Homo sapiens matriz metallopeptidase 26 (MMP26), ARNm [NM_021801] |
| LRRC17 | 0.0000 | -4.64 | Homo sapiens leucine rich repeat containing 17 (LRRC17), transcript variant 2, ARNm [NM_005824] |
| KCNG1 | 0.0000 | -4.63 | Homo sapiens potassium voltage-gated channel, subfamily G, member 1 (KCNG1), transcript variant 1, ARNm [NM_002237] |
| CYP2J2 | 0.0001 | -4.54 | Homo sapiens cytochrome P450, family 2, subfamily J, polypeptide 2 (CYP2J2), ARNm [NM_000775] |
| MFAP2 | 0.0007 | -4.48 | Homo sapiens microfibrillar-associated protein 2 (MFAP2), transcript variant 1, ARNm [NM_017459] |
| ALPL | 0.0000 | -4.44 | Homo sapiens alkaline phosphatase, liver/bone/kidney (ALPL), ARNm [NM_000478] |

FIG. 2C

| GENE | FDR | FC | Description |
|---|---|---|---|
| CDC20 | 0.0065 | -4.39 | Homo sapiens CDC20 cell division cycle 20 homolog (S. cerevisiae) (CDC20), ARNm [NM_001255] |
| GREM2 | 0.0000 | -4.30 | Homo sapiens gremlin 2 homolog, cysteine knot superfamily (Xenopus laevis) (GREM2), ARNm [NM_022469] |
| SOX17 | 0.0000 | -4.24 | Homo sapiens SRY (sex determining region Y)- box 17 (SOX17), ARNm [NM_022454] |
| TACC3 | 0.0071 | -4.08 | Homo sapiens transforming, acidic coiled-coil containing protein 3 (TACC3), ARNm [NM_006342] |
| HEY2 | 0.0000 | -4.07 | Homo sapiens hairy/enhancer-of-split related· with YRPW motif 2 (HEY2), ARNm [NM_012259] |
| PAQR4 | 0.0000 | -4.06 | Homo sapiens progestin and adipoQ receptor family member IV (PAQR4), ARNrn [NM_152341] |
| MGC11242 | 0.0000 | -4.03 | Homo sapiens hypothetical protein MGC11242 (MGC11242), ARNm [NM_024320] |
| HSD11B2 | 0.0001 | -4.03 | Homo sapiens hydroxysteroid (11-beta) dehydrogenase 2 (HSD1182), ARNm [NM_000196] |
| KIF11 | 0.0044 | -4.01 | Homo sapiens kinesin family member 11 (KIF11), ARNm [NM_004523] |
| NRG2 | 0.0005 | -4.00 | Homo sapiens neuregulin 2 (NRG2), transcript variant 5, ARNm [NM_013984] |
| OLFM1 . | 0.0001 | -3.99 | Homo sapiens olfactomedin 1 (OLFM1), transcript variant 3, ARNm [NM_058199] |
| COBL | 0.0019 | -3.99 | Homo sapiens cordon-bleu homolog (mouse) (COBL), ARNm [NM_015198] |
| TOP2A | 0.0036 | -3.98 | Homo sapiens topoisomerase (AON) II alpha 170kDa (TOP2A), ARNm [NM_001067] |
| KNTC2 | 0.0126 | -3.88 | Homo sapiens kinetochore associated 2 (KNTC2), ARNm [NM_006101] |

FIG. 2D

| GENE | FDR | FC | Description |
|---|---|---|---|
| KIAA0802 | 0.0014 | -3.85 | Homo sapiens KIAA0802 (KIAA0802), ARNm [NM_015210] |
| SERPINA5 | 0.0287 | -3.84 | Homo sapiens serpin peptidase inhibitor, clade A (alpha-1 antiproteinase, antitrypsin), member 5 (SERPINA5), ARNm [NM_000624] |
| DLG7 | 0.0014 | -3.84 | Homo sapiens discs, large homolog 7 (Drosophila) (DLG7), ARNm [NM_014750] |
| ASPM | 0.0062 | -3.79 | Homo sapiens asp (abnormal spindle)-like, microcephaly associated (Drosophila) (ASPM), ARNm [NM_018136] |
| SPDEF | 0.0000 | -3.78 | Homo sapiens SAM pointed domain containing ets transcription factor (SPDEF), ARNm [NM_012391] |
| KMO | 0.0067 | -3.78 | Homo sapiens kynurenine 3-monooxygenase (kynurenine 3-hydroxylase) (KMO), ARNm [NM_003679] |
| CREB3L1 | 0.0001 | -3.77 | Homo sapiens cAMP responsive element binding protein 3-like 1 (CREB3L1), ARNm. [NM_052854] |
| ATP1B1 | 0.0000 | -3.73 | Homo sapiens ATPase, Na+/K+ transporting, beta 1 polypeptide (ATP1B1), ARNm [NM_001677] |
| PECI | 0.0000 | -3.71 | Homo sapiens peroxisomal D3,D2-enoyl-CoA isomerase (PECI), transcript variant 2, ARNm [NM_206836] |
| IDH1 | 0.0000 | -3.68 | Homo sapiens isocitrate dehydrogenase 1 (NADP+), soluble (IDH1), ARNm [NM_005896] |
| CBR3 | 0.0032 | -3.66 | Homo sapiens carbonyl reductase 3 (CBR3), ARNm [NM_001236] |
| C11orf8 | 0.0000 | -3.65 | Homo sapiens chromosome 11 open reading frame 8 (C11orf8), ARNm [NM_001584] |
| CKB | 0.0000 | -3.61 | Homo sapiens creatine kinase, brain (CKB), ARNm [NM_001823] |

FIG. 2E

| GENE | FDR | FC | Description |
|---|---|---|---|
| ADAMTS8 | 0.0104 | -3.59 | Homo sapiens a disintegrin-like and metalloprotease (reprolysin type) with thrombospondin type 1 motif, 8 (ADAMTS8), ARNm [NM_007037] |
| BIRC3 | 0.0261 | -3.58 | Homo sapiens baculoviral IAP repeat-containing 3 (BIRC3), transcript variant 1, ARNm [NM_001165] |
| DFNB31 | 0.0082 | -3.54 | Homo sapiens deafness, autosomal recessive 31 (DFNB31), ARNm [NM_015404] |
| KHDRBS3 | 0.0133 | -3.51 | Homo sapiens KH domain containing, ARN binding, signal transduction associated 3 (KHDRBS3), ARNm [NM_006558] |
| GALNT4 | 0.0240 | -3.50 | Homo sapiens UDP-N-acetyl-alpha-D-galactosamine:polypeptide N-acetylgalactosaminyltransferase 4 (GalNAc-T4) (GALNT4), ARNm [NM_003774] |
| TMEPAI | 0.0237 | -3.50 | Homo sapiens transmembrane, prostate androgen induced ARN (TMEPAI), transcript variant 1, ARNm [NM_020182] |
| KIF4A | 0.0030 | -3.50 | Homo sapiens kinesin family member 4A (KIF4A), ARNm [NM_012310] |
| KCNJ2 | 0.0001 | -3.47 | Homo sapiens potassium inwardly-rectifying channel, subfamily J, member 2 (KCNJ2), ARNm [NM_000891] |
| BARD1 | 0.0000 | -3.47 | Homo sapiens BRCA1 associated RING domain 1 (BARD1), ARNm [NM_000465] |
| MAP2K6 | 0.0039 | -3.45 | Homo sapiens mitogen-activated protein kinase kinase 6 (MAP2K6), transcript variant 1, ARNm [NM_002758] |
| OFD1 | 0.0000 | -3.44 | Homo sapiens oral-facial-digital syndrome 1 (OFD1), ARNm [NM_003611] |
| PLA1A | 0.0002 | -3.42 | Homo sapiens phospholipase A1 member A (PLA1A), ARNm [NM_015900] |

FIG. 2F

| GENE | FDR | FC | Description |
|---|---|---|---|
| RAD54B | 0.0025 | -3.42 | Homo sapiens RAD54 homolog B (S. cerevisiae) (RAD54B), transcript variant 1, ARNm [NM_012415] |
| PBK | 0.0047 | -3.42 | Homo sapiens PDZ binding kinase (PBK), ARNm [NM_018492] |
| NDRG2 | 0.0003 | -3.40 | Homo sapiens NDRG family member 2 (NDRG2), transcript variant 1, ARNm. [NM_201535] |
| ECM1 | 0.0000 | -3.34 | Homo sapiens extracellular matrix protein 1 (ECM1), transcript variant 2, ARNm. [NM_022664] |
| PRC1 | 0.0014 | -3.29 | Homo sapiens protein regulator of cytokinesis 1 (PRC1), transcript variant 1, ARNm [NM_003981] |
| MSX1 | 0.0001 | -3.26 | Homo sapiens msh homeo box homolog 1 (Drosophila) (MSX1), ARNm [NM_002448] |
| CCNB2 | 0.0004 | -3.23 | Homo sapiens cyclin B2 (CCNB2), ARNm [NM_004701] |
| LRRC1 | 0.0051 | -3.23 | Homo sapiens leucine rich repeat containing 1 (LRRC1), ARNm [NM_025168] |
| SORD | 0.0011 | -3.21 | Homo sapiens sorbitol dehydrogenase (SORD), ARNm [NM_003104] |
| EPHB3 | 0.0000 | -3.20 | Homo sapiens EPH receptor B3 (EPHB3), ARNm [NM_004443] |
| TMSL8 | 0.0028 | -3.20 | Homo sapiens thymosin-like 8 (TMSL8), ARNm [NM_021992] |
| RASSF2 | 0.0000 | -3.19 | Homo sapiens Ras association (RalGDS/AF-6) domain family 2 (RASSF2), transcript variant 1, ARNm [NM_014737] |
| TTC21B | 0.0221 | -3.17 | Homo sapiens ARNm for KIAA1992 protein. [AB082523] |
| OPRK1 | 0.0032 | -3.17 | Homo sapiens opioid receptor, kappa 1 (OPRK1), ARNm [NM_000912] |
| TMEM16A | 0.0006 | -3.13 | Homo sapiens transmembrane protein 16A (TMEM16A), ARNm [NM_018043] |
| CRABP2 | 0.0005 | -3.10 | Homo sapiens cellular retinoic acid binding protein 2 (CRABP2), ARNm [NM_001878] |
| FLJ10719 | 0.0036 | -3.10 | Homo sapiens hypothetical protein FLJ10719 (FLJ10719), ARNm [NM_018193] |
| PRKCQ | 0.0000 | -3.08 | Homo sapiens protein kinase C, theta (PRKCQ), ARNm [NM_006257] |

FIG. 2G

| GENE | FDR | FC | Description |
|---|---|---|---|
| CDC2 | 0.0020 | -3.06 | Homo sapiens cell division cycle 2, G1 to S and G2 to M (CDC2), transcript variant 1, ARNm [NM_001786] |
| BUB1B | 0.0037 | -3.05 | Homo sapiens BUB1 budding uninhibited by benzimidazoles 1 homolog beta (yeast) (BUB1B), ARNm [NM_001211] |
| STEAP4 | 0.0030 | -3.04 | Homo sapiens STEAP family member 4 (STEAP4), ARNm [NM_024636] |
| HEY1 | 0.0001 | -3.03 | Homo sapiens hairy/enhancer-of-split related with YRPW motif 1 (HEY1), ARNm [NM_012258] |
| EFEMP1 | 0.0030 | 3.00 | Homo sapiens EGF-containing fibulin-like extracellular matrix protein 1 (EFEMP1), transcript variant 1, ARNm [NM_004105] |
| IL2RB | 0.0001 | 3.01 | Homo sapiens interleukin 2 receptor, beta (IL2RB), ARNm [NM_000878] |
| EVC | 0.0032 | 3.02 | Homo sapiens tissue-type heart Ellis-van Creveld syndrome protein (EVC) ARNm, complete eds. [AF216184] |
| BCL6 | 0.0000 | 3.02 | Homo sapiens B-cell CLL/lymphoma 6 (zinc finger protein 51) (BCL6), transcript variant 2, ARNm [NM_138931] |
| IL15 | 0.0000 | 3.03 | Homo sapiens interleukin 15 (IL15), transcript variant 1, ARNm [NM_172174] |
| ASS1 | 0.0001 | 3.03 | Homo sapiens argininosuccinate synthetase (ASS), transcript variant 2, ARNm [NM_054012] |
| ATP6V1A | 0.0000 | 3.04 | Homo sapiens ATPase, H+ transporting, lysosomal 70kDa, V1 subunit A (ATP6V1A), ARNm [NM_001690] |
| CES1 | 0.0167 | 3.04 | Homo sapiens carboxylesterase 1 (monocyte/macrophage serine esterase 1) (CES1), transcript variant 3, ARNm [NM_001266] |

FIG. 2H

| GENE | FDR | FC | Description |
|---|---|---|---|
| ENPEP | 0.0000 | 3.05 | Homo sapiens glutamyl aminopeptidase (aminopeptidase A) (ENPEP), ARNm [NM_001977] |
| CYBRD1 | 0.0115 | 3.08 | Homo sapiens cytochrome b reductase 1 (CYBRD1), ARNm [NM_024843] |
| PPARGC1A | 0.0084 | 3.09 | Homo sapiens peroxisome proliferative activated receptor, gamma, coactivator 1, alpha (PPARGC1A), ARNm [NM_013261] |
| ARNSE4 | 0.0000 | 3.09 | Homo sapiens ribonuclease, ARNse A family, 4 (ARNSE4), transcript variant 1, ARNm [NM_194430] |
| FXYD2 | 0.0295 | 3.09 | Homo sapiens FXYD domain containing ion transport regulator 2 (FXYD2), transcript variant b, ARNm [NM_021603] |
| MT1H | 0.0013 | 3.12 | Homo sapiens metallothionein 1H (MT1H), ARNm [NM_005951] |
| GABARAPL1 | 0.0000 | 3.13 | Homo sapiens GABA(A) receptor-associated protein like 1 (GABARAPL 1), ARNm [NM_031412] |
| GBP2 | 0.0002 | 3.14 | Homo sapiens guanylate binding protein 2, interferon inducible (GBP2), ARNm [NM_004120] |
| LRFN4 | 0.0030 | 3.14 | Homo sapiens leucine rich repeat and fibronectin type III domain containing 4 (LRFN4), ARNm [NM_024036] |
| ARHGDIB | 0.0004 | 3.14 | Homo sapiens Rho GDP dissociation inhibitor (GDI) beta (ARHGDIB), ARNm [NM_001175] |
| CD7 | 0.0002 | 3.15 | Homo sapiens CD7 antigen (p41) (CD7), ARNm [NM_006137] |
| POLD4 | 0.0000 | 3.16 | Homo sapiens polymerase (ADN-directed), delta 4 (POLD4), ARNm [NM_021173] |

FIG. 2I

| GENE | FDR | FC | Description |
|---|---|---|---|
| HMHA1 | 0.0006 | 3.17 | Homo sapiens histocompatibility (minor) HA-1 (HMHA1), ARNm [NM_012292] |
| HRASLS3 | 0.0000 | 3.18 | Homo sapiens HRAS-like suppressor 3 (HRASLS3), ARNm [NM_007069] |
| AMIGO2 | 0.0000 | 3.20 | Homo sapiens adhesion molecule with Ig-like domain 2 (AMIGO2), ARNm [NM_181847] |
| S100A1 | 0.0000 | 3.20 | Homo sapiens S100 calcium binding protein A1 (S100A1), ARNm [NM_006271] |
| ACADSB | 0.0000 | 3.22 | Homo sapiens acyl-Coenzyme A dehydrogenase, short/branched chain (ACADSB), nuclear gene encoding mitochondrial protein, ARNm [NM_001609] |
| PSMB10 | 0.0000 | 3.22 | Homo sapiens proteasome (prosome, macropain) subunit, beta type, 10 (PSMB10), ARNm [NM_002801] |
| FOSL2 | 0.0000 | 3.26 | Homo sapiens FOS-like antigen 2 (FOSL2), ARNm [NM_005253] |
| EMCN | 0.0000 | 3.27 | Homo sapiens endomucin (EMCN), ARNm [NM_016242] |
| PROS1 | 0.0000 | 3.28 | Homo sapiens protein S (alpha) (PROS1), ARNm [NM_000313] |
| TH | 0.0029 | 3.31 | Homo sapiens tyrosine hydroxylase (TH), transcript variant 3, ARNm [NM_199293] |
| ADAMTS1 | 0.0000 | 3.32 | Homo sapiens a disintegrin-like and metalloprotease (reprolysin type) with thrombospondin type 1 motif, 1 (ADAMTS1), ARNm [NM_006988] |
| LEPREL1 | 0.0004 | 3.33 | Homo sapiens leprecan-like 1 (LEPREL1), ARNm [NM_018192] |
| HAL | 0.0000 | 3.37 | Homo sapiens histidine ammonia-lyase (HAL), ARNm [NM_002108] |
| DDX52 | 0.0000 | 3.38 | Homo sapiens DEAD (Asp-Glu-Ala-Asp) box polypeptide 52 (DDX52), transcript variant 2, ARNm [NM_152300] |

FIG. 2J

| GENE | FDR | FC | Description |
|---|---|---|---|
| SCYE1 | 0.0000 | 3.40 | Homo sapiens small inducible cytokine subfamily E, member 1 (endothelial monocyte-activating) (SCYE1), ARNm [NM_004757] |
| PTPRR | 0.0000 | 3.40 | Homo sapiens protein tyrosine phosphatase, receptor type, R (PTPRR), transcript variant 1, ARNm [NM_002849] |
| CLDN4 | 0.0000 | 3.41 | Homo sapiens claudin 4 (CLDN4), ARNm. [NM_001305] |
| VCAM1 | 0.0000 | 3.41 | Homo sapiens vascular cell adhesion molecule 1 (VCAM1), transcript variant 1, ARNm [NM_001078] |
| MT1G | 0.0009 | 3.41 | Homo sapiens metallothionein 1G (MT1G), ARNm [NM_005950] |
| IGF2 | 0.0021 | 3.41 | Homo sapiens insulin-like growth factor 2 (somatomedin A) (IGF2), transcript variant 1, ARNm [NM_000612] |
| MFAP5 | 0.0328 | 3.42 | Homo sapiens microfibrillar associated protein 5 (MFAP5), ARNm [NM_003480] |
| GDF15 | 0.0000 | 3.47 | Homo sapiens growth differentiation factor 15 (GDF15), ARNrn [NM_004864] |
| KRT7 | 0.0000 | 3.48 | Homo sapiens keratin 7 (KRT7), ARNm [NM_005556] |
| KCNK7 | 0.0016 | 3.49 | Homo sapiens potassium channel, subfamily K, member 7 (KCNK7), transcript variant C, ARNm [NM_005714] |
| MRPS2 | 0.0001 | 3.49 | Homo sapiens mitochondrial ribosomal protein S2 (MRPS2), nuclear gene encoding mitochondrial protein, ARNm [NM_016034] |
| TRA@ | 0.0002 | 3.52 | Homo sapiens T cell receptor alpha locus, ARNm (ADNc clone MGC:70922 IMAGE:5228329), complete cds. [BC063432] |

FIG. 2K

| GENE | FDR | FC | Description |
|---|---|---|---|
| SYNE2 | 0.0000 | 3.52 | Homo sapiens spectrin repeat containing, nuclear envelope 2 (SYNE2), transcript variant 5, ARNm [NM_182914] |
| LMCD1 | 0.0000 | 3.53 | Homo sapiens LIM and cysteine-rich domains 1 (LMCD1), ARNm [NM_014583] |
| FGB | 0.0021 | 3.53 | Homo sapiens fibrinogen beta chain (FGB), ARNm [NM_005141] |
| GAS1 | 0.0400 | 3.53 | Homo sapiens growth arrest-specific 1 (GAS1), ARNm. [NM_002048] |
| FAM59A | 0.0000 | 3.54 | Homo sapiens family with sequence similarity 59, member A (FAM59A), ARNm [NM_022751] |
| ID4 | 0.0000 | 3.56 | Homo sapiens inhibitor of AON binding 4, dominant negative helix-loop-helix protein (104), ARNm [NM_001546] |
| ACTA2 | 0.0008 | 3.58 | Homo sapiens actin, alpha 2, smooth muscle, aorta (ACTA2), ARNm [NM_001613] |
| COTL1 | 0.0002 | 3.58 | Homo sapiens coactosin-like 1 (Dictyostelium) (COTL 1), ARNm [NM_021149] |
| PROM1 | 0.0014 | 3.65 | Homo sapiens prominin 1 (PROM1), ARNm [NM_006017] |
| AGR2 | 0.0001 | 3.67 | Homo sapiens anterior gradient 2 homolog (Xenopus laevis) (AGR2), ARNm [NM_006408] |
| CLDN10 | 0.0002 | 3.68 | Homo sapiens claudin 1o (CLDN10), transcript variant 1, ARNm [NM_182848] |
| RRAS | 0.0000 | 3.70 | Homo sapiens related RAS viral (r-ras) oncogene homolog (RRAS), ARNm [NM_006270] |
| TIMP3 | 0.0000 | 3.71 | Homo sapiens tissue inhibitor of metalloproteinase 3 (Sorsby fundus dystrophy, pseudoinflammatory) (TIMP3), ARNm [NM_000362J |
| MT2A | 0.0004 | 3.72 | Homo sapiens metallothionein 2A (MT2A), ARNm [NM_005953] |
| XCL2 | 0.0000 | 3.73 | Homo sapiens chemokine (C motif) ligand 2 (XCL2), ARNm [NM_003175] |
| RARRES3 | 0.0000 | 3.79 | Homo sapiens retinoic acid receptor responder (tazarotene induced) 3 (RARRES3), ARNm [NM_004585] |

FIG. 2L

| GENE | FDR | FC | Description |
|---|---|---|---|
| DEPDC6 | 0.0000 | 3.80 | Homo sapiens DEP domain containing 6 (DEPDC6), ARNm [NM_022783] |
| NP | 0.0000 | 3.85 | Homo sapiens nucleoside phosphorylase (NP), ARNm [NM_000270] |
| CXCL13 | 0.0025 | 3.90 | Homo sapiens chemokine (C-X-C motif) ligand 13 (B-cell chemoattractant) (CXCL 13), ARNm [NM_006419] |
| IMPA2 | 0.0000 | 3.91 | Homo sapiens inositol(myo)-1(or 4)-monophosphatase 2 (IMPA2), ARNm [NM_014214] |
| HAND2 | 0.0000 | 3.91 | Homo sapiens heart and neural crest derivatives expressed 2 (HAND2), ARNm [NM_021973] |
| LMOD1 | 0.0000 | 3.92 | Homo sapiens leiomodin 1 (smooth muscle) (LMOD1), ARNm [NM_012134] |
| STAR | 0.0006 | 3.93 | Homo sapiens steroidogenic acute regulator (STAR), nuclear gene encoding mitochondrial protein, transcript variant 1, ARNm [NM_000349] |
| FLJ20152 | 0.0000 | 3.94 | Homo sapiens hypothetical protein FLJ20152 (FLJ20152), transcript variant 1, ARNm [NM_001034850] |
| SLC38A1 | 0.0000 | 3.97 | Homo sapiens solute carrier family 38, member 1 (SLC38A1), ARNm [NM_030674] |
| C10orf10 | 0.0008 | 3.98 | Homo sapiens chromosome 10 open reading frame 10 (C10orf10), ARNm [NM_007021] |
| CDA | 0.0000 | 4.00 | Homo sapiens cytidine deaminase (CDA), ARNm [NM_001785] |
| TBC1D2 | 0.0000 | 4.07 | Homo sapiens TBC1 domain family, member 2 (TBC1D2), ARNm [NM_018421] |
| GZMA | 0.0008 | 4.07 | Homo sapiens granzyme A (granzyme 1, cytotoxic T-lymphocyte-associated serine esterase 3) (GZMA), ARNm [NM_006144] |
| HABP2 | 0.0011 | 4.09 | Homo sapiens hyaluronan binding protein 2 (HABP2), ARNm [NM_004132] |
| DKK1 | 0.0000 | 4.10 | Homo sapiens dickkopf homolog 1 (Xenopus laevis) (DKK1), ARNm [NM_012242] |

FIG. 2M

| GENE | FDR | FC | Description |
|---|---|---|---|
| SPP1 | 0.0000 | 4.15 | Homo sapiens SEQreted phosphoprotein 1 (osteopontin, bone sialoprotin I, early T-lymphocyte activation 1) (SPP1), ARNm (NM_000582} |
| DEFB1 | 0.0019 | 4.17 | Homo sapiens defensin, beta 1 (DEFB1), ARNm [NM_005218] |
| ARID5B | 0.0000 | 4.19 | Homo sapiens AT rich interactive domain 5B (MRF1-like) (ARID5B), ARNm [NM_032199] |
| ANXA4 | 0.0000 | 4.27 | Homo sapiens annexin A4 (ANXA4), ARNm [NM_001153] |
| ARG2 | 0.0000 | 4.35 | Homo sapiens arginase, type II (ARG2), nuclear gene encoding mitochondrial protein, ARNm [NM_001172] |
| SLPI | 0.0000 | 4.39 | Homo sapiens SEQretory leukocyte protease inhibitor (antileukoproteinase) (SLPI), ARNm [NM_003064] |
| CORO1A | 0.0000 | 4.40 | Homo sapiens coronin, actin binding protein, 1A (CORO1A), ARNm [NM_007074] |
| NKG7 | 0.0000 | 4.42 | Homo sapiens natural killer cell group 7 sequence (NKG7), ARNm [NM_005601] |
| INDO | 0.0000 | 4.49 | Homo sapiens indoleamine-pyrrole 2,3 dioxygenase (INDO), ARNm [NM_002164] |
| GNLY | 0.0007 | 4.53 | Homo sapiens granulysin (GNLY), transcript variant NKG5, ARNm [NM_006433] |
| S100A4 | 0.0000 | 4.59 | Homo sapiens S100 calcium binding protein A4 (S100A4), transcript variant 1, ARNm [NM_002961] |
| AQP3 | 0.0006 | 4.63 | Homo sapiens aquaporin 3 (Gill blood group) (AQP3), ARNm [NM_004925] |
| C3 | 0.0003 | 4.67 | Homo sapiens complement component 3 (C3), ARNm [NM_000064] |

FIG. 2N

| GENE | FDR | FC | Description |
|---|---|---|---|
| GPRC5C | 0.0000 | 4.69 | Homo sapiens G protein-coupled receptor, family C, group 5, member C (GPRC5C), transcript variant 1, ARNm [NM_022036] |
| IER3 | 0.0000 | 4.69 | Homo sapiens immediate early response 3 (IER3), transcript variant long, ARNm [NM_052815] |
| CLU | 0.0000 | 4.70 | Homo sapiens clusterin (CLU), transcript variant 2, ARNm [NM_203339] |
| MYL9 | 0.0001 | 4.72 | Homo sapiens myosin, light polypeptide 9, regulatory (MYL9), transcript variant 2, ARNm [NM_181526] |
| DHRS3 | 0.0006 | 4.72 | Homo sapiens dehydrogenase/reductase (SOR family) member 3 (DHRS3), ARNm [NM_004753] |
| CTSW | 0.0009 | 4.78 | Homo sapiens cathepsin W (CTSW), ARNm [NM_001335] |
| CYP3A5 | 0.0000 | 4.82 | Homo sapiens cytochrome P450, family 3, subfamily A, polypeptide 5 (CYP3A5), ARNm [NM_000777] |
| AOX1 | 0.0009 | 4.82 | Homo sapiens aldehyde oxidase 1 (AOX1), ARNm [NM_001159] |
| GLIPR1 | 0.0000 | 4.83 | Homo sapiens GLI pathogenesis-related 1 (glioma) (GLIPR1), ARNm [NM_006851] |
| ABLIM3 | 0.0047 | 4.87 | Homo sapiens actin binding LIM protein family, member 3 (ABLIM3), ARNm [NM_014945] |
| RARRES1 | 0.0000 | 4.87 | Homo sapiens retinoic acid receptor responder (tazarotene induced) 1 (RARRES1), transcript variant 2, ARNm [NM_002888] |
| EDNRB | 0.0000 | 4.89 | Homo sapiens endothelin receptor type B (EDNRB), transcript variant 2, ARNm [NM_003991] |
| GAST | 0.0000 | 5.00 | Homo sapiens gastrin (GAST), ARNm [NM_000805] |

FIG. 2O

| GENE | FDR | FC | Description |
|---|---|---|---|
| RPRM | 0.0000 | 5.03 | Homo sapiens reprimo, TP53 dependant G2 arrest mediator candidate (RPRM), ARNm [NM_019845] |
| C14orf161 | 0.0000 | 5.07 | Homo sapiens chromosome 14 open reading frame 161 (C14orf161), ARNm [NM_024764] |
| CRISP3 | 0.0002 | 5.09 | Homo sapiens cysteine-rich SEQretory protein 3 (CRISP3), ARNm [NM_006061] |
| CFD | 0.0000 | 5.13 | Homo sapiens D component of complement (adipsin) (DF), ARNm [NM_001928] |
| SERPING1 | 0.0000 | 5.16 | Homo sapiens serpin peptidase inhibitor, clade G (C1 inhibitor), member 1, (angioedema, hereditary) (SERPING1), transcript variant 1, ARNm [NM_000062] |
| HPSE | 0.0041 | 5.17 | Homo sapiens heparanase (HPSE), ARNm [NM_006665] |
| THBS2 | 0.0000 | 5.17 | Homo sapiens thrombospondin 2 (THBS2), ARNm [NM_003247] |
| PTGER2 | 0.0005 | 5.18 | Homo sapiens prostaglandin E receptor 2 (subtype EP2), 53kDa (PTGER2). ARNm [NM_000956] |
| IGFBP1 | 0.0241 | 5.35 | Homo sapiens insulin-like growth factor binding protein 1 (IGFBP1), ARNm [NM_000596] |
| SLC15A1 | 0.0000 | 5.59 | Homo sapiens solute carrier family 15 (oligopeptide transporter), member 1 (SLC15A1), ARNm [NM_005073] |
| TAGLN | 0.0002 | 5.71 | Homo sapiens transgelin (TAGLN), ARNm [NM_003186] |
| KLRC1 | 0.0000 | 5.75 | Homo sapiens killer cell lectin-like receptor subfamily C, member 1 (KLRC1), transcript variant 2, ARNm [NM_007328] |
| EFNA1 | 0.0000 | 5.77 | Homo sapiens ephrin-A1 (EFNA1), transcript variant 1, ARNm [NM_004428] |

FIG. 2P

| GENE | FDR | FC | Description |
|---|---|---|---|
| ADRA2A | 0.0008 | 5.78 | Homo sapiens adrenergic, alpha-2A-, receptor (ADRA2A), ARNm [NM_000681] |
| XCL1 | 0.0000 | 5.80 | Homo sapiens chemokine (C motif) ligand 1 (XCL1), ARNm [NM_002995] |
| ABCC3 | 0.0000 | 5.98 | Homo sapiens ATP-binding cassette, sub-family C (CFTR/MRP), member 3 (ABCC3), ARNm [NM_003786] |
| ANG | 0.0000 | 5.98 | Homo sapiens angiogenin, ribonuclease, ARNse A family, 5 (ANG), ARNm [NM_001145] |
| C4,4[a] | 0.0000 | 6.03 | Homo sapiens GPI-anchored metastasis- associated protein homolog (C4,4A), ARNm [NM_014400] |
| G0S2 | 0.0106 | 6.20 | Homo sapiens putative lymphocyte G0/G1 switch gene (G0S2), ARNm. [NM_015714] |
| CP | 0.0000 | 6.34 | Homo sapiens ceruloplasmin (ferroxidase) (CP), ARNm [NM_000096] |
| SNX10 | 0.0001 | 6.56 | Homo sapiens sorting nexin 10 (SNX10), ARNm [NM_013322] |
| S100P | 0.0033 | 6.95 | Homo sapiens S100 calcium binding protein P (S100P), ARNm [NM_005980] |
| SCGB2A2 | 0.0213 | 7.43 | Homo sapiens SEQretoglobin, family 2A, member 2 (SCGB2A2), ARNm [NM_002411] |
| DPP4 | 0.0495 | 7.72 | Homo sapiens dipeptidylpeptidase 4 (CD26, adenosine deaminase complexing protein 2) (DPP4), ARNm [NM_001935] |
| NNMT | 0.0000 | 7.74 | Homo sapiens nicotinamide N-methyltransferase (NNMT), ARNm [NM_006169] |
| THBD | 0.0003 | 7.84 | Homo sapiens thrombomodulin (THBD), ARNm. [NM_000361] |

FIG. 2Q

| GENE | FDR | FC | Description |
|---|---|---|---|
| MUC16 | 0.0001 | 8.01 | Homo sapiens mucin 16, cell surface associated (MUC16), ARNm [NM_024690] |
| GADD45A | 0.0000 | 8.25 | Homo sapiens growth arrest and ADN-damage-inducible, alpha (GADD45A), ARNm [NM_001924] |
| SOD2 | 0.0000 | 9.06 | Homo sapiens superoxide dismutase 2, mitochondrial (8002), nuclear gene encoding mitochondrial protein, transcript variant 2, ARNm [NM_001024465] |
| MAOA | 0.0000 | 9.39 | Homo sapiens monoamine oxidase A (MAOA), nuclear gene encoding mitochondrial protein, ARNm [NM_000240] |
| LAMB3 | 0.0000 | 11.32 | Homo sapiens laminin, beta 3 (LAMB3), transcript variant 2, ARNm [NM_001017402] |
| TSPAN8 | 0.0000 | 12.90 | Homo sapiens tetraspanin 8 (TSPAN8), ARNm [NM_004616] |
| C4BPA | 0.0000 | 13.14 | Homo sapiens complement component 4 binding protein, alpha (C4BPA), ARNm [NM_000715] |
| CXCL14 | 0.0000 | 14.02 | Homo sapiens chemokine (C-X-C motif) ligand 14 (CXCL14), ARNm [NM_004887] |
| TCN1 | 0.0000 | 14.76 | Homo sapiens transcobalamin I (vitamin B12 binding protein, R binder family) (TCN1), ARNm [NM_001062] |
| LIF | 0.0000 | 15.03 | Homo sapiens leukemia inhibitory factor (cholinergic differentiation factor) (LIF), ARNm [NM_002309] |
| SLC1A1 | 0.0000 | 17.57 | Homo sapiens solute carrier family 1 (neuronal/epithelial high affinity glutamate transporter, system Xag), member 1(SLC1A1), ARNm [NM_004170] |
| COMP | 0.0000 | 30.95 | Homo sapiens cartilage oligomeric matrix protein (COMP), ARNm [NM_000095] |

FIG. 2R

| GENE | FDR | FC | Description |
|---|---|---|---|
| PAEP | 0.0000 | 31.43 | Homo sapiens progestagen-associated endometrial protein (placental protein 14, pregnancy-associated endometrial alpha-2-globulin, alpha uterine protein) (PAEP), transcript variant 2, ARNm [NM_002571] |
| GPX3 | 0.0000 | 35.49 | Homo sapiens glutathione peroxidase 3 (plasma) (GPX3), ARNm [NM_002084] |

FIG. 3

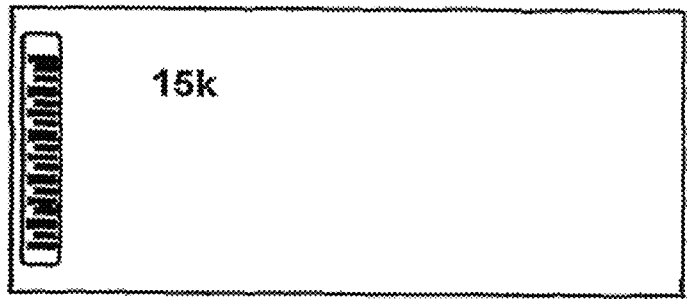

| | Forward primers | Reverse primers | Tm (tested) |
|---|---|---|---|
| CLDN10 | CTGGAAGGTGTCTACCATCGA (SEQ ID NO: 1) | AAAGAAGCCCAGGCTGACA (SEQ ID NO: 2) | 59°C |
| SPP1 | TAAACCCTGACCCATCTCAGA (SEQ ID NO: 3) | TGAGACTCATCAGACTGGTGA (SEQ ID NO: 4) | 59°C |
| FXYD2 | AATGACTGGGTTGTCGATGGA (SEQ ID NO: 5) | ACAGCGGAATCTTCTGCTGA (SEQ ID NO: 6) | 59°C |
| MT1G | TCCTGCAAGTGCAAAGAGTG (SEQ ID NO: 7) | GGAATGTAGCAAAGGGGTCA (SEQ ID NO: 8) | 57°C |
| GPX3 | AGGTGGAGGCTTTGTCCCTA (SEQ ID NO: 9) | TATACCATCTGGCCCCACCA (SEQ ID NO: 10) | 59°C |
| GAPDH | GAAGGTGAAGGTCGGAGTC (SEQ ID NO: 11) | GAAGATGGTGATGGGATTTC (SEQ ID NO: 12) | 59°C |

FIG. 5

| | FC(LH+7/LH+2)ERA | FC(LH+7/LH+2) RT-PCR |
|---|---|---|
| GPx3 | 19.8070545 | 130.2040574 |
| CLDN10 | 1.30339729 | 1.984951148 |
| FXDY2 | 13.0853163 | 139.7016257 |
| SPP1 | 6.060586755 | 7.914182355 |
| MT1G | 5.954582721 | 16.23315915 |
| | FC(LH+7/D8)ERA | FC(LH+7/D8) RT-PCR |
| GPx3 | 7.456705357 | 27.4794737 |
| CLDN10 | 1.057840819 | -1.039567963 |
| FXDY2 | 16.10753719 | 174.7220849 |
| SPP1 | 26.8184704 | 21.27686601 |
| MT1G | 4.326906413 | 33.07318862 |
| | FC(LH+7/D9)ERA | FC(LH+7/D9) RT-PCR |
| GPx3 | 7.699748311 | 16.20106422 |
| CLDN10 | 0.930467377 | 1.022744443 |
| FXDY2 | 13.10276318 | 87.22494503 |
| SPP1 | 16.24735023 | 15.31094514 |
| MT1G | 8.371265666 | 21.27203476 |
| | FC(LH+7/D10)ERA | FC(LH+7/D10) RT-PCR |
| GPx3 | 12.24148146 | 11.36573697 |
| CLDN10 | 0.569558516 | -1.459465381 |
| FXDY2 | 14.43207825 | 90.46145386 |
| SPP1 | 10.31843956 | 4.226648972 |
| MT1G | 8.191564984 | 14.92748338 |
| | FC(LH+7/D11)ERA | FC(LH+7/D11) RT-PCR |
| GPx3 | 9.186371663 | 21.76599431 |
| CLDN10 | 1.183075031 | 1.05487026 |
| FXDY2 | 15.20761532 | 110.6903147 |
| SPP1 | 21.22735078 | 8.926914281 |
| MT1G | 6.128246059 | 23.77669176 |
| | FC(LH+7/D14)ERA | FC(LH+7/D14) RT-PCR |
| GPx3 | 7.674066657 | 17.66530261 |
| CLDN10 | 1.19140354 | 1.294677934 |
| FXDY2 | 14.68545681 | 70.54464815 |
| SPP1 | 24.71975888 | 11.6031628 |
| MT1G | 4.935426962 | 15.79236793 |
| | FC(LH+7/D26)ERA | FC(LH+7/D26) RT-PCR |
| GPx3 | 0.063521753 | -12.82279791 |
| CLDN10 | 0.763764898 | -2.900232179 |
| FXDY2 | 0.192925494 | -6.959532082 |
| SPP1 | 0.784443779 | -7.523272248 |
| MT1G | 1.037453334 | 1.83864534 |

FIG. 7

| A B | Actual Class | Prediction |
|---|---|---|
| Array 1 | Other | Other |
| Array 2 | receptive | receptive |
| Array 3 | Other | Other |
| Array 4 | Other | Other |
| Array 5 | Other | Other |
| Array 6 | receptive | receptive |
| Array 7 | receptive | receptive |
| Array 8 | receptive | receptive |
| Array 9 | receptive | receptive |
| Array 10 | receptive | receptive |
| Array 11 | receptive | receptive |
| Array 12 | Other | Other |
| Array 13 | Other | Other |
| Array 14 | receptive | receptive |
| Array 15 | receptive | receptive |
| Array 16 | receptive | receptive |
| Array 17 | receptive | receptive |
| Array 18 | receptive | receptive |
| Array 19 | Other | Other |
| Array 20 | Other | Other |
| Array 21 | Other | Other |
| Array 22 | Other | Other |
| Array 23 | Other | Other |

=== Confusion Matrix ===

```
 a   b      Classified as:
11   0 |    a = Other
 0  12 |    b = receptive
```

GENE EXPRESSION PROFILE AS AN ENDOMETRIAL RECEPTIVITY MARKER

CROSS REFERENCE TO RELATED APPLICATIONS

This application is a National Stage of International Application No. PCT/ES2009/000386, filed on Jul. 22, 2009, which claims priority from International Application No. PCT/ES08/000513, filed on Jul. 22, 2008, the contents of all of which are incorporated herein by reference in their entirety.

FIELD OF THE ART

The present invention relates to determining the receptivity of the human endometrium from a gene expression profile. More specifically, it consists of developing a specific expression microarray of endometrial receptivity (Endometrial Receptivity Array or ERA) which allows evaluating the receptive state of a human endometrium, as well as assessing said state for diagnostic and therapeutic purposes.

PRIOR ART

The endometrium is the mucosa coating the inside of the uterine cavity. Its function is to house the embryo, allowing its implantation and favoring the development of the placenta. This process requires a receptive endometrium capable of responding to the signals of the blastocyst, which is the stage of development of the embryo when it implants. Human endometrium is a tissue cyclically regulated by hormones, the hormones preparing it to reach said receptivity state are estradiol, which induces cell proliferation, and progesterone which is involved in differentiation, causing a large number of changes in the gene expression profile of the endometrium, which reaches a receptive phenotype for a short time period referred to as "window of implantation". Though there is no consensus as to the implantation period in humans, clinical studies suggest that this process takes place between days 20 and 24 of a normal ovulation cycle (Wilcox at al., 1999), day LH+7 (day 20-21) being considered critical.

The evolution of our knowledge about the human endometrium contrasts with the lack of progress in developing new diagnostic methods for the dating and study thereof. The endometrium is still evaluated today by means of histological studies based on in observations described over 50 years ago (Noyes at al., 1950) or with macroscopic techniques with little resolution as equally non-objective ultrasound studies which lack specificity and produce widely varying results.

In 1950, Noyes et al. described for the first time a method for endometrial dating based exclusively on histological criteria and on the morphological changes of the different compartments of the endometrium in response to the presence of estrogens and progesterone. Noyes et al. studied the histological features of endometrial biopsies taken during 8,000 spontaneous cycles in 300 women (Noyes et al., 1950). They were able to relate different histological patterns with particular moments of the menstrual cycle by correlating the histological changes with the basal body temperature. These morphological criteria continue to be used today and are considered the Gold Standard for the study of the endometrium, evaluation of endometrial receptivity and detection of endometrial anomalies.

However, this technique does have its drawbacks. It has been demonstrated that the use of histological features fails when distinguishing the phase of the menstrual cycle, and it also fails as a means to discriminate between fertile and infertile women, concluding that it is not suitable for clinical use. The subjectivity involved in visual observation means that there is an inter-observer, intra-observer and inter-cycle variability altering the consistency of the results obtained. Furthermore, ovarian stimulation typical of assisted reproductive treatments (ART) modifies the endometrial maturation process compared to natural cycles which can barely be explained with Noyes' criteria (Papanikolaou et al., 2005). For this reason there are many works in the literature which question the histological observations interpreted by one or several pathologies both in retrospective clinical studies (Balash et al., 1992; Batista et al., 1993; Shoupe et al., 1989), prospective clinical studies (Li et al., 1989; Creus et al., 2002; Ordi et al., 2003), and recently in randomized studies (Murray et al., 2004; Coutifaris et al., 2004). The Practice Committee of the American Society for Reproductive Medicine (ASRM) also establishes that even though the classic criterion of the luteal phase defect consists of a delay in the endometrial maturation of >2 days following the Noyes criteria, this Committee has serious doubts as to the accuracy of said histological criteria and therefore of the prevalence of the luteal phase defect (LPD) and even of its clinical relevance as a cause of infertility (ASRM, 2000).

In this sense, Balasch at al., 1992 demonstrated that the incidence of LPD and histological endometrial patterns were similar in fertile and infertile women. Moreover, a suitable endometrial histology in the ovulation cycle or in previous ones was not related to the pregnancy data in infertile women concluding that the histological evaluation of the endometrium in the luteal phase is not useful for predicting or improving the reproductive results (Balasch et al., 1992). In other studies of the same group, it was demonstrated that there was a clear dissociation in the temporary expression of a series of markers related to the window of implantation (alpha and beta 3 integrins) and the pinopod expression. They furthermore did not find differences in the expression of these markers between fertile and infertile women (Creus et al., 2002). They also demonstrated a high variability between cycles and low reproducibility for these markers (Ordi et al., 2003).

Li et al. 1989 dated 63 endometrial biopsies on two different occasions by the same pathologist, demonstrating that there was complete agreement in only 24% of them. In a separate study, they observed that between different cycles in the same woman, there was complete agreement in only 4% of the cases. These data emphasize the lack of precision of traditional dating methods and their lack of any assurances for predicting the development in the following cycles (Li et al., 1989).

The differences between pathologists varied depending on the day of the menstrual cycle in which the endometrial biopsy is taken. Over 20% of the endometrial biopsies were dated with a difference of at least two days between pathologists in the early, mid and late luteal phases. Inter-cycle variations reach 60% in the mid luteal phase (Murray et al., 2004). It has been demonstrated that during the window of implantation, a very similar percentage of women has the endometrium out of phase, 49.4% fertile versus 43.2% infertile (p=0.33) and, ultimately, that the histological dating is not related to fertility status (Coutifaris et al., 2004). These variations described suggest that the traditional criteria are not precise and that new technologies are required for dating and functionally identifying the endometrial samples.

In the pre-genomic era, only "gene-by-gene" studies could be carried out to select useful candidates for studying uterine receptivity or for determining the endometrial situation in women with or without endometriosis.

Therefore, in the present genomic era objective tools based on molecular criteria which improve the diagnostic capacity of determined techniques such as the histological technique, which is very useful, however, for other types of needs, are sought.

In the mid 1990s (Schena et al., 1995), a revolutionary technology was developed for determining and quantifying the expression of messenger RNA (mRNA) in a sample, gene expression microarrays. Their main advantage is that they offer the possibility of simultaneously analyzing thousands of genes in a single experiment. A DNA microarray consists of a large number of DNA molecules arranged on a solid substrate such that they form an array of sequences in two or three dimensions. These fragments of genetic material can be short sequences called oligonucleotides or larger sequences, such as complementary DNA (cDNA) which is synthesized from mRNA, or PCR products (in vitro replication of DNA sequences by means of the polymerase chain reaction). These single-strand nucleotides fragments immobilized on the support are referred to as "probes". The nucleic acids of the samples to be analyzed are labeled using different methods (enzymatic, fluorescent methods, etc.) and are incubated on the probe panel, which allows hybridization (recognition and binding between complementary molecules) of homologous sequences. During hybridization, the labeled genetic material samples bind to their complementary samples immobilized on the support of the chip, allowing the identification and quantification of the DNA present in the sample. The suitable bioinformatic tools and scanner then allow interpreting and analyzing the data obtained (Al-Shahrour F at al., 2005).

To use a microarray, commercially available microarrays can be used or one can be custom designed.

To design a microarray, the following operations must be performed:
a) Choosing the type of probe, oligos, cDNA, . . .
b) Labeling probes or samples: enzymatic, fluorescent, . . .
c) Support material: glass, plastic, membranes, . . .
d) Immobilizing probes: active, passive, covalent, . . .
e) Manufacturing: printing, in situ synthesis, . . .
f) Detecting hybridization: scanner, fluorometry, . . .
g) Data processing: software.

This technology is being applied to the analysis of gene expression, sequencing, therapy follow-up, preventive medicine, drug toxicology and molecular diagnosis. The manufacture of microarrays, also referred to as bioarrays or biochips has been described in various patent documents, such as for example WO 2005/018796 A1, US 2005/0048554 A1, and US 2005/0046758 A1. Their use has also been applied to dendrimers (WO 2005/040094 A1) and large biomolecules (US 2005/0042363 A1) or for collecting information on samples, such as for example identifying a carcinogenic or pathogenic cell in an individual (WO 2005/016230 A2). Their use is also known for immobilizing nucleic acids which are complementary to a variety of genes, being applied to the field of chemistry, biology, medicine and medical diagnostics (U.S. Pat. No. 6,821,724 B1). Microarrays are currently being used to make comparisons based on genomic data and to research different systems.

There are different patent and non-patent literature publications on this subject. Microarray technology has allowed globally studying the gene expression of the endometrium under physiological conditions during the different phases of the menstrual cycle in the natural cycle (Ponnampalam et al., 2004, Talbi et al., 2005). With respect to the human window of implantation, gene expression profiles of the endometrium in the natural cycle have been described (Borthwick et al., 2003; Carson et al., 2002; Riesewijk et al., 2003; Mirkin et al., 2005). The gene expression profile of the endometrium during the window of implantation in stimulated cycles has also been analyzed (Mirkin et al., 2004; Horcajadas et al., 2005 (Provide literature reference in the Literature section); Simòn C et al., 2005) and in response to drugs such as RU486 (Catalano et al., 2003 (Provide literature reference in the Literature section); Sharkey et al., 2005).

The refractory profile of the human endometrium in the presence of an intrauterine device (IUD) during the window of implantation has also been studied (Horcajadas et al. 2006). All these works have recently been reviewed by the authors of the present application (Horcajadas et al., 2007). The conclusion of said study is that even though different genomic studies of the human endometrium in different physiological and pathological conditions have been conducted in the last 4 years, generating a large amount of information on the gene regulation during the window of implantation both in fertile and infertile women, the key molecules and mechanisms have yet to be discovered.

In the field of patents, there are several which try to determine endometrial receptivity/non-receptivity, though neither the genes, nor the technology, nor the predictive systems they postulate coincide with those used in the present invention.

Patent document US 2003/0077589 A1 describes a method for diagnosing endometriosis based on identifying the product of at least one of the genes of the group consisting of fibronectin, PTK7 transmembrane receptor, type XVIII collagen, alpha 1, protein similar to subtilisin (PACE4), laminin M chain (merosin), elastin, type IV collagen, alpha 2, interferon-alpha-inducible gene p27, reticulocalbin, aldehyde dehydrogenase 6, gravin, nidogen and phospholipase C epsilon, in which a small amount of the control gene indicates the presence of endometriosis.

Patent application US 2003/0125282 A1 describes two human MATER proteins (mice MATER proteins were already known) and their relationship and use for fertility disorders.

Document US 2003/0186300 A1 describes methods and commercial compositions for the diagnosis and treatment of reproduction-associated diseases. The invention also relates to methods and compositions for the determination and modulation of endometrial receptivity.

Patent US 2005/0032111 A1 uses the expression of cadherin-11 in endometrial tissue as an indicator of the capacity for establishing or maintaining a pregnancy.

Document US 2005/0106134 A1 relates to the role of the enzyme proprotein convertase 5/6 during pregnancy, and particularly its detection and the detection of its isoforms in the uterus. This enzyme is useful in fertility control for monitoring a premature pregnancy and for detecting the uterine receptivity in mammals. New forms of proprotein convertase 5/6 are also described.

Patent US 2003/0228636 A1 describes a method for detecting endometrial receptivity for embryo implantation, which comprises: obtaining a sample of the endometrium, contacting the endometrium with a monoclonal antibody for $\beta_3$, and detecting $\beta_3$ in the endometrium. Contraceptives and diagnostic kits useful for carrying out the methods of the invention are also mentioned.

Patent application WO 2005/061725 A1 describes methods for detecting markers associated with endometrial diseases or a determined endometrial phase in a woman, which comprise measuring the peptide endometrial markers or the polynucleotides encoding the markers in the studied sample. The invention also provides methods for detecting endometrial diseases, as well as kits for carrying out the methods of the invention.

Document WO 01/89548 A2 relates to the pharmaceutical use of the fibulin-1 polypeptide and nucleic acid in birth control in women, and for the diagnosis and treatment of the endometriosis.

In patent WO 2004/058999 A2, the invention relates to a method and the means for determining the specific conditions or changes in the uterine mucosa or in the epithelium of other organs. The method allows determining the over-expression of type 1-β (β7,β6,B6e) mRNA subunits of human gonadotropin. The measurements of the expression of β7,β6,β6e are used to indicate the receptivity of the uterine mucosa to implantation of an embryo or to indicate neoplastic changes in epithelia.

Patent US 2004/0005612 A1 identifies genetic sequences with expression levels which are suppressed or induced in the human endometrium during the window of implantation. The genes characterized during the window of implantation provide material for screening tests for the purpose of determining endometrial alterations and fertility disorders, as well as endometrial-based birth control methods.

U.S. Pat. No. 6,733,962 B2 describes a method for diagnosing abnormal endometrial development of a woman based on the expression of cyclin E and p27 in a sample obtained after day 20 of the menstrual cycle of a woman which ideally lasts 28 days.

In summary, for over 50 years the attempt has been made to determine a histological standard for being used in the clinical diagnosis of endometrial receptivity based on morphological observations. Today, with microarray technology, which is much more precise than morphological observations, works have been published relating to different genes present throughout the menstrual cycle, but the results do not coincide because the experimental design, collecting the samples and selecting the genes are crucial for reaching any conclusions.

Therefore, it is still and more than ever necessary to have a microarray which encompasses selecting genes which generate an expression profile that serves to diagnose and determine if the state of a particular endometrium corresponds to the receptivity/non-receptivity state.

Therefore, a list of genes and probes has been determined in this application which, once incorporated to a microarray, by means of analyzing the joint expression of these genes in the sample under study using a defined and trained computational prediction model, is capable of evaluating the receptivity/non-receptivity state of a sample of the endometrium obtained 7 days after the LH surge, as well as situations of sub-fertility of an endometrial origin depending on the gene expression profile of all of them.

Therefore, the method of the present invention uses the joint expression of the process-related mRNA as a whole as an endometrial receptivity marker, unlike the remaining receptivity molecular markers of the prior which are based on studying a molecule or a small group of molecules considered independently.

OBJECT OF THE INVENTION

The present invention allows determining the human endometrial receptivity functional state by means of using two components: on one hand, the design of a specific microarray which identifies the gene expression profile of the situation of human endometrial receptivity/non-receptivity and on the other, the subsequent analysis of the expression profile of this specific microarray by means of a computational predictor which is capable of assigning a receptivity status.

To that end, the steps described below are followed:

1. Identifying a set of genes that are involved in endometrial receptivity for their inclusion in a specific microarray of endometrial receptivity (Endometrial Receptivity Array, ERA).

2. Creating the specific microarray.

3. Analyzing the expression pattern of the ERA during the window of implantation by means of bioinformatic tools, to be able to establish the endometrial receptivity profile and create a prediction model.

4. Developing software which, with this prediction model based on the gene expression profile, allows quantitatively and objectively evaluating and predicting the in vivo endometrial receptive state.

The foundation of the microarray is the following: when a gene is active, mRNA molecules which have a base sequence complementary to that of the gene are produced. When a gene is inactive mRNA is not produced. The analysis consists of extracting the total mRNA from two cell populations which vary in the situation to be studied, in this case receptive and non-receptive endometrium, labeling it with a fluorescent substance and hybridizing it on the microarray. Since each mRNA matches up only to the probe of the gene having the same complementary base sequence, those probes which capture the most mRNA—and which therefore shine with more fluorescence—will indicate which genes were the most active. If the fluorescence pattern of the receptive endometrium is compared to that of the non-receptive endometrium, it will be known which genes are differentially expressed in one situation with respect to the other, and that they are therefore process-related.

The probes are designed so that the mRNA of the gene to which they belong bond to them and are fixed in the support of the array. The oligonucleotides forming the probe are inserted in an automated manner in a layer of glass, nylon or plastic, being placed in squares acting like a micro-test tube. The oligonucleotide microarrays are made in an automated manner and inserted by robots by means of photolithography or piezoelectric printing. The result is an automated and normalized process which allows thousands of printings per $cm^2$ and minute.

The distribution of the probes in the microarray as a set of probes is generally observed; those having the same sequence are located at the same point in the array. In the ERA of the present invention, the probes are oligos with 60 nucleotides. Therefore, what is labeled and loose in the solution hybridized in the microarray are labeled mRNA fragments, which will bind to the probe fixed to the support as explained, by sequence homology, such that the more labeled mRNA that binds to at one point, which corresponds to the specific probe of a gene, the more light will be detected at that point and it is therefore concluded that said gene is the most active.

Having established the operation of the microarray object of the invention, and having delimited the receptivity expression pattern for evaluating the receptivity/non-receptivity state of an endometrium by means of bioinformatic methods, the receptivity states of other pathological processes resulting in infertility or subfertility of an endometrial origin, such as implantation failure due to an endometrial cause and hydrosalpinx, can also be evaluated using the same method.

In addition to the use of the microarray of the present invention for molecular diagnosis, the latter can also be used as a biotechnological tool for studying the possible effect of drugs and/or inert devices in the endometrium, such as for example the response to contraceptive drugs, both in in vitro and in vivo assays.

More specifically, the microarray of the present invention is suitable for determining from a biological sample of human endometrium the normalcy/abnormality situation in the receptive profile of said endometrium, because the microarray is a customized expression microarray which analyzes the mRNA set of the biopsy. The receptivity expression profile is defined and classified to that end and using a computational prediction model. It is also capable of defining the normal receptivity state and other situations of receptivity, both subfertility and infertility, as well as the exposure to drugs and/or inert devices, because software is used to analyze the microarray which contains the necessary information so that from an endometrial biopsy obtained during the receptive period and after being analyzed by the ERA, the gene expression data are preprocessed, such that the sample is classified in the class determined by the prediction model.

The microarray of the present invention is an oligo expression microarray with an 8×15K format (8 arrays of 15,000 probes) per slide (FIG. 3). Each array contains 15,744 points: 569 probes in which are included the selected genes (8 replicas per probe, 4552 points), 536 control points and 10656 free (empty) points.

BRIEF DESCRIPTION OF THE FIGURES

FIGS. 1A-1J show a list of the 569 probes corresponding to the 238 genes with an FDR<0.05 and an FC>3, which are those which have been selected and are specified in FIGS. 2A-2R.

FIGS. 2A-2R show a list of the 238 genes selected with an FDR<0.05 and an FC>3.

FIG. 3 shows a specific microarray (ERA) (Agilent Technologies). The figure shows how the ERA, oligo expression microarray, has a format of 8×15K (8 arrays with 15,000 probes) per slide. Each array contains 15,744 points: 569 probes in which the selected genes are included (8 replicas per probe, 4,552 points), 536 control points and 10656 free (empty) points.

FIG. 4 shows a table in which the forward and reverse primers designed from the genes to be amplified by means of quantitative PCR are shown.

FIG. 5 shows the mean expression of the probes of each gene in the array compared with the expression in the quantitative PCR.

FIG. 7 shows the result of a computational prediction model generated with a training set of 23 samples having the described characteristics, which have been analyzed with the ERA. A. The prediction model distinguishes between two classes, Receptive (samples on day 20-21) and Other (samples on days of the cycle outside receptivity). The rows show each of the samples analyzed with the ERA array, and column 1 shows the actual class known a priori and column 2 shows the class assigned by the prediction model. It is observed that it predicts with a 100% success rate after calculating the error by cross-validation. B. Confusion matrix in which it is seen that 11 samples are classified as other days of the cycle and 12 samples are classified as receptive, there being no false positives or false negatives.

DETAILED DESCRIPTION OF THE INVENTION

Figure 6:
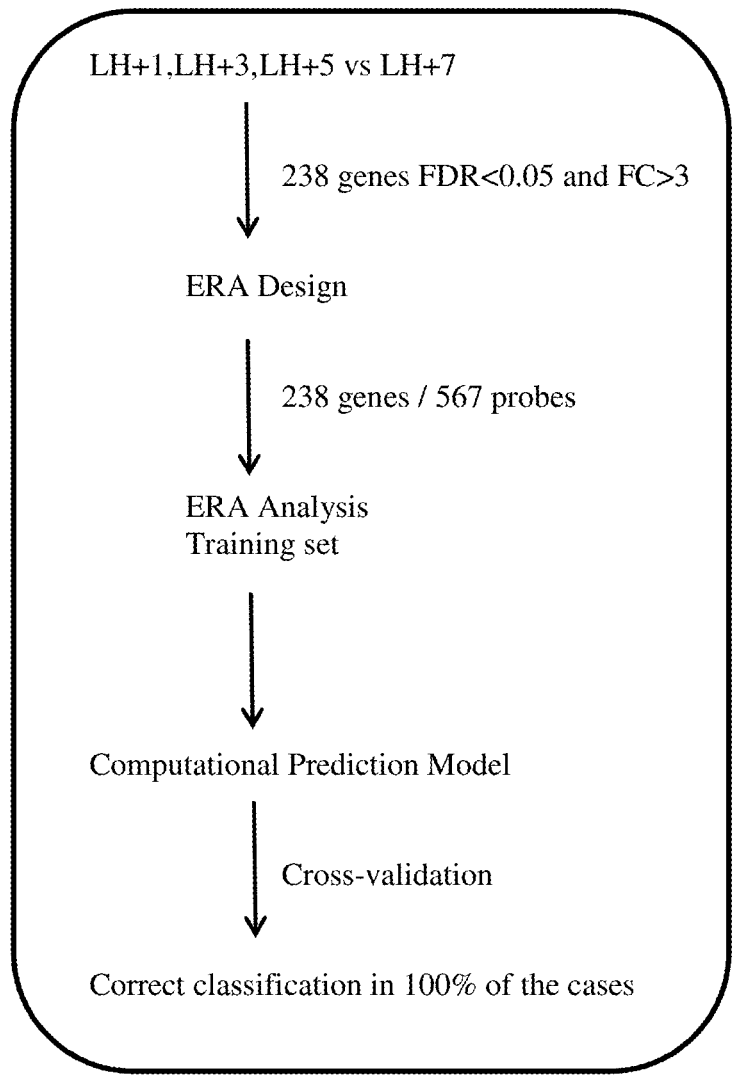
FIG. 6 shows a diagram summarizing how the molecular tool and the main components which form it have been designed.

Endometrial receptivity is the state in which the endometrium is prepared for embryo implantation. This occurs in all menstrual cycles in a time period referred to as window of implantation, which has a variable duration and opens around day 19 of the cycle and closes on day 24, day 21 being considered a reference day.

Ovulation occurs after the luteinizing hormone (LH) surge, which occurs around day 14. A more exact way to know the actual moment in the menstrual cycle is to measure this LH surge in blood, the day it occurs being considered as day LH 0 and day 15 of the cycle LH+1 and day 21 of the cycle LH+7.

A molecular diagnostic tool allows analyzing the transcriptome of a subset of genes of the genome related to the receptivity status.

After taking an endometrial biopsy on day 21 of the menstrual cycle (receptive phase, LH+7), it can be evaluated whether the woman has a normal receptive endometrium or whether, on contrast, the expected expression pattern is not shown.

Figure 8:
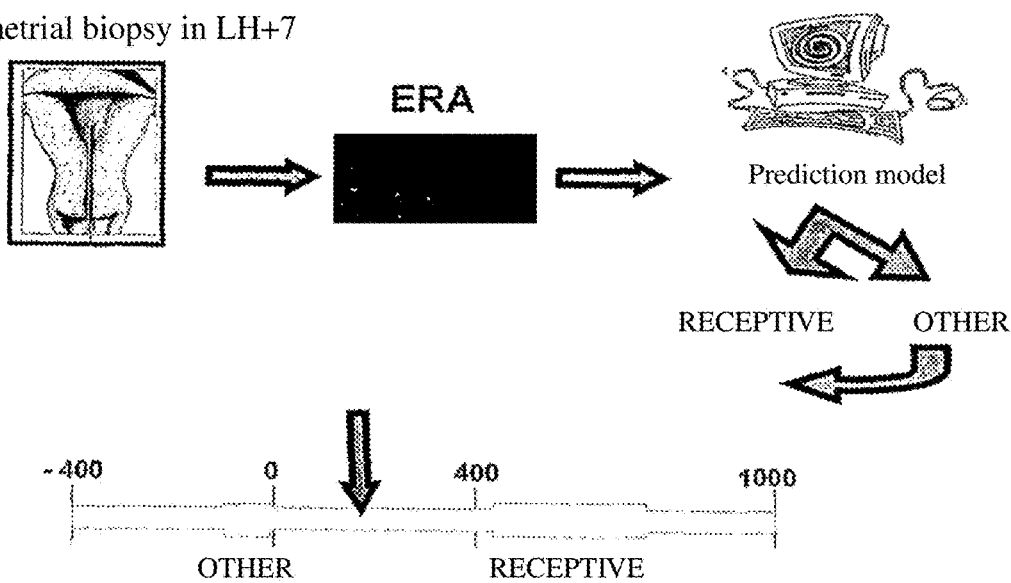
FIG. 8 shows a diagram of the process to be followed for determining the state of endometrial receptivity of a woman.

The endometrial biopsy is processed to extract its RNA, and this labeled RNA will hybridize with the probes fixed in the ERA, being able to detect the expression levels of the genes depending on the intensity of each point by means of a scanner. The data of the intensities of each point are analyzed by the prediction model which has previously been trained, and this model, depending on the entire set of points, classifies the samples as normal receptive samples or outside of normalcy samples (FIG. 8).

The prediction model is a mathematical system using different algorithms, formulas, to distinguish between classes, and is trained with the training set to define the normal receptivity profile, and to define the receptivity profile of endometrial pathologies or status of subfertility due to endometrial causes which cause implantation failure; such as endometriosis, hydrosalpinx, etc.

1. Identifying the genes involved in endometrial receptivity for generating the specific microarray of endometrial receptivity.

The first phase of the project consists of identifying the genes which are specifically regulated in the endometrium of day LH+7 and which will be part of the customized microarray.

In most published works, the mentioned genes have been selected when they are induced or suppressed two times. Different and stricter selection criteria have been followed in the present invention:

Gene Selection Criterion.

The genes have been selected based on the differences of the endometrial gene expression profile represented by LH+1, LH+3 and LH+5 (non-receptive) against LH+7 as the receptive state. The expression levels have been obtained from a whole genome oligo expression microarray. Those genes showing significant differences of expression in these two situations have been chosen using the criteria of FDR<0.05* and FC>3**.

* FDR: False Discovery Rate. This parameter corrects the P-value depending on the size of the sample. The value of FDR 0.05 is the significance that is typically taken into account at the statistical level and involves running a 5% risk that the differences are due to chance and not to the biological process in question.

** FC: Fold change. This means the number of times that the expression of a gene changes in one situation with respect to another. With regard to FC>3, the criterion is to assume that if it changes more than three times, it is sufficient change to consider the gene important for the process.

The possibility that the differences of expression may be due to chance and not to the biological process has been considered with FDR. Furthermore, the genes with an Fc above a threshold value of 3 have been selected so that the final number of genes worked with is feasible. More importance is therefore given to the genes which change the most because a directly proportional ratio between more changes and greater importance for the process is assumed. This strict criterion combines both the statistical and the biological requirement. Furthermore, the functional sense of this gene selection has receptivity. To that end, the genes were ontologically classified by means of bioinformatic tools using FATIGO GEPAS (Al-Shahrour F et al., 2005) given that the biological processes represented in a manner exceeding what is expected with a significance of 0.05 are the response to stress, the defense response and cell adhesion, which are fairly relevant processes in preparing an endometrium for the possible implantation of the blastocyst.

Those genes with these characteristics have been chosen and this has resulted by means of computer programs in a total of 238 genes (FIGS. 2A-2R) represented by 569 probes (FIGS. 1A-1J).

2. Creating the specific microarray (Era) (Agilent Technologies)

The ERA is an oligo expression microarray with a format of 8×15K (8 arrays of 15,000 probes) per slide (FIG. 3). Each array contains 15,744 points: 569 probes in which the selected genes are included (8 replicas per probe, 4,552 points), 536 control points and 10,656 free (empty) points.

Expression analysis by means of the ERA

In this section, the expression data generated by the ERA for classifying the endometrial samples in two or more classes according to the different receptivity profiles that are generated (normal receptive; pathological receptive; normal non-receptive . . . ) are used to generate the prediction model and to check its efficacy.

To that end, endometrial biopsies of fertile women are selected. All the independent samples are from women with proven fertility on different days of the menstrual cycle. They are Caucasian women with a body mass index between 19 and 25 kg/m² and whose ages range between 18 and 35 years old.

Said samples were used to generate a prediction model.

To that end, the total RNA was extracted using the Trizol protocol (Invitrogen) following the manufacturer's instructions (Life Technologies, Inc., USA). The samples were homogenized using 1 ml of trizol for each 75 mg of tissue, they were incubated at room temperature for 5 minutes, and 200 µl of chloroform were added for the same amount of tissue and were incubated at room temperature for 5 minutes. They were then centrifuged for 15 minutes at 12,000×g (4° C.). The aqueous phase was precipitated with an equal volume of 2-propanol (isopropanol), it was incubated on ice for 5 minutes and centrifuged for 30 minutes at 12,000×g (4° C.). The precipitate was washed with 70% ethanol in water treated with diethylpyrocarbonate (DEPC) to subsequently resuspend it in water-treated DEPC (15 µl). This protocol usually produces 1-2 µg of total RNA per mg of endometrial tissue. The RNA thus extracted is treated with DNase for 1 hour at 37° C. to remove the traces of DNA and purify it again using the Qiagen RNeasy kit following the manufacturer's instructions. The RNA that is obtained after the columns of the RNeasy kit is analyzed to check its quality in the Agilent 2100 bioanalyzer using the Agilent brand RNA specific chips, RNA Nano LabChip.

Only those RNAs having the following characteristics have been used for subsequent analyses:

They did not have detectable genomic DNA,
They had a concentration greater than 200 µg/ml,
The value of the radius of rRNA was 28s/18S>1.2, and
The RIN (RNA Integrity Number) value>7.0.

After the analyses with the samples selected due to their suitable quality, single-stranded complementary DNA (cDNA) is generated from the total RNA by incubating it between one and two hours at 40° C. with reverse transcriptase, nucleotides and an oligonucleotide polydT-T7, which has not only the poly T sequence which hybridizes with the polyA tail of messenger RNA, but also the recognition sequence for T7 RNA polymerase.

The cDNA obtained in the previous step is incubated for 2 hours at 40° C. in the presence of T7 RNA polymerase and nucleotides, one of which is labeled with Cy3, to produce complementary RNA called cRNA.

That cRNA is purified by means of a purification kit based on affinity chromatography and is quantified.

Once purified, that labeled cRNA is fragmented for 30 minutes at 60° C. and hybridized in the microarray for 17 hours at 65° C. Once that time has elapsed, the microarray is washed to remove unspecific hybridizations. Once hybridized and washed, the microarrays are centrifuged at 3,000 rpm for 3 minutes to dry the microarrays and they are then read by means of scanning them in an Axon GenePix 4100A, reading for Cy3 intensities (532 nm).

As a result, after the relevant data processing enclosed below, a gene expression matrix was generated the rows of which correspond to the 569 probes of the 238 genes selected and the columns of which correspond to the different samples.

Processing the Data of the Array

The correction of the bottom effect has been done by subtracting half the median of the latter from the intensity of the point. Interarray normalization has been done using the quantile method.

The mean of the eight replicas of each probe is then calculated. The different probes of the same gene (probe set) are analyzed individually and the results are processed by bioinformatic tools.

Validating the Results of the ERA by Means of PCR

The results obtained in the ERA have been validated by means of quantitative PCR for the purpose of giving the results greater consistency and checking that the microarray analysis is reliable.

Reverse transcription is performed to obtain RNA in the form of cDNA, to that end 1 µg of total RNA was placed in the presence of 1 µg oligo (dT) (Clontech) until reaching a final volume of 12.5 µl with water treated with DEPC (diethylpyrocarbonate). It was heated for 2 minutes at 70° C. so that any possible secondary structure in the mRNA would denature, and it was then kept on ice for 2 minutes.

Then 6.5 µl of a MIX solution with 4 µl of buffer, 1 µl dNTP, 0.5 µl RNase and 1 µl of reverse transcriptase (Rt-PCR Clontech) were added for each of the 30 samples to be validated. The reverse transcription lasted for 1 hour in the thermal cycler. 80 µl of water with DEPC are added and concentration of single-stranded cDNA obtained is measured by spectrophotometry placing 2 µl of sample and 98 µl of DEPC-treated water. The amount of cDNA that has been reverse transcribed must be between 80 to 120 ng/µl to start from similar concentrations, though it is normalized with the internal pattern, in our case GAPDH. In any case, in order for the quantitative PCR to work correctly, the range of cDNA to be amplified must be between 50-500 ng/µl. If any sample is not within those parameters, it is diluted.

The forward and reverse primers were designed for five genes with increased LH+7 (FIG. 4). The oligonucleotide sequences of the primers were designed with the GeneFisher bioinformatic program (see FIG. 4 and sequence listing). The detection system was performed with SYBR Green I binding to double-stranded DNA (Roche). This detection system establishes a linear dynamic range for detecting specific PCR products. All the Q-PCR experiments were conducted using the SYBR Green PCR Master Mix (Roche) and the universal conditions of the thermal cycle parameters indicated by the manufacturers using the Roche Light Cycler. 40 cycles were performed. The temperatures at which the primers work well can be observed in FIG. 4. The relative quantification was performed by means of the standard master curve method.

The expression of GPX3; CLDN10; FXYD2; SPP1; and MT1G, correspond in the ERA to the expression values of the following probes:

| Probe | Gene |
|---|---|
| A_23_P133474 | GPX3 |
| A_23_P133475 | GPX3 |
| A_01_P007324 | CLDN10 |
| A_23_P48350 | CLDN10 |
| A_24_P196562 | FXYD2 |
| A_23_P161769 | FXYD2 |
| A_23_P7313 | SPP1 |
| A_01_P017618 | SPP1 |
| A_23_P60933 | MT1G |
| A_23_P206707 | MT1G |
| A_23_P206701 | MT1G |

Considering that these are different techniques, quantitative PCR, the sensitivity of which is much higher but it only provides one expression value, and the arrays in the which there is expression of different probes for one and the same gene, in order to make the comparison, the mean expression of the different probes of a gene has been calculated in the array (FIG. 5).

Due to the different sensitivity, it is considered that the ratio of the expression value between both techniques would correspond to a correction factor of 10 (augmented expression 10× in the array) it is accepted that they correspond with a maximum of 100× in the quantitative PCR (FIG. 5).

3. Analyzing the expression pattern of the ERA during the window of implantation to be able to establish the endometrial receptivity profile. Generating a classifier.

Training

A predictor is a mathematical tool which uses a data matrix, in this case of the data generated with the ERA, and learns to distinguish classes (Medina I, et al., 2007), in this case two or more classes according to the different receptivity profiles that are generated (normal receptive; pathological receptive; normal non-receptive . . . ). The underlying reasoning for this strategy is the following: if it is possible to distinguish among the classes as a consequence of the level of gene expression, it is then in theory possible to find the characteristic gene expression of LH+7 and to use it to assign a class to the expression profile of the test sample analyzed with the customized ERA microarray.

The set of samples which trains the classifier to define the classes is referred to as training set. In other words, the gene expression profiles of these samples, measured with the ERA, are used by the program to know which probes are the most informative and to distinguish between classes (different normal non-receptive and receptivity states). The biopsies used to generate the classification model are carefully chosen and dated in the most reliable manner currently available. This training set will gradually grow as a larger number of samples are tested, but it is made up of receptive samples and on other days of the menstrual cycle. They are all independent samples from different healthy women in the natural cycle and with proven fertility. They are Caucasian women with a body mass index between 19 and 25 kg/m$^2$ and between 19 and 34 years old. Only those samples the histological dating of which, by applying Noyes criteria, coincides between the two pathologists and with the day of the menstrual cycle have been chosen.

The classification is done by the bioinformatic program using different mathematical algorithms, there being many available. An algorithm is a well defined, ordered and finite list of operations which allows solving a problem. A final state is reached through successive and well-defined steps given an initial state and an input, obtaining a solution.

The classifier calculates the error committed by means of a process called cross-validation, which consists of leaving a subset of the samples of the training set of a known actual class out of the group for defining the classes, and then testing them with the generated model and seeing if it is right. This is done by making all the possible combinations. The efficacy of the classifier is calculated and prediction models are obtained which correctly classify all the samples of the training set (FIG. 5). In other words, all the samples of the training set are classified by the predictor in the assigned actual class known by the inventors.

A priori, it is impossible to know how the data are distributed in space, it is only possible to know how they are located in the dimensions that can be distinguished, there being three of them. Therefore, there are different algorithms to be applied which would work better or worse depending on how the entered data are distributed in space. The algorithms most widely used in mathematics for expression matrices generated by microarray analysis are applied, and the one that best separates the defined classes is observed. Therefore, there are algorithms which establish a separation according to a straight line, others do so depending on the closest nearby point, based on distances . . . and thus each method is based on a mathematical separation criterion which will more or less fit the reality of the samples.

4. Developing a predictor which allows quantitatively and objectively evaluating and predicting the endometrial receptive state based on the gene expression profile.

Determining the Prediction

Depending on all the parameters relating to a computational predictor explained above, a prediction model is generated which classifies all the samples according to the assigned actual class, which in turn was dated by Noyes, there being a 100% coincidence (FIG. 7).

The generated prediction model has been trained with a training set of 23 samples, 12 receptive samples and 11 on other days of the menstrual cycle, two classes (receptive/Other) being distinguished. After that, the model will be re-trained as more samples of the same characteristics of the already generated training set are obtained, but also with samples in a receptivity period with pathologies altering the expression pattern of the ERA, as well as the alteration by drugs. Increasingly more classes will thus be gradually defined.

Therefore, the ERA can be used for the positive identification of the endometrial receptivity, as well as for the diagnosis of the alteration thereof associated with endometrial alterations typical of pathologies such as endometriosis, implantation failure, hydrosalpinx, etc. This diagnostic tool would also allow detecting functional modifications induced by interceptive drugs or drugs which intend to improve endometrial receptivity, altering the normalcy/abnormality situation in the receptive profile of the endometrium of a woman.

Therefore, the ERA of the present invention is a customized gene expression microarray. It is a 60-mer oligo array with 8 arrays per slide, with 15K (15744 points) in each array.

It is a customized array with design number 016088 (AMADID). It has 569 probes represented by 238 genes with 8 replicas for each probe, for a total of 4,536 points, 10,672 of which are free points.

Reading the expression profile of the expression data for 238 genes represented by 569 probes (genes with an FDR>0.05 and an FC>3) is a prediction model constructed with 23 samples classified with an error of 0, which is capable of classifying the sample as receptive state or other.

The statistical analyses as well as the selection of genes with the indicated characteristics were done using computer programs.

The final list of the ERA includes the 569 probes representing the 238 genes with an FDR<0.05 and an FC>3 (FIGS. 1A-1J).

The customized ERA array is hybridized with the messenger RNA of another set of samples different from those used to select the genes to be included, which are used to teach the predictor how to classify between LH+7 or another.

After defining these two classes, receptive or outside, the predictor will be scaled, i.e., it will determine how close or far the profile of a sample is from the receptive profile.

EXAMPLE

Obtaining and Processing the Samples

Biopsies of the endometrium were taken in 30 healthy female donors with proven fertility, and from 10 patients in a clinic with implantation failure due to an endometrial cause, the 4$^{th}$ biopsies being taken on day 21 of the menstrual cycle (receptive phase, LH+7).

The total RNA of each of the biopsies is extracted using the Trizol protocol (Invitrogen) following the manufacturer's instructions (Life Technologies, Inc., USA). The samples are homogenized using 1 ml of Trizol for each 75 mg of tissue, they are incubated at room temperature for 5 minutes, and 200 µl of chloroform are added for the same amount of tissue and are incubated at room temperature for 5 minutes. They are then centrifuged for 15 minutes at 12,000×g (4° C.). The aqueous phase is precipitated with an equal volume of 2-propanol (isopropanol), it is incubated on ice for 5 minutes and centrifuged for 30 minutes at 12,000×g (4° C.). The precipitate is washed with 70% ethanol in water treated with diethylpyrocarbonate (DEPC) to subsequently resuspend it in DEPC-treated water (15 µl). This protocol usually produces 1-2 µg of total RNA per mg of endometrial tissue. The RNA thus extracted is treated with DNase for 1 hour at 37° C. to remove the traces of DNA and purify it again using the Qiagen RNeasy kit following the manufacturer's instructions. The RNA that is obtained after the columns of the RNeasy kit is analyzed to check its quality in the Agilent 2100 bioanalyzer using the Agilent brand RNA specific chips, RNA Nano LabChip.

Only those RNAs having the following characteristics can be used:
they did not have detectable genomic DNA,
they had a concentration greater than 200 µg/ml,
the value of the radius of rRNA was 28s/18S>1.2, and
the RIN (RNA Integrity Number) value>7.0.

After the analyses with the samples selected due to their suitable quality, single-stranded complementary DNA (cDNA) is generated from the total RNA by incubating it between one and two hours at 40° C. with reverse transcriptase, nucleotides and an oligonucleotide polydT-T7, which has not only the poly T sequence which hybridizes with the polyA tail of messenger RNA, but also the recognition sequence for T7 RNA polymerase.

The cDNA obtained in the previous step is incubated for 2 hours at 40° C. in the presence of T7 RNA polymerase and nucleotides, one of which is labeled with Cy3, to produce complementary RNA called cRNA.

That cRNA is purified by means of a purification kit based on affinity chromatography and is quantified.

Once purified, that labeled cRNA is fragmented for 30 minutes at 60° C. and hybridized in the microarray for 17 hours at 65° C. Once that time has elapsed, the microarray is washed to remove unspecific hybridizations. Once hybridized and washed, the microarrays are centrifuged at 3,000 rpm for 3 minutes to dry the microarrays and they are then read by means of scanning them in an Axon GenePix 4100A, reading for Cy3 intensities (532 nm).

As a result, after the relevant data processing enclosed below, a gene expression matrix is generated the rows of which correspond to the 569 probes of the 238 genes selected and the columns of which correspond to the different samples.

Processed of the Data of the Array

The data of the array is processed by a series of bioinformatic commands which are in software designed exclusively for the invention as is explained below.

The correction of the bottom effect in the 40 data matrices due to the labeling process typical of the technique is performed.

The empty points are then removed and the normalization process is performed depending on the 40 samples and depending on the expression profile defined according to the prediction model so that it can be compared.

The mean of the eight replicas of each probe is then calculated. The different probes of the same gene are analyzed individually and the results are analyzed by the computational created prediction model which is also included in the software.

Prediction

The 40 samples to be tested (test set) are run with the created classification model which analyzes the expression of the ERA and predicts which class they belong to.

Results

The analysis of the expression data of the array was entered in the software. The obtained result indicated that out of the 30 tested samples from healthy women with proven fertility, 27 corresponded to women with an receptivity expression profile of the endometrium considered as normal and corresponding to women with an receptivity expression profile of the endometrium considered as outside of normalcy. Nine out of the 10 patients with implantation failure were classified as outside of normal receptivity and 1 was classified as within normal receptivity. The molecular tool presented a 90% diagnostic efficacy.

LITERATURE

Al Shahrour F and Dopazo J. In Azuaje F and Dopazo J (eds), Data analysis and visualization in genomics and proteomics. Wiley 2005; 99-112.

Al-Shahrour F, Minguez P, Vaquerizas J M, Conde L and Dopazo J. BABELOMICS: a suite of web tools for functional annotation and analysis of groups of genes in high-throughput experiments. Nucleic Acids Res 2005; 33:460-464, Balasch J, Fabregues F, Creus M and Vanrell J A. The usefulness of endometrial biopsy for luteal phase evaluation in infertility. Hum Reprod 1992; 7:973-977.

Batista M C, Cartledge T P, Merino M J, Axiotis C, Platia M P, Merriam G R. Midluteal phase endometrial biopsy does not accurately predict luteal function. Fertil Steril 1993; 59:294-300, Borthwick J, Charnock-Jones S, Tom B D et al, (2003) Determination of the transcript profile of human endometrium. Mol Hum Reprod 9, 19-33, Carson D, Lagow E, Thathiah A et al, (2002) Changes in gene expression during the early to mid-luteal (receptive phase) transition in human endometrium detected by high-density microarray screening. Mol Hum Reprod 8, 971-979.

Catalano R D, Yanaihara A, Evans A L, Rocha D, Prentice A, Saidi S, Print C G, Charnock-Jones D S, Sharkey A M and Smith S E (2003) The effect of RU486 on the gene expression profile in an endometrial explant model Mol Human Reprod 9, 465-473.

Coutifaris C, Myers E R, Guzick D S, Diamond M P, Carson S A, Legro R S, McGovern P G, Schlaff W D, Carr B R, Steinkampf M P, Silva S, Vogel D L and Leppert P C. Histological dating of timed endometrial biopsy tissue is not related to fertility status. Fertil Steril 2004; 82:1264-72.

Creus M, Ordi J, Fabregues F, Casamitjana R, Ferrer B, Coll E, Vanrell J A and Balasch J. Alphavbeta 3 integrin expression and pinopod formation in normal and out-of-phase endometria of fertile and infertile women. Hum Reprod 2002; 17:2279-2286, Horcajadas J A, Sharkey A M, Catalano R D, Sherwin J R A, Dominguez F, Burgos L A, Castro A, Peraza M R, Pellicer A and Simòn C (2006) Use of Gene-Expression Profiling to Identify Human Endometrial Refractoriness. J Clin Endocrinol Metabol.

Horcajadas J A, Pellicer A and Simòn C (2007) Wide Genomic Analysis of Human Endometrial Receptivity. New times, new opportunities. Human Reprod Update 13, 77-86, Horcajadas J A, Riesewijk A, Polman J, van Os R, Pellicer A, Mosselman S and Simòn, C (2005) Effect of Controlled Ovarian Hyperstimulation in IVF on Endometrial Gene Expression Profiles. Mol Human Reprod 11, 195-205.

Kliman H J, Honig S, Walls D, Luna M, McSweet J C, Copperman A B. Optimization of endometrial preparation results in a normal endometrial function test (EFT) and good reproductive outcome in donor ovum recipients. J Assist Reprod Genet 2006; 23:299-303.

Lessey B A, Castelbaum A J, Sawin S W, Sun J. Integrins as markers of uterine receptivity in women with primary unexplained infertility. Fertil Steril 1995; 63:535-542.

Li T C, Dockery P, Rogers A W and Cooke I D. (How precise is histologic dating of endometrium using the standard dating criteria?. Fertil Steril 1989; 51:759-763, Medina I, Montaner D, Tarraga J, Dopazo J. Prophet, a web-based tool for class prediction using microarray data. Bioinformatics. 2007; 23(3):390-1.

Mirkin S, Arslan M, Churikov D, Corica A, Diaz Jl, Williams S, Bocca S and Oehninger S (2005) In search of candidate genes critically expressed in the human endometrium during the window of implantation Human Reprod 20:2104-2117.

Mirkin S, Nikas G, Hsiu J G, Diaz J and Oehninger S (2004) Gene expression profiles and structural/functional features of the peri-implantation endometrium in natural and gonadotropin-stimulated cycles. J Clin Endocrinol Metab 89:5742-5752.

Montaner D, Tárraga J, Huerta-Cepas J, Burguet J, Vaquerizas J M, Conde L, Minguez P, Vera J, Mukherjee S, Valls J, Pujana M A G, Alloza E, Herrero J, Al-Shahrour F and Dopazo J. Next station in microarray data analysis: GEPAS. Accepted Nucleic Acids Res. 2006, Murray M J, Meyer W R, Zaino R J, Lessey B A, Novotny D B, Ireland K, Zeng D and Fritz M A. A critical analysis of the accuracy, reproducibility, and clinical utility of histologic endometrial dating in fertile women. Fertil Steril 2004; 81:1333-1343, Noyes R W, Hertig A T, and Rock J. Dating the endometrial biopsy. Fertil Steril 1950; 1:3-17.

Ordi J, Creus M, Quinto L, Casamitjana R, Cardesa A and Balasch J. Within-subject between-cycle variability of histological dating, alpha v beta 3 integrin expression, and pinopod formation in the human endometrium. J Clin Endocrinol Metab 2003; 88:2119-2125, Papanikolaou E G, TouARNye H, Verpoest W, Camus M, VeARNeve V, Van Steirteghem A, Devroey P; http://www.ncbi.nlm.nih.gov/sites/entrez?Db=pubmed&Cmd=ShowDetailView&TermToSearch=15576388&ordinalpos=79&itool=EntrezSystem2.PEntrez.Pubmed.Pubmed_ResultsPanel.Pubmed_RVDocSum Early and late ovarian hyperstimulation syndrome: early pregnancy outcome and profile. Hum Reprod. 2005; 20(3):'636-641.

Ponnampalam A P, Weston G C, Trajstman A C. Molecular classification of human endometrial cycle stages by transcriptional profiling. Mol Hum Reprod 2004; 10, 879-893, Riesewijk A, Martin J, Horcajadas J A Polman J, Pellicer A, Mosselman S and Simón C (2003) Gene expression profiling of human endometrial receptivity on days LH+2 contra LH+7 by microarray technology. Mol Hum Reprod 9:253-264, Schena M, Shalon D, Davis R W and Brown P O. Quantitative monitoring of gene expression patterns with a complementary DNA microarray. Science 1995; 270:467-470, Sharkey A M, Catalano R, Evans A, Charnock-Jones D S and Smith S K (2005) Novel antiangiogenic agents for use in contraception. Contraception 71, 263-271.

Shoupe D, Mishell D R Jr, Lacarra M, Lobo R A, Horenstein J, d'Ablaing G. Correlation of endometrial maturation with four methods of estimating day of ovulation. Obstet Gynecol. Obstet Gynecol 1989; 73:88-92.

Talbi S, Hamilton A E, Vo K C, Tulac S, Overgaard M T, Dosiou C, Le Shay N, Nezhat, C N, Kempson R, Lessey B A, Nayak N R and Giudice L C. Molecular phenotyping of human endometrium distinguishes menstrual cycle phases and underlying biological processes in normo-ovulatory women. Endocrinology 2005; 147:1097-1121.

Wilcox A J, Baird D D, Weinberg C R. Time of implantation of the conceptus and loss of pregnancy. N Engl J Med. 1999; 340:1796-1799.

T-REX (http://www.gepas.org/)
FATIGO (http://babelomics.bioinfo.cipf.es/EntryPoint?loadForm=fatigo)
PROPHET (http://gepas.bioinfo.cipf.es/cgi-bin/loadtool.cgi?tool=prophet)
Agilent earray 4.5 (https://earray.chem.agilent.com/earray/)

The invention claimed is:

1. A method for detecting endometrial receptivity to embryo implantation in a human subject, the method comprising:
   (a) performing an assay on an endometrial sample from the human subject to determine a gene expression profile of the sample, wherein the gene expression profile comprises the genes listed in FIG. 2;
   (b) determining that the human subject has endometrial receptivity based on a fold change greater than or equal to about three for expression of the genes in the gene expression profile when compared to a non-receptive endometrial sample; and
   (c) transferring an embryo to the endometrium of the human subject determined to have endometrial receptivity.

2. The method of claim 1, wherein the endometrial sample is obtained from the fundus of the uterus of the human subject.

3. The method of claim 1, wherein the endometrial sample is obtained after an endogenous luteinizing hormone (LH) surge in the human subject.

4. The method of claim 1, wherein the gene expression profile is measured using any of the oligonucleotides set forth as SEQ ID NOs: 1-579 or with any of the oligonucleotides listed in FIG. 4.

5. The method of claim 1, wherein the gene expression profile is measured using quantitative PCR (qPCR).

6. The method of claim 1, wherein the non-receptive sample is a sample obtained 1, 3, or 5 days after an endogenous luteinizing hormone (LH) surge in the human subject.

7. A method for detecting endometrial receptivity to embryo implantation in a human subject, the method comprising:
   (a) performing an assay on an endometrial sample from the human subject to determine a gene expression profile of the sample, wherein the gene expression profile consists essentially of genes listed in FIG. 2 in an endometrial sample from the human subject;
   (b) determining that the human subject has endometrial receptivity based on a fold change greater than or equal to about three for expression of the genes in the gene expression profile when compared to a non-receptive endometrial sample; and
   (c) transferring an embryo to the endometrium of the human subject determined to have endometrial receptivity.

8. The method of claim 7, wherein the endometrial sample is obtained from the fundus of the uterus of the human subject.

9. The method of claim 7, wherein the endometrial sample is obtained after an endogenous luteinizing hormone (LH) surge in the human subject.

10. The method of claim 7, wherein the gene expression profile is measured using any of the oligonucleotides set forth as SEQ ID NOs: 1-579 or with any of the oligonucleotides listed in FIG. 4.

11. The method of claim 7, wherein the gene expression profile is measured using quantitative PCR (qPCR).

12. The method of claim 7, wherein the non-receptive sample is a sample obtained 1, 3, or 5 days after an endogenous luteinizing hormone (LH) surge in the human subject.

* * * * *

```
                             SEQUENCE LISTING

<160> NUMBER OF SEQ ID NOS: 579

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
ctggaaggtg tctaccatcg a                                              21

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 2
aaagaagccc aggctgaca                                                 19

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
taaaccctga cccatctcag a                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
tgagactcat cagactggtg a                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
aatgactggg ttgtcgatgg a                                              21

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
```
acagcggaat cttctgctga                                                        20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
tcctgcaagt gcaaagagtg                                                        20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
ggaatgtagc aaagggtca                                                         20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
aggtggaggc tttgtcccta                                                        20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
tataccatct ggccccacca                                                        20

<210> SEQ ID NO 11
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 11
gaaggtgaag gtcggagtc                                                         19

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
gaagatggtg atgggatttc                                                        20

<210> SEQ ID NO 13
<211> LENGTH: 60
<212> TYPE: DNA

<213> ORGANISM: Artificial Sequence
<220> FEATURE:
<223> OTHER INFORMATION: Synthetic oligonucleotide

<400> SEQUENCE: 13
gtaactgtgc tgaatgcttt agatgaggaa atgatcccca agtggtgaat gacacgccta    60

<210> SEQ ID NO 14
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 14
ggcgagattg aagggctttt gttattgttg ttggatattt ttgtttccca taaaagcaca    60

<210> SEQ ID NO 15
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 15
tttgaccgca gcatgcacaa gctccaaagt ggaattggcc ggctgattct gaaggaagaa    60

<210> SEQ ID NO 16
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 16
tttctggaag agattgcatc tgaggaaatt caggaaggat ctttgtagat tgggggagaa    60

<210> SEQ ID NO 17
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 17
tgtgttctca tgtaggatgt cagccctccc tgcaacttct cttttggcc aatgtctttt    60

<210> SEQ ID NO 18
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 18
aagccattca taaagaagc gtcaatggcc aaatactatg catcagagat tgcaggacaa    60

<210> SEQ ID NO 19
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 19
caacatccag ttgaacacca ttgcaaagca tatcgatgca gaatactgac gtctatagga    60

<210> SEQ ID NO 20
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 20
aattcagaaa ttgggttttg gttcagtgat tctcaagaaa aagatctctt gcccattaag    60

<210> SEQ ID NO 21
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 21
atcatgaagt gtgatattga catcaggaag gacctctatg ctaacaatgt cctatcaggg    60

<210> SEQ ID NO 22
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 22
accgcaaatg cttctaaaac actttcccgc tcctctctgt ctctagcaca caactgtgaa    60

<210> SEQ ID NO 23
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 23
acctctgagc agtgatatag cataataaag ccccgggcat tattattatt atttcttttg    60

<210> SEQ ID NO 24
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 24 tatggggta gatagaaaag gagttgaatc atcagagtaa actgccagtt gcaaatttga    60

<210> SEQ ID NO 25
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 25
ctttataagt attggtttgg gtgttccttc caagaaggac tatagttagt aataaatgcc    60

<210> SEQ ID NO 26
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 26
gaagaggaga ggggatgggg cgacagatcc tatcatcaac tgtccagtgg actggacctt      60

<210> SEQ ID NO 27
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 27
caccaattat ggctacaatg acattgtcac catcccagct ggtgccacta atattgacgt      60

<210> SEQ ID NO 28
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 28
atcatgtcat tgatgaactg ccaaagtcag gggaggaggg cagagacttt gtgtttacat      60

<210> SEQ ID NO 29
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 29
actacaagga catggctcac aaaaggttaa tggatggtta cctagaggat tacctagccc      60

<210> SEQ ID NO 30
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 30
ctcctcaatc tggtttatga acaactgac aaacacctt ctcctgatgg ccagtatgtc      60

<210> SEQ ID NO 31
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 31 tttttctct ttttggtggt ggttaaaagg gaacacaaaa catttaaata aactttcca      60

<210> SEQ ID NO 32
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 32
tcctcggaag acactctgac cgtggtcact gcggaccatt cccacgtctt cacatttggt      60

<210> SEQ ID NO 33
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 33
gctacaaggt ggtgggcggt gaacgagaga atgtctccat ggtggactat gctcacaaca    60

<210> SEQ ID NO 34
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 34
acctggaaga gcttcaaacc gagatacaag cactcccact tcatctggaa ccgcacggaa    60

<210> SEQ ID NO 35
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 35
tcttagcttt tagcactatt ggtaatttca gagtaggccc aaaggtgata tgactcccat    60

<210> SEQ ID NO 36
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 36
ggcccaaaga aagagctacc tggacctttt gttttctgtt tgacaacatg tttaataaat    60

<210> SEQ ID NO 37
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 37
agagctacct ggaccttttg ttttctgtct gacaacatgt ttaataaata aaaatgtcac    60

<210> SEQ ID NO 38
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 38
gtgtcatatt aggttaataa ggctgctgtg ttttaaaggg cattttattt tgggttttgg    60

<210> SEQ ID NO 39
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 39
ctcgtaacag cgaacggtca gtcaagggat cataagtttt tactgccagt attgagaaat    60

<210> SEQ ID NO 40
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 40 actttattc tttcaaagaa aatagactgc cattttccat caagattaga gacaccagcc    60

<210> SEQ ID NO 41
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 41
atcagcattc attgacacat agctctaatg acatatgtat gaaaaaccat acactggatg    60

<210> SEQ ID NO 42
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 42
tgttggaata ccggcggtga tctgtctttt ataaactcac ctgatttaaa ggaaagatga    60

<210> SEQ ID NO 43
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 43
agcacccgta aatggacttt ggtctcaatg ctttgactct ttgccgtggt tttggatgtt    60

<210> SEQ ID NO 44
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 44
aattaaaacg cctacagctg cctcctagaa tatagactgt ctgtattatt attcacctat    60

<210> SEQ ID NO 45
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 45
ctttctgctg tcaccttcgt cttgtcagaa tgaatataga cactgtatct aagtgggacc    60

<210> SEQ ID NO 46
<211> LENGTH: 60

```
<212> TYPE: DNA
<213> ORGANISM: Artificial Sequence
<220> FEATURE:
<223> OTHER INFORMATION: Synthetic oligonucleotide

<400> SEQUENCE: 46
ttggtttcct ctagggtgat attcgtcatt actctgtctc ttcaatccat ccagctaaat    60

<210> SEQ ID NO 47
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 47
ctgtccatct gtgcataagg agaggaaagt tccagggtgt gtatgtttca ggggcttcac    60

<210> SEQ ID NO 48
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 48
aatttgggtc aatacatcct tttgtctccc aagggaagag aatgggcagc aggtatgtgt    60

<210> SEQ ID NO 49
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 49
tttggtcaga caagagaagg agggcatatt gtctatgacc aacttcctac tcccagttca    60

<210> SEQ ID NO 50
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 50
tcaggttcca gtagttcatt ctaatgccta gattcttttg tggttgttgc tggcccaatg    60

<210> SEQ ID NO 51
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 51
ctagtcacat cccctgccag atggagttct tcttttgtga gagacactgt aaacaacaca    60

<210> SEQ ID NO 52
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 52
```
aagactggca aacagatggc aagggatgcc cctcttttc ataaaactct ccaaggttca    60

<210> SEQ ID NO 53
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 53
tggtgcatga attctcaagt actgtatttc actgtgttgg tgtgtctgat ggaaatttcg    60

<210> SEQ ID NO 54
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 54
gagcacttaa agtccagtgt tggctgttag tgtatttgat attctgcctg tctcctcatg    60

<210> SEQ ID NO 55
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 55
agaacgaata ccctatttag gttttaaaca gattaacctt tggactatgt ttcaagctgc    60

<210> SEQ ID NO 56
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 56
atgtagagat ccagtgttaa gagttccatt tgcttcaatt aattatttac cttcctgtgg    60

<210> SEQ ID NO 57
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 57
atcagggcat atacaaaagg gtttgttaaa actcgatgtt aactttacaa ctttctgacc    60

<210> SEQ ID NO 58
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 58
atcacaaatc ccctgcaagc tattcaaatg gtgatggata cgcttggcat tccttattag    60

<210> SEQ ID NO 59
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 59
tctttggaag ataacagtga tgtcacaggg ttggctatgt ttattctgaa tcgcctactt    60

<210> SEQ ID NO 60
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 60
aggccgagta agagagatta tgacatttct tgtaaatgat gttctgaaac accaagctat    60

<210> SEQ ID NO 61
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 61
atcacaaatc ccctgcaagc cattcaaatg gtgatggata cacttggcat tccttattag    60

<210> SEQ ID NO 62
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 62 gtgggggca gctgcggtgg ggagctataa aatgacaatt aaaagataca ctagtctttt    60

<210> SEQ ID NO 63
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 63
attgttgtga taatttgtaa ttgtgacttg ttctccccgg ctggcagcgt agtggggctg    60

<210> SEQ ID NO 64
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 64
tccctggagg atgcctgaat tctacaaccg gttcaagggc cgcaatgacc tgatggagta    60

<210> SEQ ID NO 65
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 65
tgtgaaggtg accaacgtca aggatggcac cacccaccag acctccttgg agctcttcat    60

<210> SEQ ID NO 66
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 66
aataattgcc aggagtacag tgctcttgtt gatcttgtat tcagtcaggt taaaacaatg    60

<210> SEQ ID NO 67
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 67
aactgtcata cgtatgggac ctacacttaa tctctatgct ttacactagc ttctgcattt    60

<210> SEQ ID NO 68
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 68
aataattgcc aggagtacag tgctcttgtt gatcttgtat tcagtcaggt taaaacaacg    60

<210> SEQ ID NO 69
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 69
tgggtggggg gttgtcatgg gggaactgcc ctttaaattt taagtgacac tacagaaaaa    60

<210> SEQ ID NO 70
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 70
tgaagcagag aaacattcac acacaaaaag caacatagtc atgtgggtcc agatggcctc    60

<210> SEQ ID NO 71
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 71
atgtgggtcc agatggcctc agtcctagat gttggcaccc tttgctgtgt ctcctcagag    60

<210> SEQ ID NO 72
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 72
tatgctcaga tattcatcgt aagtctccct tcacctgtta cagagtttca gatcggtcac    60

<210> SEQ ID NO 73
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 73
tttgtcctag gtgtaccctt tcctcatctc tattaaattg taaacaggac tactgcatgt    60

<210> SEQ ID NO 74
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 74
gtagaggaaa gggtgtgtga acatggctaa caatctcaaa tacccaaatt gtgatagcat    60

<210> SEQ ID NO 75
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 75
ttgatggatg ctacttctat ttgtggggaa ccttcaaaca ccatccaaag gacaacctta    60

<210> SEQ ID NO 76
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 76
gcacggtttg tgagagccca gtcattgtgc tgtttttaat ttttcacatt tttacaaata    60

<210> SEQ ID NO 77
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 77
ctgcgttaaa ggctcgattt tgtatctgca ggcagacacg gatctgagaa tctttattga    60

<210> SEQ ID NO 78
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 78
tttggctgtg tctaaactgc atcaccgcgt tgtaaaatat agctgtacaa atatcagaat    60

<210> SEQ ID NO 79

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 79
atcagcgtcc tatacattga aggtgtgcat atatgttgaa tgacatttta gggacatggt    60

<210> SEQ ID NO 80
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 80
tcctatacat cgaaggtgtg catatatgtt gaatgacatt tagggacat ggtgttttta     60

<210> SEQ ID NO 81
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 81
ctaaacaggc tcattacaaa tggttacctt gttatttaac ccatttgtct ctacttttcc    60

<210> SEQ ID NO 82
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 82
cacagtgtct gttcttgggg agcttgcagc agaaatgaat ggggttttg acactacatt     60

<210> SEQ ID NO 83
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 83
cgccccagca gtgtcctcag aacactctac tcgcacctcc cggtgatcca tgaactctga    60

<210> SEQ ID NO 84
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 84
aagaccaccg caggatgggc agcagagctc tgacctaaga agctggactt ttgggcagtc    60

<210> SEQ ID NO 85
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 85
```

```
tgtgttttct ctggagatag aatgtaaacc atattaaaag gaaaaagttt cagacaagca    60
```

<210> SEQ ID NO 86
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 86

```
gtaaaccaaa aacttttaaa tttcttcagg ttttctaaca tgcttaccac tgggctactg    60
```

<210> SEQ ID NO 87
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 87

```
tcgctagcac aaaatattgt cgctaatagt catttctgtt ttcccattgt aaatgctgtt    60
```

<210> SEQ ID NO 88
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 88

```
acacacgctt attgccgtgg caacagcggt agtgctaggg ggattaattt ttatagcatt    60
```

<210> SEQ ID NO 89
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 89

```
tcaacttaag cataaagggc tctgaacttt tccactttag agtgaccgtc atttcaggag    60
```

<210> SEQ ID NO 90
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 90

```
atgccaggac ctcggcacct tcactgagaa catggttgtc tttgggtgcc ccaactgacc    60
```

<210> SEQ ID NO 91
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 91

```
gtgccgctgt gctgaggaga attgcttcat acaaaagtcg gatgacaagg tcaccctgga    60
```

<210> SEQ ID NO 92
<211> LENGTH: 60
<212> TYPE: DNA

<210> SEQ ID NO 92
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 92
atgccaagac gaagagaacc agaaacaatg ccaggacctc ggcgccttca ccgagagcat    60

<210> SEQ ID NO 93
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 93
accgtgcctt atgcctgtgt gtgatcagtt tctggcacac agatgcctca ataaagattt    60

<210> SEQ ID NO 94
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 94
cctcttgcaa atcaatacag atcagtttag caaatctact gtcaatttgg cagtgatatt    60

<210> SEQ ID NO 95
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 95
ttctcaaaag aaggaggaaa aggtgtcttg ctggcttgcc tcttgcaatt caatacagat    60

<210> SEQ ID NO 96
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 96
gctggatgcc cttttgaagg atctgtacga gaaaacaaa aaggaaatga atattcaaca    60

<210> SEQ ID NO 97
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 97
gtagtactta gcctacctag accagcaagc attcattttt agctcgctca tttttacca    60

<210> SEQ ID NO 98
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 98
cttctgcagt gccttcacta cactgcctta cataaaccaa atcacaataa agttcatatt    60

<210> SEQ ID NO 99
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 99
gtggtgaata tcagtagttt gcagtgttta agggcttttg aaaactgcag tgaagatctg    60

<210> SEQ ID NO 100
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 100
caggtcatga ggtttcatta tcggcagtaa ctcgttgcac atgtttctag tggcaaaaaa    60

<210> SEQ ID NO 101
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 101
ttggtccatg acaaagttgt gcaaaactgg taaacgtctg cttcggagct tgctgcttaa    60

<210> SEQ ID NO 102
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 102
tgtgtagtta agcaccaaac agcagagaga acttagacac taccacacca agccttgtga    60

<210> SEQ ID NO 103
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 103
ttgattttgt acatagtcct ctggtctatc tcatgaaacc tcttctcaga ccagttttct    60

<210> SEQ ID NO 104
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 104
agtcctctgg tctatctcat gaaacctctt ctcagaccaa ttttctaaat atatattgag    60

<210> SEQ ID NO 105
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 105
ggcagaggac gggaggagac cagtccccca cccagccgta ccagaaataa aggcttctgt    60

<210> SEQ ID NO 106
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 106
catgtcccgc agccgctgca acacgctgtc ctcccccaac cagtaccagt gacccagtgg    60

<210> SEQ ID NO 107
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 107
gacaacctga ctatcaccat gcaccgcctg cagctgtcgg acactggcac ctacacctgc    60

<210> SEQ ID NO 108
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 108
atcagcctcc ccaaggttct gtcctgttcc gagcaacttt tctaattata aacatcacag    60

<210> SEQ ID NO 109
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 109
agaatgccca ctgcctgtaa cagccacctg gagaacttca taaagatgtc tcacagccct    60

<210> SEQ ID NO 110
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 110
cccatgtcaa aaacttggat gaaaatggct tggatttgct ctcgaaaatg ttaatctatg    60

<210> SEQ ID NO 111
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 111
tatcaaactt aagctgtact tcatcttcta atttcaaaag tataacttaa aaatgtaaat    60

```
<210> SEQ ID NO 112
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 112
atccaccaag gcatccgctg aagaccaacc catcacctca gttgtttttt attttctaa      60

<210> SEQ ID NO 113
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 113
ccgctgaaga ctaacccatc acctcagttg tttttatt ttctaataaa gtcatgtctc       60

<210> SEQ ID NO 114
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 114
ggtaatgata acttggtcaa tgtgtggcct agtgctcctg gagagggtgg ctgggttcct     60

<210> SEQ ID NO 115
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 115
ctgagtgcaa aactcagtag actcctcttt gtcacttctc tggagatcca gcattcctta     60

<210> SEQ ID NO 116
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 116
ggctttactt tgccactaga gttgaaatat aagggaacag gaaatgaatg cattgtggta     60

<210> SEQ ID NO 117
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 117
acctgaagag cttcaagctg aaaggaattt ccacactgtc ccctacatgg tcggaattaa     60

<210> SEQ ID NO 118
<211> LENGTH: 60
<212> TYPE: DNA
<213> ORGANISM: Artificial Sequence
<220> FEATURE:
<223> OTHER INFORMATION: Synthetic oligonucleotide
```

<400> SEQUENCE: 118
gagcaatgaa gtcatccact cctgcatctg gttggtcttt attgagcacc tactatatgc      60

<210> SEQ ID NO 119
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 119
aacctgggca agcatgagaa gttctcggag gtgcttaagc ggctgcgact tcagaagcga      60

<210> SEQ ID NO 120
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 120
agaaatgaag cccggcccac acccgacacc agccctgctg cttcctaact tattgcctgg      60

<210> SEQ ID NO 121
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 121
ctaacttatt gcctgggcag tgcccaccat gcacccctga tgttcgccgc ctggcgagcc      60

<210> SEQ ID NO 122
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 122
gtaagaaact gtctgatatg aatcacaaca tggatgaatg tagtattttc ctgaagtgtg      60

<210> SEQ ID NO 123
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 123
aaagtatgaa ttaggagccg ctctgtttat tggatgggca ggagcctcac tgtgcataat      60

<210> SEQ ID NO 124
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 124
ggaagtcctg gggttttttcc tcttccttct ttgtggtttc tgttttgtaa tttaagaaga      60

<210> SEQ ID NO 125
<211> LENGTH: 60

<212> TYPE: DNA
<213> ORGANISM: Artificial Sequence
<220> FEATURE:
<223> OTHER INFORMATION: Synthetic oligonucleotide

<400> SEQUENCE: 125
aacatcatcc aagacttcta caatccgctg gtggcctccg ggcagaagcg ggagatgggt    60

<210> SEQ ID NO 126
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 126
gatggctcaa ccgtgacttt gggctctgct tgcatcggtg ttggccactg tccccattta    60

<210> SEQ ID NO 127
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 127
tccaggaaga accctaaatt tatggagacc gtggcggaga aagcgctgca ggaataccgc    60

<210> SEQ ID NO 128
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 128
cgctgagagg ttgaccagga aatacaacga gctgctaaag tcctaccagt ggaagatgct    60

<210> SEQ ID NO 129
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 129
gtctacaggc caaaatgcgc acagttgatt ttcggtgtgt tcctgtataa cggcttgaaa    60

<210> SEQ ID NO 130
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 130
gtatttggcc acccagcatt tttgggccga agaaaaaatt caaacctgtt gtccagagac    60

<210> SEQ ID NO 131
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 131
aaaccatgaa ggggccttt tggctgaaatc accacctgcc tttggatgaa ggactccgtt    60

<210> SEQ ID NO 132
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 132
tggatgaaag actccgttgg gaataaatgg ccaaagctta taggactctg tgacaggttg    60

<210> SEQ ID NO 133
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 133
ttaccgctgc aatgacacca tcccagagga ctatgagacc catcagctgc ggcaagccta    60

<210> SEQ ID NO 134
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 134
gctgctgtgg aaggacccgc gaaacgtggg ttggaaggac aagaagtcct atcgttggtt    60

<210> SEQ ID NO 135
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 135
tatctctcca tgttcagttc caaggagtcc cagcggggca tgggctacat gcccaaacgt    60

<210> SEQ ID NO 136
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 136
tttctttgat cttcttttc ttttctcccc ctctttttg ttctaaagaa aagtcatttt    60

<210> SEQ ID NO 137
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 137
ggatcgtttt gttttgtttt taaagaaagg tgagattggc ttggttcttc atgagcacat    60

<210> SEQ ID NO 138
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 138
agagctatat caaatgtgct catgaagaac caagccaatc tcacctttct ttaaaaacaa    60

<210> SEQ ID NO 139
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 139
tcatgagcac atttgatata gctctttttc tgtttttcct tgctcatttc gttttgggga    60

<210> SEQ ID NO 140
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 140
agaccctggt gaaggaggtc gtacagaatt tcgctaagga gtttgtgatc agtgatcgga    60

<210> SEQ ID NO 141
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 141
aacaatgtat gtgaaagtgt aaaatagaat gttactttag aatgactata acattaaaa    60

<210> SEQ ID NO 142
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 142
tcacggccat agcttccaat acaagcacag gggagtttat agttctgatg tctttgacat    60

<210> SEQ ID NO 143
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 143
aagggcttca atcatattgg aggcttcaat catcctttga tttgtactga gtactggttg    60

<210> SEQ ID NO 144
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 144
agaaaggctt accttctgtc atcaagtgat tgtatcatcc tggatcgtca tttccaagga    60
```

<210> SEQ ID NO 145
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 145
tggatcgtca tttccaagga actagccttt cttttcctaa gcgtctgtat gtgttctaaa    60

<210> SEQ ID NO 146
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 146
cccaacttct ctggcaactg gaaaatcatc cgatcggaaa acttcgagga attgctcaaa    60

<210> SEQ ID NO 147
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 147
tgagggcctg agcaggaaag actggccctc tggcttctac actttgtccc tgtagcctat    60

<210> SEQ ID NO 148
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 148
ccctacacca acaaagagga atggctgcaa gagcccagat cacccattcc gggttcactc    60

<210> SEQ ID NO 149
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 149
cgttccagga gaaaaggctc tacttcccag cctttccttg ccctgacat ctggactctt    60

<210> SEQ ID NO 150
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 150
ttcgcccctc ccttgtttta tattttatga agttagtgcg ggctttgctg ctccctggcc    60

<210> SEQ ID NO 151
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 151
ataacaacaa ctttggattt ttatatataa actttgtgat ttaaatttac tgaatttaat    60

<210> SEQ ID NO 152
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 152
ctgtacttgg ataggctggc taacttgtag gaagagagca ctgtatcgta tccttttgct    60

<210> SEQ ID NO 153
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 153
tgtacttgga taggctggct aactcgtagg aagagagcac tgtatggtat cctttttgctt   60

<210> SEQ ID NO 154
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 154
cttatccagg cagctaaaaa cctgatgaat gctgttgtcc tcacggtgaa agcatcctat    60

<210> SEQ ID NO 155
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 155
ataggtgtag cttggagtgc tggtatctaa tataccattg tattcactaa ctaactcaaa    60

<210> SEQ ID NO 156
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 156
gtgaaaaatc tggaagtgta atggtagaac ataaaacttg tattgcttct gtttcagtgc    60

<210> SEQ ID NO 157
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 157
gacttcatca tgctgcagaa caacgagcac agaattgcgc agtacctggc cacttatggc    60

<210> SEQ ID NO 158

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 158
tgaccatcaa catgaagccc cttcagctat accggaaagg tgtgatcaag gccacaccca    60

<210> SEQ ID NO 159
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 159
tagagaccct gtggcgcatc agtttctggg attttgtgga cgtctccgtg catgaactgc    60

<210> SEQ ID NO 160
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 160
ggcggggccg gggggactct ggtatctaat tctttaatga ttcctataaa tctaatgaca    60

<210> SEQ ID NO 161
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 161
aaatttgctg tctaagatta atagcattca aagatcccca gacttcatag aatactcagg    60

<210> SEQ ID NO 162
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 162
caagaggcaa aggaatccat gtagtagata tcctctgctt aaaaactcac tacggaggag    60

<210> SEQ ID NO 163
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 163
cgtacatgtc agaaaccatt agcattgcat gcaggtttca tattctttct aagatggaaa    60

<210> SEQ ID NO 164
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 164
```

```
gtggtacaac gcctggaacg agaagcgcag ggtctacgaa gaatagggtg aaaaacctca    60
```

<210> SEQ ID NO 165
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 165

```
ccctcatttt ttggatagtc accagaccgc aatggaaacg tcctaaggag ccaaattcta    60
```

<210> SEQ ID NO 166
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 166

```
ttagataact ccagcagaaa actgtaactg ctatgtcttc aggaaaatgt agaagaaaga    60
```

<210> SEQ ID NO 167
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 167

```
cttcctgtgc tgcttgtgtc aaatggaacc tgccctctaa agcactttct ttcctttact    60
```

<210> SEQ ID NO 168
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 168

```
cacgtgttct gaaaccactg gtgtctgctc agatgtgttg ggacaaaatg aaagtgactt    60
```

<210> SEQ ID NO 169
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 169

```
atgtggctcc ctcctgctgt cctacagtca caacatggag tttgtctttt tctctgacag    60
```

<210> SEQ ID NO 170
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 170

```
aggatttcta ctttggtctt caagaaagct gtgccccaga acaccagaga tttcaactta    60
```

<210> SEQ ID NO 171
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 171
ttcaagagat ggaaccctaa gtggagaatg agttattcta aggatttcta ctttggtctt    60

<210> SEQ ID NO 172
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 172
agtacacctt ggagtttttt cgaaatatgg gttgggtttt tgggctcttg gttgatttaa    60

<210> SEQ ID NO 173
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 173
gtttatgcta aaataacac caaaatgtgg tgaactctta aggactttc ccttcaagtg      60

<210> SEQ ID NO 174
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 174
ttcactgagg atgataagcc attattaaga agcgttgcta atgttataca gcaggctggg    60

<210> SEQ ID NO 175
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 175 acttttata agcattcttt taataaagga aaattgtttt tgaagtatac ctcctttggg     60

<210> SEQ ID NO 176
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 176
gcacctgtta cagagggaag gccaagtgct gcaagtgagc tgagagtgac cagaagaaat    60

<210> SEQ ID NO 177
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 177
gggggtagtt agggagagac tacatgaaat ggtgtgcccc tatttctttt ctgatcctaa    60
```

<210> SEQ ID NO 178
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 178
agcaataaag tcatccactc ctgcatctgg ttggtcttta ttgagcacct actatatgca    60

<210> SEQ ID NO 179
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 179
ctctgcaccc ccagcctatc ccagaggcct tgcaggtgac cagcagtgtc attgtattta    60

<210> SEQ ID NO 180
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 180
tgtgtagtgt atgttataat acaggctaag ctgccacaat aaaagagctt aaatactgtg    60

<210> SEQ ID NO 181
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 181
agatggggcc aacaaaccgc ctggacttct ggagcccacg tccactctgg tccgtgtgaa    60

<210> SEQ ID NO 182
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 182
aggcaggaaa acagccagaa gccaccttga cactttgaa catttccagt tctgtagagt    60

<210> SEQ ID NO 183
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 183
aataacacct tccaaaaacc tggagtgtaa gagctttgtt tctttatgga actcccctgt    60

<210> SEQ ID NO 184
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 184
atccatttac tcagctggag aggagacatc aagaacatgc cagacacatt tcttttggtg    60

<210> SEQ ID NO 185
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 185
agtcatgagc agagctgaaa attttaaaca agttgagtac ctccttattc atggaacagc    60

<210> SEQ ID NO 186
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 186
gtgccagtta tggctatagg tgctacaaaa acacagcaag ggtgatggga aagcattgta    60

<210> SEQ ID NO 187
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 187
aaatcatttc cgcatcagct gctgaaacaa caaataggaa ttgtttttat ggaagctttg    60

<210> SEQ ID NO 188
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 188
agtctaacac cacaactaat ttcacccaag gttttaagca cgttctttca tcagaccctg    60

<210> SEQ ID NO 189
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 189
aaagcaaagg agtgaacttc taatgctgta atttcagact cacatggttg cgcacatgga    60

<210> SEQ ID NO 190
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 190
gatgaacagg tcaactgctt caacatcaat tatctgagga acgtggctct agtgtctgga    60

```
<210> SEQ ID NO 191
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 191
tggagggtca aatgggggga accccaccct accccacccc tttgaacact cattacagta    60

<210> SEQ ID NO 192
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 192
gaacagaagg aaggaatgcc agctccattt ggggaccaga gccatccaga acctgagtcc    60

<210> SEQ ID NO 193
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 193
cattgcgcaa acactcagaa agtactgcca aaagcctaat aaaaaatcta aagtttgctc    60

<210> SEQ ID NO 194
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 194
cattgcgcaa acactcagaa agtactgcca aaagcctaat aaaaaatcta aagtttgctc    60

<210> SEQ ID NO 195
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 195
cattgcgcaa acactcagaa agtactgcca aaagcctaat aaaaaatcta aagtttgctc    60

<210> SEQ ID NO 196
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 196
aagttattac aggtataaaa gtgatgacct atcatgagga aatgaaagtg gctgatttgc    60

<210> SEQ ID NO 197
<211> LENGTH: 60
<212> TYPE: DNA
<213> ORGANISM: Artificial Sequence
<220> FEATURE:
<223> OTHER INFORMATION: Synthetic oligonucleotide
```

<400> SEQUENCE: 197
cagaaagaaa gagcaataat aattaattca catgccatgt ggattctatt tataaatcac    60

<210> SEQ ID NO 198
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 198
gcttcactga attcctgcat taacccaatt gctctgtatt tggtgagcaa aagattcaaa    60

<210> SEQ ID NO 199
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 199
gtaaaccaaa acccaacaat gtggccagaa agaaagagca ataataatta attcacacac    60

<210> SEQ ID NO 200
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 200
tgtgacaagt ggacactatt tatgttaaat atacaatcat caaggaagta tgaagttatt    60

<210> SEQ ID NO 201
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 201
aggcagccat cataaccatt gaatagcatg caagggtaag aatgagtttt taactgcttt    60

<210> SEQ ID NO 202
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 202
ggaggcagcc atcataacca ttgaatagca tgcaagggta agaatgagtt tttaactgct    60

<210> SEQ ID NO 203
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 203
ggaaccactc ccaccacagg cacaagctgt cacctagcag cctcaaaacg ggtcagtatt    60

<210> SEQ ID NO 204
<211> LENGTH: 60

<212> TYPE: DNA
<213> ORGANISM: Artificial Sequence
<220> FEATURE:
<223> OTHER INFORMATION: Synthetic oligonucleotide

<400> SEQUENCE: 204
taaagggcag ggcccacgtg tatagtatct gtatataagt tgctgtgtgt ctgtcctgat    60

<210> SEQ ID NO 205
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 205
atggagaaag aagtggagac agtcctttcc caccattcct gcctttaagc caaagaaaca    60

<210> SEQ ID NO 206
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 206
agttttccgg gccaagaatt tttatccatg aagactttcc tactttctc ggtgttctta    60

<210> SEQ ID NO 207
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 207
tgtatggatt agcatcagtg aagaacgtta ctcttttgtc aaggtatttg gatttgctca    60

<210> SEQ ID NO 208
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 208
ttgtgaatct attgtttctc ctctgaagca tttggtggcc taatttacaa gcacgatgga    60

<210> SEQ ID NO 209
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 209
agattacaca accttcacga cagttggtga ttggctggat gccatcaaga tggggcggta    60

<210> SEQ ID NO 210
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 210
aactggagga ggggactcca ggaatgggga aatgtgacac caccatcctg aagccagctt    60

<210> SEQ ID NO 211
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 211
ccaaacgagc tgttcataac agcgattttg cctaacatta tatcataagc gtgttccaat    60

<210> SEQ ID NO 212
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 212
ttgctccctg attaaaatga gatatggcta tttggaagac actgcatttt agccagtgta    60

<210> SEQ ID NO 213
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 213
taaataggga taagagaaac tcttactatg cagattacgt ttttgaatgg tgaacaggct    60

<210> SEQ ID NO 214
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 214
aacacttgga ggtgtgcctt gtacgtcact caacaaacac tcagcagctg ctaaaagaaa    60

<210> SEQ ID NO 215
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 215
gagttggtgt tcataatttc agttctagtt gattgcgaga attttcaaat aaggaagagg    60

<210> SEQ ID NO 216
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 216
gtgaatagca atatcccaac taaccttcgt gtgcttcgtt caatcctgga aaacctgaga    60

<210> SEQ ID NO 217
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 217
tgagcaaagg agcttaatgc taaggtcaaa aggagagtg aaaggttgag aacaattgtc    60

<210> SEQ ID NO 218
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 218
tgtgatcatc agcaataaag atataataac tctgttttct tagcctgtat agaggagagg    60

<210> SEQ ID NO 219
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 219
actgaagact ttgaacactt gcttttgtg attgcttatg tcattagtgc ctcatgactg    60

<210> SEQ ID NO 220
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 220
actcagctct cacagggta atcatctcaa gtggtatttg tagccaagtg ggagctattt    60

<210> SEQ ID NO 221
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 221
tccctcattc atcttgcaag caaatcccat ttcttgaaaa gccttggaga actcggtttg    60

<210> SEQ ID NO 222
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 222
tgggactgga agtgacctgt acaagtgatg cagaaaggag ggtttcaaag aaaaaggatt    60

<210> SEQ ID NO 223
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 223
tattggaaga cttgggttga tctcttagaa gccatgggac ctcctccctc attcatcttg    60

<210> SEQ ID NO 224
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 224
tgctgtcact ccgggcacct cgaacctcgt cttcacctat cctagcgtcc tggagcagga    60

<210> SEQ ID NO 225
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 225
tgactatgag accgttcgca atgggggcct gatcttcgct ggactggcct tcatcgtggg    60

<210> SEQ ID NO 226
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 226
ctttagacct ttgtccccgt cactgccagc gcttgggctg aaggaagctc cagactcaat    60

<210> SEQ ID NO 227
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 227
ccaacactgt gtgaattatc taaatgcgtc taccattttg cactagggag gaaggataaa    60

<210> SEQ ID NO 228
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 228
gacgcgtcca ctactgtgtc aattatctaa atacgtctac cattttgcgc tagggaggaa    60

<210> SEQ ID NO 229
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 229
gatctcttac ctttggaaaa tagggggttag gcatgaaggt ggttgtgatt aagaagatgg    60

<210> SEQ ID NO 230
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 230
ggattggctt tgatagagga atggggatga tgtaagttta cagtattcct ggggtttaat    60

<210> SEQ ID NO 231
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 231
tgtgtgtcag ttctgtcagc tgcaagttct tgtgtaatga agtcaatgct gtcaggccaa    60

<210> SEQ ID NO 232
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 232
cctgccttaa gtcaacttat ttgttttgc cgggaaagtc gctacatgga tcaatgggtt    60

<210> SEQ ID NO 233
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 233
ttgttccact cttacgagac tgcaccaact cggatcatca gaaatggttc ttcaaggagc    60

<210> SEQ ID NO 234
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 234
gatttgtgaa tgatcccaga ccaaccctga gattttgtca acctgattaa gtcaatatga    60

<210> SEQ ID NO 235
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 235
gagaatcaga agttcatctt gcaggaggat ggatctttat ttcacgaaca gtccaagaaa    60

<210> SEQ ID NO 236
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 236
tccctataac tcaaaataac ttgtttgtaa aagaaaattt gtttacttac ccattagtaa    60

<210> SEQ ID NO 237

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 237
acttttctag gatgaagaca gcttattttt aagttgtatg gtcttagttg gtttagggtc      60

<210> SEQ ID NO 238
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 238
ggtatttgaa aaacgttttt cctaatttac atgttccaga ggatagacca ggctggcatg      60

<210> SEQ ID NO 239
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 239
aaagctgggg ttcatttttgg tatatcacac tgaaactggg tacccagagt gctgctgttt     60

<210> SEQ ID NO 240
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 240
cttggggaca gatagagggg atggttgggg atacttccca aaacttttc aagtcaactt       60

<210> SEQ ID NO 241
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 241
ggattaaggg tccaaaaatg ctgatctaag gggttgccat ggtgttgaac aatgcaactt      60

<210> SEQ ID NO 242
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 242
atggatggat ggacttcggc cgccgcagtg ctgaggatga gaactaacaa tcctagaacc      60

<210> SEQ ID NO 243
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 243
```
agcctatgga tggatggact tcggccgccg cagtgctgag gatgagaact aacaatccta        60

<210> SEQ ID NO 244
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 244
gctgaagtgt ggtgaatatg atgaaaatct gatgagacca aacaagccat ggggcacagt        60

<210> SEQ ID NO 245
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 245
atacaggcca aagaggtgct gaaaaaatat ttggagtcca aggaggatgt ggctgatgca        60

<210> SEQ ID NO 246
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 246
tattggggtg accttcttgg ggactcgggg gctggtctga tggaactgtg tatttattta        60

<210> SEQ ID NO 247
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 247
ttggggtgac cttcctggga actgggggc tggtctgatg gaactgtgta tttatttaaa        60

<210> SEQ ID NO 248
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 248
aagggataaa cctaaatatt tacttgttat cattagagag ggaacatcaa atgctgggac        60

<210> SEQ ID NO 249
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 249
cagctcaagt accctaattt agttcttttg gactaataca attcaggaaa gaaaaaccc        60

<210> SEQ ID NO 250
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 250
gtgtgtagga cggggaggtc acgatggcgc gacgtctgca gaaatttcat gaggaggtat      60

<210> SEQ ID NO 251
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 251
tgtggaattc atccatccaa ttaattccag cttataatat ttctggtcca catttgatgc      60

<210> SEQ ID NO 252
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 252
ccatagtaat aatacacatt tctgtgagtg ctgacttgtc tttgcaatat ttcttctctg      60

<210> SEQ ID NO 253
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 253
acccctttta gttaagtctt tcactaaggt tctcttgcat atatttcaag tgaatgttgg      60

<210> SEQ ID NO 254
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 254
agggaactgt cctacactgc tattgttgct acatgtatcg agccttgatt gctcctagtt      60

<210> SEQ ID NO 255
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 255
atgagaccat cctgaaagag cagaagggtc agagcatgtt cgtggagaac aaggcctttt      60

<210> SEQ ID NO 256
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 256
cctgaaagag cagaagggtc agagcatgtt cgtggagaac aaggcctttt ccatggatga      60
```

<210> SEQ ID NO 257
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 257
tccagccaaa tagtgttctc ggggtggtgg ctgggcagcg cctatgtttc tctggagatt    60

<210> SEQ ID NO 258
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 258
gcaggaacag gtgtccatga ccctgattac ctggatctca caggttctgg gaatgcaata    60

<210> SEQ ID NO 259
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 259
gggcctgctg tggctattcc aacatctctg gtcagggcct ggaagtacct taggacacat    60

<210> SEQ ID NO 260
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 260
aggcctggat cttgctcctc tgtgaggaac aagggtgcct aataaaaaca tttctgcttt    60

<210> SEQ ID NO 261
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 261
tgggtgtggg tgcatgtggg tgtttacaca catgcctaca ggtatgcgtg attgtgtgtg    60

<210> SEQ ID NO 262
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 262
cactcaaggc cccagcctgg cacaaatgga tgcatacagt tctgtgtact gccaggcatg    60

<210> SEQ ID NO 263
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 263
tcgttgggaa attgatgacc ggaaactaga aagcccctat aatgtggaat atgcatatgt    60

<210> SEQ ID NO 264
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 264
ctgacgttac taagcattgc agcacaatgt agaaattggc ttgggatgga taggtatagg    60

<210> SEQ ID NO 265
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 265
gcaaacacga gcacactctc ttcgaaccca attgtgggtg tagcaatgaa agcaatatga    60

<210> SEQ ID NO 266
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 266
aagtccactg ttagtctctc cgttagcacc aggacacac ttgttctgag ttttgttcat    60

<210> SEQ ID NO 267
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 267
ctccttctgg gggttatcgt atgtacaaag tttaccttat aatggctcaa attgtattta    60

<210> SEQ ID NO 268
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 268
gaatgaatat ggtttgtgct ggaagcctcc gaggtggaaa aaactcgtgc aatggagatt    60

<210> SEQ ID NO 269
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 269
aaattaggcg ccttgtttga gctgcatttc acacttcttt agagctagct gacctttggc    60

<210> SEQ ID NO 270
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 270
aacccaagga atgatggaat caacacaaca tagtatgttt gctttcctta cccaattgta    60

<210> SEQ ID NO 271
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 271
ttctgcacaa gaaatccacc aaaatcccgg agtctgagga cctttaatgg gctttgtcat    60

<210> SEQ ID NO 272
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 272
agatcaatcc attgtatcat tcagttcttc taaagcctac gttggttagg ctgatggcag    60

<210> SEQ ID NO 273
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 273
ccaggtattt tcagattgta ggagttttct ttcttaacaa tttcaacagg ccactcactc    60

<210> SEQ ID NO 274
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 274
gcaacagata atcctatggt ctttgccaat aggggagaga caatttctgg aggaaacttc    60

<210> SEQ ID NO 275
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 275
ttggggtcgg tatctagtgc tatccattca tctgtggtcg ttccctcttt gaagatgttt    60

<210> SEQ ID NO 276
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 276
tctgaggact ccttgcattt ggaatcatcc ggtttattta tgtgcaattt ccttcccctc    60

<210> SEQ ID NO 277
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 277
ataggtttgt actgtgccta atttactttg taaaccagaa tgattccgtt tttgcctcac    60

<210> SEQ ID NO 278
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 278
aaacgacctc cactgaactg ggtttgacct ctgttgtact gatgtgtcgt gactaaataa    60

<210> SEQ ID NO 279
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 279
gggctataaa atatcatttt tcaggtttat tcttttagca ggtgtagtta aacgacctcc    60

<210> SEQ ID NO 280
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 280
taaaagataa gagacacaac atgtattatg cacttcattt ctctactgtg tggagaaagc    60

<210> SEQ ID NO 281
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 281
aaaggagagg gattatagag aaaaggcgtc gggatcggat aaataacagt ttatctgagt    60

<210> SEQ ID NO 282
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 282
aagctctttg tcaagttagt gattgcattt gatcccaaaa caagatgaat gtatgcaatg    60

<210> SEQ ID NO 283
<211> LENGTH: 60

```
<212> TYPE: DNA
<213> ORGANISM: Artificial Sequence
<220> FEATURE:
<223> OTHER INFORMATION: Synthetic oligonucleotide

<400> SEQUENCE: 283
tactcggggc aaagtactag ctctgtgatt agattgaatt ctccaacaac aacatctcag    60

<210> SEQ ID NO 284
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 284
ttccagtccc aaatcattta cttttctgtg gtccagccct actcctataa gtcatgatct    60

<210> SEQ ID NO 285
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 285
ggtagggagg caggaagagg gaaacattgt gtcttgttta ggatccttat tgtgtgtatc    60

<210> SEQ ID NO 286
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 286
ccaaatcatt tacttttctg tggtccagcc ctactcctat aagtcatgat ctccaaagct    60

<210> SEQ ID NO 287
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 287
ccaaatcatt tacttttctg tggtccagcc ctactcctat aagtcatgat ctccaaagct    60

<210> SEQ ID NO 288
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 288
tgtcttccaa ctgcagtctc cacagtcttc agaagacaaa tgctcaggta gtcactgttt    60

<210> SEQ ID NO 289
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 289
```
ggtctctcgg aagccaccgt gtggttcttt cacaggcacg tttattttgc tgaaataaaa    60

<210> SEQ ID NO 290
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 290
agacaaagta gtgaacatca atgaacatct gatagagata aactgtaatc aggcataagc    60

<210> SEQ ID NO 291
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 291
catcattatc aatatgtcat ctttagcagg actcatgccc gttgcacagc agccggttta    60

<210> SEQ ID NO 292
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 292
cctctgctca ctttaagaac tttaactgac tccaaaaatc tcaggaatta aactgttaac    60

<210> SEQ ID NO 293
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 293
agtggatgaa aacttcgatc ctttacctga ttattggcta tctcttctgt tcaagaaatt    60

<210> SEQ ID NO 294
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 294
catcaagggg gtcttgtttt gctagagagt ttggggtttg gtttgtggat ttcattgtga    60

<210> SEQ ID NO 295
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 295
tgcagatagt gcctctgcaa actaaggagt gactaggtgg gttggggacc ccctcaggat    60

<210> SEQ ID NO 296
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 296
aaagccaccg gaggaaagga aaaaacatcg gccaacctag aaacgttttc attcgtcatt    60

<210> SEQ ID NO 297
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 297
gttctggtgt catagatgtc ccattttgtg aggtagagct gtgcattaaa cttgcacatg    60

<210> SEQ ID NO 298
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 298
gcacagggaa gttctggtgt catagatatc ccgttttgtg aggtagagct gtgcattaaa    60

<210> SEQ ID NO 299
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 299
gcacagggaa gttctggtgt catagatatc ccgttttgtg aggtagagct gtgcattaaa    60

<210> SEQ ID NO 300
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 300
cgactgtcga gattgcccag tatgttctgt gaacacaaat aaacttgatt tactgtctgc    60

<210> SEQ ID NO 301
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 301
tgtgagatgt tcccctgct gtaaatgcag gtctcttggt atttattgag ctttgtggga    60

<210> SEQ ID NO 302
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 302
cgactgtcga gattgcccag tatgttctgt gaacacaaat aaacttgatt tactgtctgc    60
```

<210> SEQ ID NO 303
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 303
gtacgtaata tttattttaa cttatgcaag ggtgtgagat gttcccctg ctgtaaatgc    60

<210> SEQ ID NO 304
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 304
gccacaacaa ccctcttaaa actaattggc ttttagaaa caccccacaa aagctcagaa    60

<210> SEQ ID NO 305
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 305
tgcttccgga caacttcccc agataccccg tgggcaagtt cttccaatat gacacctgga    60

<210> SEQ ID NO 306
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 306
ctcaactcag ctcctttaac gctaatattt ccggcaaaat cccatgcttg ggttttgtct    60

<210> SEQ ID NO 307
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 307
catgaaacac ttctcatcat attgtatgta agtaattgca tttctgctct tccaaagctc    60

<210> SEQ ID NO 308
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 308
tttctgctct tccaaagctc ctgcgtctgt ttttaaagag catggaaaaa tactgcctag    60

<210> SEQ ID NO 309
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 309
aatcaaagct acctgtggtg atgttgccac cggttaaaat gtacactgga tatgttgtta    60

<210> SEQ ID NO 310
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 310
ctgtgtggaa ccactgacta ctggctctca ttgacttcct tactaagcat agcaaacaga    60

<210> SEQ ID NO 311
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 311
ttgaggttgt ctgagtcttg ggtctatgcc ttgaaaaaag ctgaattatt ggacagtctc    60

<210> SEQ ID NO 312
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 312
ccacaaagtg gacgcctgct gtatcttccc aacagtggct tcacagaccc acaagagaag    60

<210> SEQ ID NO 313
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 313
ctcccggatg ccttggagat agaggcctgc caggtgtact ttacttacga cccctactca    60

<210> SEQ ID NO 314
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 314
tccccccaga atataaatct caggtaataa ggctttagaa ctgctgataa agcggatcgt    60

<210> SEQ ID NO 315
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 315
tagctgtttc tctctttaat ctcacgtagc cttttcagg ttagtacgtg ttcttctgtc     60

<210> SEQ ID NO 316

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 316
atctgcaaat cgtgactaag tacatcctga ttcctgcaag ccagcagcca aaggagaata    60

<210> SEQ ID NO 317
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 317
acccgcgagt tcgggctcct gctgctcttc ctctgcgtgg ccatcgccct cttcgcgccc    60

<210> SEQ ID NO 318
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 318
ccctatgtgt gtttccctca ataaggagat gccttgttct tttcaccatg caataacat    60

<210> SEQ ID NO 319
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 319
cctgtcggtg ctcttcgtga ccgtcaccgc cgtcaacctc tccgtcagca ccttgcccag    60

<210> SEQ ID NO 320
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 320
ccagccccta tgtgtgtttc cctcaataag gagatgcctt gttcttttca ccatgcaaat    60

<210> SEQ ID NO 321
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 321
ccgccgatgc acccgcgagt tcgggctcct gctgctcttc ctctgcgtgg ccatcgccct    60

<210> SEQ ID NO 322
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 322
```
aagttgaaca atcctagcca ttgacaatcg tgatagttat tattttccca tttgctgtct    60

<210> SEQ ID NO 323
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 323
tcgttttgtg ttttccccaa aacttgaact tgcaggcaag ccttggttgg gtatttgatt    60

<210> SEQ ID NO 324
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 324
cctgcgccat tgcctgctgc ctgtgctcag ccgcccacgt gcctgggtag cggtccactg    60

<210> SEQ ID NO 325
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 325
gcttgctgaa gcgtcaggtg accgagttca gctcccataa ggtggcggca cctaaggagg    60

<210> SEQ ID NO 326
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 326
cttttgtaac tcaagtcttg aaatgttctg tagtgttaag caaagtctcc tcttgcttga    60

<210> SEQ ID NO 327
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 327
atgatgaaca gagttatgat tcctatgata acagctatag cacccccagcc caaagtggtg    60

<210> SEQ ID NO 328
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 328
aaacacacag ctgctgaatg ttcaacctgt gaaactgaga tgtttctaga atgaaacagt    60

<210> SEQ ID NO 329
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 329
aggataccaa atggaaacac atgatgatgc ctctgggtct gtatgagacc gtgatgaagt      60

<210> SEQ ID NO 330
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 330
ctcaaagttt tcttaaggga aaacactaca aaaagtcaca aggataccaa atggaaacac      60

<210> SEQ ID NO 331
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 331
cacatagtcc tttgtgaact tgtttgtgaa ggaagttcac ttttttgtgta catacgtgta     60

<210> SEQ ID NO 332
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 332
ttgcaaggca ttagaaaaaa tttcacaatt acaggggact gaaaatgtga tttcaaccag      60

<210> SEQ ID NO 333
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 333
acactccaag acctgtgcct tttagagaag ctcacaatga tttaaggact gtttgaaact      60

<210> SEQ ID NO 334
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 334
aacacactgg agaggtctaa agtggaagaa actacagagc acttggttac aaagagcaga      60

<210> SEQ ID NO 335
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 335
tcaagccttg accacttgtg atgacatctt aatcaaacag gaccagactc tggctgaact      60
```

<210> SEQ ID NO 336
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 336
gcttgggaga tgctttcagg ttgcagccag aagggtttt ttaaatgact tctctggatt    60

<210> SEQ ID NO 337
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 337
ggttgaaata ggagatgacc tctaactgat agaacgttac tttgtgtcgt gatgaaaact    60

<210> SEQ ID NO 338
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 338
attgttggga tcctgggaat tatctgtctt atcttaatgg cctctgtggt aacgatagtt    60

<210> SEQ ID NO 339
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 339
agtggaatat taagtaaaag ttgggcacta atctggatta acattcgagg aaatcagttg    60

<210> SEQ ID NO 340
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 340
ataggacaga tcccatctcc tccacccaat acattattag actgaactgt gacctgaaat    60

<210> SEQ ID NO 341
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 341
tcatgcgatt atgccatcga cctttatccc tctctataca atggtcactt tttccagaat    60

<210> SEQ ID NO 342
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 342
aaagtgggaa ataacttgca acgtctgtta gagatggttg ctacacatgt tgggtctgta    60

<210> SEQ ID NO 343
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 343
agaatgaaga taaaatgttg atcatgtata tatatccata gtgaataaaa ttgtctcagt    60

<210> SEQ ID NO 344
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 344
agtgtattcg acaactctgt gagtttctta cagaaaatgg ttatgcacat aatgtgtcca    60

<210> SEQ ID NO 345
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 345
gaagatgaaa ttaaccgccg cacagctgct gagaatgagt ttgtggtgct gaagaaggat    60

<210> SEQ ID NO 346
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 346
gaagatgaaa ttaaccaccg cacagctgct gagaatgagt ttgtggtgct gaagaaggat    60

<210> SEQ ID NO 347
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 347
gcctttagtt ctccactggg gaggaatcct ggaccaagca caaaaactta acaaaagtga    60

<210> SEQ ID NO 348
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 348
atggccaggt tgcctacgag tggggtccac tgatgaaaag aggttttttg tacttacata    60

```
<210> SEQ ID NO 349
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 349
ccaggttgcc taggagtggg gtccactgat gaaaagaggt gttttgtact tacataagaa    60

<210> SEQ ID NO 350
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 350
catttccctg cagatggtac agatgttcct gccttagagt catctctagt tccccacctc    60

<210> SEQ ID NO 351
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 351
gtcttccaga agaagaagct gggctgtcaa ctcctgggga agtataagca gatcatcgcc    60

<210> SEQ ID NO 352
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 352
tctggcaccc ggggaggtag catttccctg cagatggtac agatgttcct gccttagagt    60

<210> SEQ ID NO 353
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 353
aggagcaggc tgggatccca actatcgctt gttgcctctt ttcaagtgga atttgaattt    60

<210> SEQ ID NO 354
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 354
aggagcaggc tgggatccca actatcgctt gttgcctctt tttcaagtgg aatttgaatt    60

<210> SEQ ID NO 355
<211> LENGTH: 60
<212> TYPE: DNA
<213> ORGANISM: Artificial Sequence
<220> FEATURE:
<223> OTHER INFORMATION: Synthetic oligonucleotide
```

<400> SEQUENCE: 355
acacactggc tcctagacct aaagggtatg agctggagct aaggccagct agagcttcca    60

<210> SEQ ID NO 356
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 356
acttgaaggt ttgatgccaa agcagacatt ttcctcacac ccacctgctg ctgtatgaat    60

<210> SEQ ID NO 357
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 357
ggtgtgatgg acgggcagct tcctgtgtgc tccaagggat gagcctcgtg gggcagaggg    60

<210> SEQ ID NO 358
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 358
ctttcctcgg ttctggcctc cagaccagag taaggggcag gtccctccaa caggtgctca    60

<210> SEQ ID NO 359
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 359
agcactgatt tactctgtaa aaagcaaaat ctctctgtcc taaactaatg gaagcgattc    60

<210> SEQ ID NO 360
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 360
tctggctccc tggatgacac agagacggag cagctgttac aggaagagca gtctgagtgt    60

<210> SEQ ID NO 361
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 361 tttttttctga ataagtctct cataatgagt gcagtgtcag actgtgccta ctctgatggt    60

<210> SEQ ID NO 362
<211> LENGTH: 60

<212> TYPE: DNA
<213> ORGANISM: Artificial Sequence
<220> FEATURE:
<223> OTHER INFORMATION: Synthetic oligonucleotide

<400> SEQUENCE: 362
ttaagggata ttgggaaaag ttttggtgtg tttctgttga cttcttttt gtatgctgtg     60

<210> SEQ ID NO 363
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 363
aggaagctta tagtgggtca acaaggagg tgtttagtgt gttgtttaaa aagaaggctc     60

<210> SEQ ID NO 364
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 364
gcaccactac aatgtccatt ttaatggcct ggaatgcaaa acgcctgaag aatacaaagg     60

<210> SEQ ID NO 365
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 365
ctgctgaaga tcattggatt ttccacatca gtaactgccc tggggtttgt gctgtacaaa     60

<210> SEQ ID NO 366
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 366
ccccagtgct acacgttgga gtatacctat gtgtgtgctt tgccactgaa gtaagatttt     60

<210> SEQ ID NO 367
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 367
ttttctttct tggcctcaag ttcaatatgg agagggattg cttccctgaa tcctctcttc     60

<210> SEQ ID NO 368
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 368
acagcatcaa tagaaagtca tctttgagat aatttaaccc tgcctctcag agggttttct    60

<210> SEQ ID NO 369
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 369
gtctgcttgg atttcctaca gcccccgtgg gcatggacca cctttatttt atacaaaatt    60

<210> SEQ ID NO 370
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 370
ccgcctctac tccatacaca ggccttgcaa acagtgtctc aacgaggtct gcttctacag    60

<210> SEQ ID NO 371
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 371
tgagaggaag gaggatctcc ttcttctcca accattgaca gctaaccctt agacagtatt    60

<210> SEQ ID NO 372
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 372
ttgaccctcc tactccacat tgcaacattt gcatcagaca gcatttcaat tccagtatta    60

<210> SEQ ID NO 373
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 373
agatgactgt ttctcatgcc tttatcttcc ttcatgtaag taaagtggac ctttgtgctc    60

<210> SEQ ID NO 374
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 374
tattcaacct gtcctttcag ggagtttatt ggaggatcaa agaactgaaa gcactagagc    60

<210> SEQ ID NO 375
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 375
ttctcaatct aaatgccttt caggtgggcc gcttccttgg ctacctggtt ccaggggggct    60

<210> SEQ ID NO 376
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 376
aagtggctgg aagagtccct tagtactctt ctagcattta gatctacact ctcgagttaa    60

<210> SEQ ID NO 377
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 377
aacatttgct ctgggggggc agggaataca cagatgcgtt gcaaaggtag gttgaaggga    60

<210> SEQ ID NO 378
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 378
accgccgcgc caaggcaaag agactacaag aggcagagct ggagaagctg aagatggccg    60

<210> SEQ ID NO 379
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 379
agctgctgtg cctgatgtcg ggacagccct gctcccaagt acaaatagag tgaccccgtaa    60

<210> SEQ ID NO 380
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 380
ttgggaactc tagtctcgcc tcgggttgca atggacccca actgctcctg tgccgctggt    60

<210> SEQ ID NO 381
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 381
gcatcggaga agtgcagctg ctgcgcctga tgtcgggaca gccctgctcc caagtacaaa    60

<210> SEQ ID NO 382
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 382
tgtgccaagt gtgcccacgg ctgcatctgc aaagggacgt cggagaagtg cagctgctgt    60

<210> SEQ ID NO 383
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 383
caaccctgac cgtgaccgtt tgctatattc cttttctat gaaataatgt gaatgataat    60

<210> SEQ ID NO 384
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 384
cgctcccaga tgtaaagaac gcgacttcca caaacctgga tttttatgt acaaccctga    60

<210> SEQ ID NO 385
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 385
cacaatgatt ccaacttcaa ctctttccct tggtttacta gagactacag gcttactggc    60

<210> SEQ ID NO 386
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 386
gagcacacgc tagttcagaa agtccaagca ccatcaaact taccatggct tcagtagtaa    60

<210> SEQ ID NO 387
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 387
tggtgtcttt atctgcagta acctcaccct cgccacttta ttccacacca tctgagagta    60

<210> SEQ ID NO 388
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 388
ccaagacctc cttggttgaa acaactgatg gaacgctagt gaccaccata aagatgtcaa    60

<210> SEQ ID NO 389
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 389
cagaatcagc agaaatgatg atcaagacac aaacagatcc tcctgggtct acaccagaga    60

<210> SEQ ID NO 390
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 390
cagggatcca ctcagctatg actcatggat tttcacaatt ggatgtgacc actcttatga    60

<210> SEQ ID NO 391
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 391
tatccctttt tccatgacac taagcaatgc agaaacaagt gccgaaaggg tcagaagcac    60

<210> SEQ ID NO 392
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 392
agcatcaaga gttattttc tgactgtcaa gtttcaacat tcaggtctgt ccccaacagg    60

<210> SEQ ID NO 393
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 393
tgagtcctgg gatcagacac cccttcacgt gtatccccac acaaatgcaa gctcaccaag    60

<210> SEQ ID NO 394
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 394
tgaggaagtg gacgagatgt accgggaggc acccattgat aagaaaggca acttcaacta    60

<210> SEQ ID NO 395

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 395
tgtgctcagg agttgcgggc agcatggaca tctgtcccag aggaggcaga atctccaata    60

<210> SEQ ID NO 396
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 396
ttttcagcca ggaagagctc tctggaaatt ctgagttgat acaaaagtac agaaatatca    60

<210> SEQ ID NO 397
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 397
cgtttggctg cactaacttt ggtagctcag tgtgcatcta gagtgggact ggggagggag    60

<210> SEQ ID NO 398
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 398
gttttgagcg ttgtattcca aaggcctcat ctggagcctc gggaaagtct ggtcccacat    60

<210> SEQ ID NO 399
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 399
aggaagctga gcagatccct gtgatgcctg tgacctcaat taaagcaatt cctttgacct    60

<210> SEQ ID NO 400
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 400
ctgctgtgaa agaggctggc tacacaatcg aatggtttga ggtgatctcg caaagttatt    60

<210> SEQ ID NO 401
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 401
```
ctactagctc tttgagataa tacattccga ggggctcagt tctgccttat ctaaatcacc    60

<210> SEQ ID NO 402
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 402
agcagctttt gactgtttcc agagtgctta taatatacat aactccctgg aaattactga    60

<210> SEQ ID NO 403
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 403
ctaaatgttg cgtgggtggc atgagttgaa gaaggcaaag gcttgtaaat ttacccaatg    60

<210> SEQ ID NO 404
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 404
aagttttctg ctgtaaagaa agctgtaata tatagtaaaa ctaaatgttg cgtgggtggc    60

<210> SEQ ID NO 405
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 405
tataacaaaa tgttttattt tcattttagc aaaaattgtc ttataatact agctaacggc    60

<210> SEQ ID NO 406
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 406
gctaacggca aagacgtttt tatagggaaa ctatttatat gtaacatcct gatttacagc    60

<210> SEQ ID NO 407
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 407
catctgcgtg gctctgctgg tcgtgggcat cgtctgtgtg gtggcctact gcaagaccaa    60

<210> SEQ ID NO 408
<211> LENGTH: 60
<212> TYPE: DNA

<213> ORGANISM: Artificial Sequence
<220> FEATURE:
<223> OTHER INFORMATION: Synthetic oligonucleotide

<400> SEQUENCE: 408
ggacagagat gtttggagaa actgcctttg cgattgtaca tgccagatcc taagcaaagt    60

<210> SEQ ID NO 409
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 409
ctagctaacg gcaaaggcgt ttttataggg aaactattta tatgtaacat cctgatttac    60

<210> SEQ ID NO 410
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 410
ctgcaatcta gtgacaaagt cgaaagttta acaggctttt ctcatgaaga actagacgac    60

<210> SEQ ID NO 411
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 411
tagttcccct gattctgacc ttgagtttgt agccaatact aaggcaaggg tcaaagagct    60

<210> SEQ ID NO 412
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 412
ttttctcacg aagaaccaga tgactcttgg taaccatgtt tgctgcccag cttctaactt    60

<210> SEQ ID NO 413
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 413
aagggccctc caagccttaa tggcacccct aagcctccat gcccaggcca aaagatgctt    60

<210> SEQ ID NO 414
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 414
gggctaactt aaaagagttt tttcaatgct gcagtgactg aagaagcagt ccactcccat    60

<210> SEQ ID NO 415
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 415
agggctatgc ctgtgtctta ttgagacacc ttggcaaaga gatggctgat tctgggtggt    60

<210> SEQ ID NO 416
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 416
tcaaaggaat tactctcttc ttgttaaatt agctaaatca tgtaaccgca gataggaagg    60

<210> SEQ ID NO 417
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 417
tttttccttt gatgttcaag tcctagtcta taggattggc agtttaaatg ctttactccc    60

<210> SEQ ID NO 418
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 418
ttagatatct gcaggggtgt ctaaaagtgt gttcattttg cagcaatgtt taggtgcata    60

<210> SEQ ID NO 419
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 419
ttgaaggcaa agatcatcaa tatctgcatc tggctgctgt cgtcatctgt tggcatctct    60

<210> SEQ ID NO 420
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 420
cagttcttaa acgtgtataa ctattgtcag acaatttata ggtgtttcat ctagtcctgg    60

<210> SEQ ID NO 421
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 421
gaaaatcaca tccaaaaacg gtataaccca gcttccttaa ggcaattttc ttctctgaaa    60

<210> SEQ ID NO 422
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 422
tagtcgtgga gatgtcttcg tacagttctt caggaagaga ggagttcaat gatctgggtt    60

<210> SEQ ID NO 423
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 423
tacggtggcg aacgaggcca cgctgctcga tactgactac gacaatttcc tgtttctctg    60

<210> SEQ ID NO 424
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 424
caaggccccc tctgtccttt tcagaacaca tggacttgga ggcagatttg aaataaactt    60

<210> SEQ ID NO 425
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 425
gccatgttgc cacatgagca agcttgggtg ctcccaaggt tcaaatactt tttattagac    60

<210> SEQ ID NO 426
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 426
tttccctcca agctcctatt ttactgtgtc agctggaagg aaacctttcc ctcttgggac    60

<210> SEQ ID NO 427
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 427
ttactgtgtc agctggaagg aaacctttcc ctcttgggac ctctttaccc tctgtgacct    60

<210> SEQ ID NO 428
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 428
agctctggaa acagatgtct agtgatcatc tcagctgaag tgtggcttgc gtaaataact    60

<210> SEQ ID NO 429
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 429
attggctata agcacttgga attgtactgg gttttctgta aagttttaga aactagctac    60

<210> SEQ ID NO 430
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 430
cttcagggaa gatggctatc agatgaatgc acaaatgctg tggtgaactt cttatccaga    60

<210> SEQ ID NO 431
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 431
ttcattgtct ggataactat acaacctgaa aactgtcatt tcaggttctg tgctcttttt    60

<210> SEQ ID NO 432
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 432
tttgctagcc aaaaggtatg ggggcttcat gaaaaggtat ggaggcttca tgaagaaaat    60

<210> SEQ ID NO 433
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 433
catttcaggt tctgtgctct ttttggagtc cttaagctca gtattggtct gttgcagcta    60

<210> SEQ ID NO 434
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 434
gagaaaagca aagctctttc ttattttcct cataatcagc taccctggag gggagggaga    60

<210> SEQ ID NO 435
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 435
ttacctgaac cagtgaactt acaagcaagt gtgactgttt cctgtgacct gaagatagcc    60

<210> SEQ ID NO 436
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 436
ctgctgcctg tctccctgac ccatgatctg gcaagttagg cacagtcaga catggacagt    60

<210> SEQ ID NO 437
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 437
ggagagtggt cactggggaa aaggacctgg ccatcacctt ccagtacctg ctgcctgtct    60

<210> SEQ ID NO 438
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 438
ctatgaggca ccacgtaaga cctcctgccc ttagctctct tgctcaccac ccaagaacct    60

<210> SEQ ID NO 439
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 439
agaatctgac atcatgacaa caaatggtgt aattcatgtt gtagataaac tcctctatcc    60

<210> SEQ ID NO 440
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 440
aggaagttgc aagccaacaa aaaagttcaa ggatctagaa gacgattaag ggaaggtcgt    60

<210> SEQ ID NO 441
<211> LENGTH: 60

<212> TYPE: DNA
<213> ORGANISM: Artificial Sequence
<220> FEATURE:
<223> OTHER INFORMATION: Synthetic oligonucleotide

<400> SEQUENCE: 441
ttgagccctt gccgggcctt ttttccacct gccaattcta catgtattgt tgtggtttta    60

<210> SEQ ID NO 442
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 442
tctccaggca gtagatcctc ttcaagatcc tgctattact atgagtcaag ccactacaga    60

<210> SEQ ID NO 443
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 443
aatcactgta gtctaagacc tgatctatag atgacctaga atagccatgt actataatgt    60

<210> SEQ ID NO 444
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 444 tttttttaaat gtgcagtaca catcagcctc actgagctaa taaagggaaa cgaatgtttc    60

<210> SEQ ID NO 445
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 445
tctcaatcac tactcttctt gaagcactat tatttattct tccgctgtct gcctgcagca    60

<210> SEQ ID NO 446
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 446
actgatcaac agcatggacc agaatatgtt caggaacttt tccttcatga accccgggat    60

<210> SEQ ID NO 447
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 447
tggggtgttt gttcccattg gatgcatttc tatcaaaact ctatcaaatg tgatggctag    60

<210> SEQ ID NO 448
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 448
tcaaatgtga tggctagatt ctaacatatt gccatgtgtg gagtgtgctg aacacacacc    60

<210> SEQ ID NO 449
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 449
tcaaatgtga tggctagatt ctaacatatt gccatgtgtg gagtgtgctg aacacacacc    60

<210> SEQ ID NO 450
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 450
agcagcacag gaatcttact tcttggcagc tgcagtctgt caagatgaga catcagatta    60

<210> SEQ ID NO 451
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 451
ccagaacaaa ttttaacaaa aggacaacca cagagggata tagtgaatat cgtatcattg    60

<210> SEQ ID NO 452
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 452
tatacgaagc tggaatttga tgaagcaagg agcttctgga ataaaggaaa ttattcaaga    60

<210> SEQ ID NO 453
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 453
tggtactgtg atgcatttca agtggcagtt ttatcacgtt tgaatctacc attcatagcc    60

<210> SEQ ID NO 454
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 454
atttgatttc cggacatatg attcagaagg cgtgatactg tacgcagaat ctatcgatca    60

<210> SEQ ID NO 455
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 455
cagtgaagcc actaaccctg gagctagtgg aggaaactgt gcaggctatg gaggtggagt    60

<210> SEQ ID NO 456
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 456
acactgagct cacccacaga gcccgtgaag aggtctggcc gctaccactt tgtgcctgga    60

<210> SEQ ID NO 457
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 457
ccagctgcct attgatttaa gctttcctgt tgaatgacaa agtatgtggt tttgtaattt    60

<210> SEQ ID NO 458
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 458
gaacatggtt tgactcatct tatatgggaa accatgtagc agtgagtcat atcttaatat    60

<210> SEQ ID NO 459
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 459
tcttgtgaat ggactgtcag ctgttaaact gttcctgttt tgaagtgcta ttaccttct     60

<210> SEQ ID NO 460
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 460
tgatcatttt ttggcaatta atcagaagaa gagtgggaag ccggtattca tttataagca    60
```

<210> SEQ ID NO 461
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 461
agaccaaaaa atgtaaccga ttcattgagc acctacatta atgctaatta tattaggggc    60

<210> SEQ ID NO 462
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 462
gttttaacta cttgtctctc ttttgctaag aagggatttt tgaatatgct atctacctgg    60

<210> SEQ ID NO 463
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 463
actcaagcta ctggcacata atgaaagatt acttcatgac attccattgc tcttcttttg    60

<210> SEQ ID NO 464
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 464
caagctactg gcacatagtg aaagattact tctgacattc cattgctctt cttttgaaaa    60

<210> SEQ ID NO 465
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 465 aaatttttgga ttgtatgttc aggagaagag ggatggattg aaaagaaggc agcagctaga   60

<210> SEQ ID NO 466
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 466
tctgggtctc aggacagtga tgttggctag cccaggggaa tgtattttc aaaacataca    60

<210> SEQ ID NO 467
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 467
taagacatga aaggttggcc ttactgttga acaagaagta aatccacagg ctcctgttat    60

<210> SEQ ID NO 468
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 468
tgagactcat ctgggatttg gctttccttg gaagctctta cgtgatgtgg gaaatgacaa    60

<210> SEQ ID NO 469
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 469
aggcgttctc tagatccttt cctctgtttc cctctctcgc tggcaaaagt atgatctaat    60

<210> SEQ ID NO 470
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 470
gatggtacat gacttgattc aacgtttggt tctgaactta cacactgatg cgtttactca    60

<210> SEQ ID NO 471
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 471
ggttagatgc caccatgtag ggattatcgc gagtggttga ccttacactt actccttaaa    60

<210> SEQ ID NO 472
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 472
gcttttctgt aataagcttc cttttataat agtgctcagc ttagctctct cagatcctat    60

<210> SEQ ID NO 473
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 473
tgcacggttt acgccacaaa agtgctcttg acatccgtga caccgttttg acttttgtt    60

<210> SEQ ID NO 474

<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 474
gggctactgc cactgtgtgc cttccgccaa cacctcctgt ccccacctaa gcctggtggg    60

<210> SEQ ID NO 475
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 475
tagctgcctt cgcaccttgc tgtgtgacct gaggccctca ctgagcctca atttcctcat    60

<210> SEQ ID NO 476
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 476 gtggggtga gggctccgg gtcactgctg tatataactc cctcccca gaaaataaa    60

<210> SEQ ID NO 477
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 477
ctcacagtgg cctgtaacaa tttcttctgg gagaacagtt gagcagacag ccacattggg    60

<210> SEQ ID NO 478
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 478
ataagcagcc caggaagaaa tgaaaactcc tctgatgtgg ttgggggtc tgccagctgg    60

<210> SEQ ID NO 479
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 479
cttccacaag tactcgggca aagagggtga caagttcaag ctcaacaagt cagaactaaa    60

<210> SEQ ID NO 480
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 480
ccaaaagtgt tgttggcaa ttattcccct aggctgagcc tgctcatgta cctctgatta    60

<210> SEQ ID NO 481
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 481
cttaaccaaa cggatgaaac tctgagcaat gttgaggtgt ttatgcaatt aatatatgac    60

<210> SEQ ID NO 482
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 482
cttaaccaaa cggatgaaac tctgagcaat gttgaggtgt ttatgcaatt aatatatgac    60

<210> SEQ ID NO 483
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 483
aacataaaag ctaggagatg tggcatctga acatttttgc tttgctgcca gagtaaccct    60

<210> SEQ ID NO 484
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 484
ggtcatgtgt gctagttcac cagagaaaat tgaaatcttg gctcctccaa atgggtctgt    60

<210> SEQ ID NO 485
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 485
aacaactgtc agttcatcct gcatgggaaa aatgttggaa tgggagtctg aaatggggct    60

<210> SEQ ID NO 486
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 486
gtatgctggt agctagtgat ttacacaggt ttagttgact aatgaggcat tacaaataat    60

<210> SEQ ID NO 487
<211> LENGTH: 60
<212> TYPE: DNA

<213> ORGANISM: Artificial Sequence
<220> FEATURE:
<223> OTHER INFORMATION: Synthetic oligonucleotide

<400> SEQUENCE: 487
catgctctcc aaaccacttt ttgcagcttt ctctagttca agttcaccag actctataaa    60

<210> SEQ ID NO 488
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 488
gacaacattt gatcccaaga aaccagaat ggaaccctt cacttcaaaa actcagttat    60

<210> SEQ ID NO 489
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 489
tgtgtgcata ctctagaaga gtagggaaaa taatgcttgt tacaattcga cctaatatgt    60

<210> SEQ ID NO 490
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 490
tgaccactgg agagtctaag ccatccttag catgggcatc catcttccta aactgttatt    60

<210> SEQ ID NO 491
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 491
gtagtgctta tacctatata gtccaaagga agaatgacag ctgccctgaa gtgaaggtgt    60

<210> SEQ ID NO 492
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 492 atccctgca gtgcactgta gaacagaaga taagaactt tctctgaatt tgggtcttct    60

<210> SEQ ID NO 493
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 493
tatgtatgat gtgatctggt ccagccaggg cctggtttgt cagctatcta ggtttgataa    60

<210> SEQ ID NO 494
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 494
gagatatgta gaaagactct ttggttcaca ttccgatatt aaaatagtga catgaactgg    60

<210> SEQ ID NO 495
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 495
aatagttttt gttaaacctt ttgtaaagta ccaaggctcc cattaacaaa ttacggcctc    60

<210> SEQ ID NO 496
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 496
actacatttt aaagggaatg tgtatgtgaa gagcactacc aacatcgctt ttgttttaag    60

<210> SEQ ID NO 497
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 497
agatagcaga agagtaaata agtactcagt attgaccacc tacatctgaa atctacaaca    60

<210> SEQ ID NO 498
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 498
gaaatccaaa atagtcatgt ttctgcagta ttctgtagcc aacttaaacc tgtgctttca    60

<210> SEQ ID NO 499
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 499
cattgtgaat cccttttgcct tggaatccac aatccttgac aacgaagact cagacaccaa    60

<210> SEQ ID NO 500
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 500
ttggggatga ttcttacctt ggtaattaaa tgaagctaca catttgggta atctagcaaa       60

<210> SEQ ID NO 501
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 501
gtacctaagt aaggatgatc taggataagt aactcctgtt ttatattgag tactttaggg       60

<210> SEQ ID NO 502
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 502
gtgaacattt caaccagcct tatagctgtt ctcatcatca ccttctgcat tgtgaccgtg       60

<210> SEQ ID NO 503
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 503
caaggcaaat gattttgtgt ttcttgatga cagactatta agtttgggac ttattttccc       60

<210> SEQ ID NO 504
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 504
aggtcctttc caccctgaga cttggctcca ccactgatat cctcctttgg ggaaaggctt       60

<210> SEQ ID NO 505
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 505
acagcaggat ttcaggaagt gccagttgat caatgaataa ataaatgagc ctatttctct       60

<210> SEQ ID NO 506
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 506
aagagatgtt gtcctgacac ttgtggcatc aaatgcctgg atcctgttga caccccaaac       60

```
<210> SEQ ID NO 507
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 507
tttaagagcg atcctcatcc cttcagcaat atgtatttga gttcacacta tttctgtttt      60

<210> SEQ ID NO 508
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 508
aagagtggca gaggctacta caaaaagcaa cctttcatt ttcactaaga gtttaaaagc       60

<210> SEQ ID NO 509
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 509
gaagataatc gatagtcatg ttttttagac tctctgtatt gcttggtaag ctacgtagta     60

<210> SEQ ID NO 510
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 510
ttgatgtgtg ggagcacgct tactaccttc agtataaaaa tgtcaggcct gattatctaa     60

<210> SEQ ID NO 511
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 511
cgtctgggat gaaggcttgt cagcacttcc agtttagaac gcaatgtttc tagagacata    60

<210> SEQ ID NO 512
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 512
ctctggagaa agctctggag gcctttgaaa catttaaaaa gggattgggg ttgaaaatca    60

<210> SEQ ID NO 513
<211> LENGTH: 60
<212> TYPE: DNA
<213> ORGANISM: Artificial Sequence
<220> FEATURE:
<223> OTHER INFORMATION: Synthetic oligonucleotide
```

<400> SEQUENCE: 513
gtagccatga catagcttga gctatagcct ttaattcctt actttggcta tgggtggagg    60

<210> SEQ ID NO 514
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 514
cagcacttcc agtttagaac gcaatgtttc tagagacata ttggctgttt gttttgatga    60

<210> SEQ ID NO 515
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 515
atgagggctg agttatgaaa agataacttc tgaagactta actggcccag aagctgattt    60

<210> SEQ ID NO 516
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 516
accctatttc caagttcaag ttaactagct tgaatgtgt cccaaaacag cttcctccat    60

<210> SEQ ID NO 517
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 517
gtcccaaaac agcttcctcc atttcctgaa agtttattga tcaaagaaat gttgtcccgg    60

<210> SEQ ID NO 518
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 518
ctgggcgcgc ctccgctcga cggctacccg ttgcccacgc ccgacacgtc cccgctggac    60

<210> SEQ ID NO 519
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 519
ccgccatgaa ctacgacaag ctgagccgct ccatccgcca gtattacaag aagggcatca    60

<210> SEQ ID NO 520
<211> LENGTH: 60

```
<212> TYPE: DNA
<213> ORGANISM: Artificial Sequence
<220> FEATURE:
<223> OTHER INFORMATION: Synthetic oligonucleotide

<400> SEQUENCE: 520
ttccacagcc atgaatttca cagccatgaa gatatgctgg ttgtagaccc caaaagtaag      60

<210> SEQ ID NO 521
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 521
gaatgtaata agaatctggt ggtgtcaatt gcttacttgt tttcccacag ttgtccagca      60

<210> SEQ ID NO 522
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 522
gaaatatagt ccaagctttc tctgtggaaa aagacaaaac tcattagtag acatgtttcc      60

<210> SEQ ID NO 523
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 523
tcattagtag acatgtttcc ctattgcttt cataggcacc agtcagaata aagaatcata      60

<210> SEQ ID NO 524
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 524 atatccccatt ggatttcact tgcattgtgc aataagcaaa gaagggttga taaaagttct      60

<210> SEQ ID NO 525
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 525
ctggaagaga acaccatttt atctcaggtt agtgaagaat cagtgcaggt ccctgactct      60

<210> SEQ ID NO 526
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 526
```
aattaaagag gtaccctttg agacactagc ccagtggaat ctagaacacg ctactttaaa    60

<210> SEQ ID NO 527
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 527
agggaactaa tgcaactgga aaaggagctg gtagaacgtc aacctcaagt ggacatgtta    60

<210> SEQ ID NO 528
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 528
aacctcaagt ggacatgtta caggagattt caaacagcct tctcattaag ggacatggag    60

<210> SEQ ID NO 529
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 529
aatctgggag gcagaagcca aatctgtttt ggatcaagat gatgtggaca cctcaatgga    60

<210> SEQ ID NO 530
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 530
caatgcgcca cctatgagtc tgtcaatgtg accgatttta agtcaagttg gagaaatggg    60

<210> SEQ ID NO 531
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 531
aagaagctaa agagaaagtc cagatcaatg tggtaaaact cattgcagcg ttgaagaact    60

<210> SEQ ID NO 532
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 532
agctccacgg gaagaacctg gaactgggga agatcatgga caggttcgaa gaggttgtgt    60

<210> SEQ ID NO 533
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 533
ttgaagaaga accagcccag cctgcctcct atcttttcct ggaatatttt tggggttgga      60

<210> SEQ ID NO 534
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 534
acccgtgtgg taccttcagc cctggccaag ctttgaggct ctgtcactga gcaatggtaa      60

<210> SEQ ID NO 535
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 535
ccgtggagat cccaactggt ttatgaagaa agcgcaggag cataagaggg aattcacaga      60

<210> SEQ ID NO 536
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 536
caagcaagag cactgcctct atagggtaac ctggaacatt ctctaggtta tatcaatata      60

<210> SEQ ID NO 537
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 537
gccggaagct gatgaacatc gccttcaatg acatgaaccc cttccgcatg aaacagctgc      60

<210> SEQ ID NO 538
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 538
ccagaaaatg aatgatacta tatttggttt cacaatggag gagcgctcat gggggccta       60

<210> SEQ ID NO 539
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 539
tccgcccttc cctgacactg tctgctgccc caatcgccgt cacaataaaa gaaagtgtgg      60
```

<210> SEQ ID NO 540
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 540
tcacaggctc tccgtggcct ggaactgcag ccccagctgc atcctacacc cccaccccaa    60

<210> SEQ ID NO 541
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 541
ctgtccacgc tgtactggtt cacggtggag ttcgggctgt gtaagcagaa cggggaggtg    60

<210> SEQ ID NO 542
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 542
ggatgaggaa attgagaagc tgtccacgct gtcatggttc acggtggagt tcgggctgtg    60

<210> SEQ ID NO 543
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 543
ttccagactg cttccaattt ttctggaaca cattaaatat ggatcagtta taagtagcag    60

<210> SEQ ID NO 544
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 544
acagggtctg caaggtcttt ggttcagcta agctaggaat gaaatcctgc ttcagtgtat    60

<210> SEQ ID NO 545
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 545
tctttctgta accataacaa cttcatatat gaggacttgt gtctctgtgc ttttaaatgc    60

<210> SEQ ID NO 546
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 546 acttttact tttttgcgtg tggagctgta ttcccgagac caacgaagcg ttgggatact        60

<210> SEQ ID NO 547
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 547
tcgttgtgtt gttttgctgc acttttact tttttgcgtg tggagctgta ttcccgagac        60

<210> SEQ ID NO 548
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 548
tgtggagtga aaatgggca tgccattaca ttgctttttc ttggtggtta aaagaatga        60

<210> SEQ ID NO 549
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 549
caagatggca cccaagtgtt tggcttctgg ctacctaagg ttaacatgtc actagagtat        60

<210> SEQ ID NO 550
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 550
ctgtctagaa ggaatgtatt tgttgctaaa ttttgtagca ctgtttacag ttttcctcca        60

<210> SEQ ID NO 551
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 551
ccttttatgg aaaccgtttt ttaaaaaagt gaatgtacac aaatccacag aagactgtgg        60

<210> SEQ ID NO 552
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 552
atgagtgatc taaatttgca gcaatgatac taaacaactc tctgaaattt ctcaagcacc        60

<210> SEQ ID NO 553

<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 553
cttatctggt gtgttcatat agaatcacct agaaggataa agtcgctgta gagttaatga    60

<210> SEQ ID NO 554
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 554
tcagggtttc aagaagtctt agggcttcca ggggtcccct ggaagcttta gaatatttat    60

<210> SEQ ID NO 555
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 555
gaagaaactg cttgttgtgt atcagtaatc attagtggca atgatgacat tctgaaaagc    60

<210> SEQ ID NO 556
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 556
aagaaactgc ttgttgtgta tcagtaatca ttagtggcaa tgatgacatt ctgaaaagct    60

<210> SEQ ID NO 557
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 557
gccgggctgg ggctgcgtag gtgaaaaggc agaacactcc gcgcttctta gaagaggagt    60

<210> SEQ ID NO 558
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 558
tgtagttctt gcatcctata ctggataagc ctgttttaac ctgctatgat gggtgcttcc    60

<210> SEQ ID NO 559
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 559 tagagattttt aggcgtcttc ggatatcttc tcacctatgt tccctggcta agaagtcaga    60

<210> SEQ ID NO 560
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 560
tgtgaggcga ttattttaag taattatctt accaagccca agactggttt taaagttacc    60

<210> SEQ ID NO 561
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 561
ctcacctttg ggacaggcac tcagctagaa gtgggactca atatccagaa ccctgaccct    60

<210> SEQ ID NO 562
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 562
atcttcagtg ggttctcttg ggctctaggt cctggagaat gttgtgaggg gtttattttt    60

<210> SEQ ID NO 563
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 563
tttctttaac cattttgaa acccttcaaa ggcagagact tgtccagcct aacctgcctg    60

<210> SEQ ID NO 564
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 564
atcattcatg gtctaaaaaa caatgaaacc aatgaaatgg cctctctgat catcacagaa    60

<210> SEQ ID NO 565
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 565
tagtgttcat aaagaaatac atagtattct tcttctcaag acgtgggggg aaattatctc    60

<210> SEQ ID NO 566
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 566
tctggctgtg ggataaatgt gtgtgggaat attgaaacat cgcctaggaa ttgtggtttg    60

<210> SEQ ID NO 567
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 567 agccccttc ccttgtcaat gacagtcatc ctaatgataa taaaacctgc atccagataa    60

<210> SEQ ID NO 568
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 568
gctgattggg gaataatttt caacactat cctgaattat gtgcctgtct agataagcag    60

<210> SEQ ID NO 569
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 569
ttgagatact gggtttggtg ttttctatgg tcctgtattg ccagatcggg aacaaatgaa    60

<210> SEQ ID NO 570
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 570
tgatgactct gcttctatga ggtcaccagc agtagaacca tatcttgctg gcatacactt    60

<210> SEQ ID NO 571
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 571
atccaactta tccaaaaatc agaaaggata tacttgataa ggcccgtgcg tctttaagac    60

<210> SEQ ID NO 572
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 572
aaagccaaca tgaaggggtc atatagtctt gtagaagcac agaaatcaaa agtgtagcta    60
```

<210> SEQ ID NO 573
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 573
ctttactgcg aataagcttt taatgctcca aatgctgacc catgcaatat ttcctcatgt    60

<210> SEQ ID NO 574
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 574
agtttatact cacctttat gaaagcactg catgaataaa attattcctt tgtatttta    60

<210> SEQ ID NO 575
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 575
cactcttaga gtccagcttg taatggttct ttacacatga gtcacaagtt acagctgtga    60

<210> SEQ ID NO 576
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 576
tcactgcata cattgtggaa ggtgtaggga gtgaagtctc acataggagg acctgtgtga    60

<210> SEQ ID NO 577
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 577
catgaataaa gttattcctt tgtattttta cttttaaatg tcttctgcat tcacttatat    60

<210> SEQ ID NO 578
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 578
ccagttagca gaatcaagac ctacaccatc acggaaggct ccttgagagc agtaattttt    60

<210> SEQ ID NO 579
<211> LENGTH: 60
<212> TYPE: DNA
<213> ORGANISM: Artificial Sequence
<220> FEATURE:

```
<223> OTHER INFORMATION: Synthetic oligonucleotide

<400> SEQUENCE: 579
ctcatttcac tttacaccct catggactga gattatactc accttttatg aaagcactgc        60
```